US007626010B2

(12) United States Patent
Burns et al.

(10) Patent No.: US 7,626,010 B2
(45) Date of Patent: Dec. 1, 2009

(54) SPINOSYN-PRODUCING POLYKETIDE SYNTHASES

(75) Inventors: Lesley S. Burns, Cambridge (GB); Paul R. Graupner, Carmel, IN (US); Paul Lewer, Indianapolis, IN (US); Christine J. Martin, Cambridge (GB); William A. Vousden, Dry Drayton (GB); Clive Waldron, Indianapolis, IN (US); Barrie Wilkinson, Sharnbrook (GB)

(73) Assignee: Dow AgroSciences LLC, Indianapolis, IN (US)

(*) Notice: Subject to any disclaimer, the term of this patent is extended or adjusted under 35 U.S.C. 154(b) by 615 days.

(21) Appl. No.: 11/254,686

(22) Filed: Oct. 20, 2005

(65) Prior Publication Data

US 2006/0040877 A1    Feb. 23, 2006

Related U.S. Application Data

(62) Division of application No. 10/368,770, filed on Feb. 19, 2003, now abandoned.

(60) Provisional application No. 60/358,075, filed on Feb. 19, 2002.

(51) Int. Cl.
| | |
|---|---|
| C12N 15/62 | (2006.01) |
| C12N 15/52 | (2006.01) |
| C12N 15/53 | (2006.01) |
| C12N 15/74 | (2006.01) |
| C12N 15/76 | (2006.01) |
| C12P 19/62 | (2006.01) |

(52) U.S. Cl. ............... 536/23.4; 435/76; 435/183; 435/189; 435/252.3; 435/252.35; 536/23.2

(58) Field of Classification Search .............. None
See application file for complete search history.

(56) References Cited

U.S. PATENT DOCUMENTS

| | | | | |
|---|---|---|---|---|
| 5,824,513 | A * | 10/1998 | Katz et al. | 435/76 |
| 6,004,787 | A * | 12/1999 | Katz et al. | 435/183 |
| 6,143,526 | A * | 11/2000 | Baltz et al. | 435/76 |
| 6,274,350 | B1 * | 8/2001 | Baltz et al. | 435/76 |
| 6,492,562 | B1 * | 12/2002 | Ashley et al. | 568/75 |
| 6,521,406 | B1 * | 2/2003 | Baltz et al. | 435/6 |
| 6,864,073 | B1 * | 3/2005 | Omura et al. | 435/183 |
| 7,001,747 | B1 * | 2/2006 | Kellenberger et al. | 435/76 |
| 7,015,001 | B2 * | 3/2006 | Baltz et al. | 435/6 |
| 7,022,825 | B2 * | 4/2006 | Ashley et al. | 536/7.2 |

(Continued)

OTHER PUBLICATIONS

Kuhstoss et al., 1996, "Production of a novel polyketide through the construction of a hybrid polyketide synthase", Gene, vol. 183, pp. 231-236.*

(Continued)

*Primary Examiner*—David J Steadman
*Assistant Examiner*—William W Moore
(74) *Attorney, Agent, or Firm*—Donald Stuart

(57) ABSTRACT

The invention provides, biologically active spinosyns, hybrid spinosyn polyketide synthases capable of functioning in *Saccharopolyspora spinosa* to produce the spinosyns, and methods of controlling insects using the spinosyns.

3 Claims, 13 Drawing Sheets

U.S. PATENT DOCUMENTS

| | | | |
|---|---|---|---|
| 7,148,045 B1* | 12/2006 | Leadlay et al. | 435/183 |
| 7,198,922 B2* | 4/2007 | Leadlay et al. | 435/76 |
| 7,285,653 B1* | 10/2007 | Eberz et al. | 536/23.2 |
| 7,371,548 B2* | 5/2008 | Omura et al. | 435/183 |
| 2004/0219645 A1* | 11/2004 | Leadley et al. | 435/76 |
| 2005/0090461 A1* | 4/2005 | Leadlay et al. | 514/29 |
| 2006/0240528 A1* | 10/2006 | Leadlay et al. | 435/76 |

OTHER PUBLICATIONS

Oliynyk et al. 1996, "A hybrid modular polyketide synthase obtained by domain swapping", Chem. Biol., vol. 10, pp. 833-839.*

Khosla, C., 1997, "Harnessing the biosynthetic potential of modular polyketide synthases", Chemical Reviews, vol. 97, pp. 2577-2590.*

Marsden et al., 1998, "Engineering broader specificity into an antibiotic-producing polyketide synthase", Science, vol. 279, pp. 199-202.*

Waldron, C., et al., 2000, "A cluster of genes for the biosynthesis of spinosyns, novel macrolide insect control agents produced by *Saccharopolyspora spinosa*", Antonie van Leeuwenhoek, vol. 78, Nos. 3-4, pp. 385-390.*

Waldron, C., et al., 2001, "Cloning and analysis of the spinosad gene cluster of *Saccharopolyspora spinosa*", Chemistry & Biology, vol. 8, No. 5, pp. 487-499.*

Madduri, K., et al., 2001, "Genes for the biosynthesis of spinosyns: applications for improvement in *Saccharopolyspora spinosa*", Journal of Industrial Microbiology & Biotechnology, vol. 27, No. 6, pp. 399-402.*

* cited by examiner

SPINOSYN-PRODUCING POLYKETIDE SYNTHASES

RELATED APPLICATIONS

This application is a divisional filing of U.S. utility application Ser. No. 10/368,770, filed Feb. 19, 2003 and now abandoned, which claims the benefit of U.S. Provisional Application No. 60/358,075, filed Feb. 19, 2002.

SUMMARY OF THE INVENTION

The present invention provides novel hybrid polyketide synthases (PKSs), DNA encoding such PKSs, vectors incorporating the hybrid polyketide synthase DNA, host organisms including but not limited to *Saccharopolyspora spinosa* strains transformed with the hybrid polyketide synthase DNA, methods of using the hybrid polyketide synthase DNA to change the products made by spinosyn-producing strains, and the novel biologically-active compounds generated by these manipulations.

BACKGROUND OF THE INVENTION

As disclosed in U.S. Pat. No. 5,362,634, fermentation product A83543 is a family of related compounds produced by *Saccharopolyspora spinosa*. The family of natural spinosyn compounds that have previously been isolated are described in U.S. Pat. No. 6,274,350 B1 and WO 01/19840, along with their activities in a variety of insect control assays. A number of semi-synthetic spinosyn analogues are also described in U.S. Pat. No. 6,001,981, in which the chemically accessible areas of the spinosyn molecule were successfully substituted in a variety of ways.

The known members of this family have been referred to as factors or components, and each has been given an identifying letter designation. These compounds are hereinafter referred to as spinosyn A, B, etc. The spinosyn compounds are useful for the control of arachnids, nematodes and insects, in particular *Lepidoptera* and *Diptera* species, and they are quite environmentally friendly and have an appealing toxicological profile. The commercial product Spinosad is a mixture of spinosyns A and D (*Pesticide Manual*, 11th ed., p. 1272).

Tables 1 and 2 identify the structures of some known spinosyn compounds:

TABLE 1

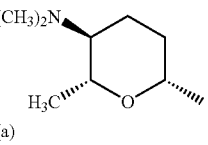

| Factor | R1 | R2 | R3 | R4 | R5 | R6 | R7 |
|---|---|---|---|---|---|---|---|
| spinosyn A | H | $CH_3$ | $(CH_3)_2N$ (a) | $C_2H_5$ | $CH_3$ | $CH_3$ | $CH_3$ |
| spinosyn B | H | $CH_3$ | $CH_3NH$ (b) | $C_2H_5$ | $CH_3$ | $CH_3$ | $CH_3$ |
| spinosyn C | H | $CH_3$ | $H_2N$ (c) | $C_2H_5$ | $CH_3$ | $CH_3$ | $CH_3$ |
| spinosyn D | $CH_3$ | $CH_3$ | (a) | $C_2H_5$ | $CH_3$ | $CH_3$ | $CH_3$ |
| spinosyn E | H | $CH_3$ | (a) | $CH_3$ | $CH_3$ | $CH_3$ | $CH_3$ |
| spinosyn F | H | H | (a) | $C_2H_5$ | $CH_3$ | $CH_3$ | $CH_3$ |
| spinosyn A 17-Psa | H | $CH_3$ | H | $C_2H_5$ | $CH_3$ | $CH_3$ | $CH_3$ |
| spinosyn D 17-Psa | $CH_3$ | $CH_3$ | H | $C_2H_5$ | $CH_3$ | $CH_3$ | $CH_3$ |

TABLE 1-continued

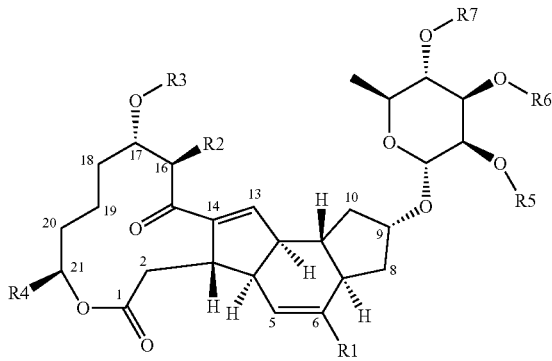

| Factor | R1 | R2 | R3 | R4 | R5 | R6 | R7 |
|---|---|---|---|---|---|---|---|
| spinosyn E 17-Psa | H | $CH_3$ | H | $CH_3$ | $CH_3$ | $CH_3$ | $CH_3$ |
| spinosyn F 17-Psa | H | H | H | $C_2H_5$ | $CH_3$ | $CH_3$ | $CH_3$ |

TABLE 2

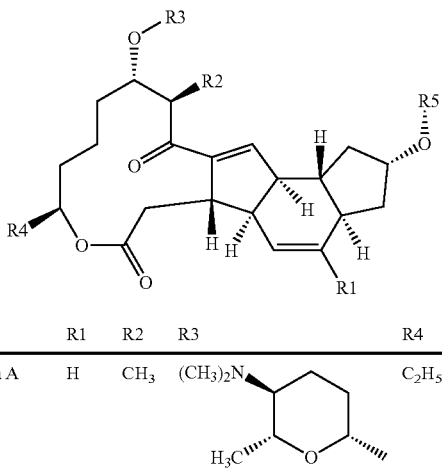

| Factor | R1 | R2 | R3 | R4 | R5 |
|---|---|---|---|---|---|
| spinosyn A 9-Psa | H | $CH_3$ | $(CH_3)_2N$ ... (a) | $C_2H_5$ | H |
| spinosyn D 9-Psa | $CH_3$ | $CH_3$ | (a) | $C_2H_5$ | H |
| spinosyn A aglycone | H | $CH_3$ | H | $C_2H_5$ | H |
| spinosyn D aglycone | $CH_3$ | $CH_3$ | H | $C_2H_5$ | H |

The naturally produced spinosyn compounds consist of a 5,6,5-tricylic ring system, fused to a 12-membered macrocyclic lactone, a neutral sugar (rhamnose) and an amino sugar (forosamine) (see Kirst et al. (1991). If the amino sugar is not present the compounds have been referred to as the pseudoaglycone of A, D, etc., and if the neutral sugar is not present then the compounds have been referred to as the reverse pseudoaglycone of A, D, etc. A more preferred nomenclature is to refer to the pseudoaglycones as spinosyn A 17-Psa, spinosyn D 17-Psa, etc., and to the reverse pseudoaglycones as spinosyn A 9-Psa, spinosyn D 9-Psa, etc.

The naturally produced spinosyn compounds may be produced via fermentation from cultures NRRL 18395, 18537, 18538, 18539, 18719, 18720, 18743 and 18823. These cultures have been deposited and made part of the stock culture collection of the Midwest Area Northern Regional Research Center, Agricultural Research Service, United States Department of Agriculture, 1815 North University Street, Peoria, Ill. 61604.

U.S. Pat. No. 5,362,634 and corresponding European Patent Application No. 375316 Al disclose spinosyns A, B, C, D, E, F, G, H, and J. These compounds are disclosed as being produced by culturing a strain of the novel microorganism Saccharopolyspora spinosa selected from NRRL 18395, NRL 18537, NRRL 18538, and NRRL 18539.

WO 93/09126 disclosed spinosyns L, M, N, Q, R, S, and T. Also disclosed therein are two spinosyn J producing strains: NRRL 18719 and NRRL 18720, and a strain that produces spinosyns Q, R, S, and T: NRRL 18823.

WO 94/20518 and U.S. Pat. No. 5,670,486 disclose spinosyns K, O, P, U, V, W, and Y, and derivatives thereof. Also disclosed is spinosyn K-producing strain NRRL 18743.

WO 01/19840 discloses spinosyn analogs produced by culturing Saccharopolyspora species LW107129 (NRRL 30141).

WO 99/46387 and U.S. Pat. No. 6,143,526 disclose the spinosyn biosynthetic genes from Saccharopolyspora spinosa.

The nature of the genes involved in spinosyn biosynthesis, together with previous studies of precursor incorporation (Broughton et al., 1991), indicate that spinosyns are produced by the stepwise condensation of 2-carbon and 3-carbon carboxylic acids to generate a polyketide that is cyclized and bridged. The tetracyclic, aglycone product of these reactions is converted to the pseudoaglycone by addition of a rhamnosyl residue, and synthesis is completed by the addition of the di-N-methylated sugar, forosamine. In some aspects, this process is similar to the biosynthetic pathway by which other macrolides (such as the antibiotic erythromycin, the antihelmintic avermectin, and the immunosuppressant rapamycin) are produced. In particular, the polyketide nucleus is assembled by a very large, multifunctional protein that is a Type I polyketide synthase (spn PKS). This polypeptide complex comprises a loading module and ten extension modules, each module being responsible for both the addition of a specific acyl-CoA precursor to the growing polyketide chain, and for the degree of reduction of the β-keto carbonyl group.

Each module performs several biochemical reactions which are carried out by specific domains of the polypeptide. All the extension modules contain an acyl transferase (AT) domain that donates the acyl group from a precursor to an acyl carrier protein (ACP) domain, and a β-ketosynthase (KS) domain that adds the pre-existing polyketide chain to the new acyl-ACP by decarboxylative condensation. Additional domains are present in some extension modules: β-ketoreductase (KR) domains reduce β-keto groups to hydroxyls, dehydratase (DH) domains remove hydroxyls to leave double bonds, and the enoyl reductase (ER) domain reduces a double bond to leave a saturated carbon. The loading module of the spn PKS is different from the extension modules in that it contains a variant KS domain (KSq), as well as AT and ACP domains. The KSq domain, which is also found in some other Type I PKS loading modules (but not all), is believed to provide the requisite starter unit by decarboxylation of an ACP-bound acyl chain (Bisang et al., 1999). The terminal extension module contains a thioesterase/cyclase (TE) domain that liberates the polyketide chain from the PKS.

The spinosyn PKS DNA region consists of 5 ORFs with in-frame stop codons at the end of some ACP domains, similar to the PKS ORFs in the other macrolide-producing bacteria. The five spinosyn PKS genes are arranged head-to-tail, without any intervening non-PKS functions such as the insertion element found between the erythromycin PKS genes AI and AII (Donadio et al., 1993). They are designated spnA, spnB, spnC, spnD, and spnE. The nucleotide sequence for each of the five spinosyn PKS genes, and the corresponding polypeptides, are identified in U.S. Pat. No. 6,143,526 and in Waldron et al., 2001. Also identified in these sources are the predicted translation products of the PKS genes, and the boundaries of the domains and modules.

After it is synthesized, the spinosyn polyketide precursor condenses to form a macrocyclic lactone, referred to hereinafter as the polyketide nucleus. Production of insecticidally-active spinosyns requires additional processing of the polyketide nucleus. First, carbon-carbon bridges must be formed between C3 and C14, C4 and C12, and C7 and C11, to generate the aglycone intermediate. Possible mechanisms for these unusual reactions have been suggested (Waldron et al., 2001), but the structural features of the polyketide substrate that are required for them to occur are not known. Second, a tri-O-methyl rhamnose must be incorporated at C9 to generate the pseudoaglycone. It is not known if the rhamnose is normally methylated before or after its addition to the aglycone, but S. spinosa is capable of adding the methyl groups after the rhanmose moiety has been conjugated to the aglycone (Broughton et al., 1991). The methylations must occur in a particular sequence (2' then 3' then 4') or not all of them will take place, indicating that the methyltransferases have very specific substrate requirements. The third processing step, addition of forosamine at C17, is needed to produce the most active spinosyns. The enzymes involved in this step also have stringent substrate requirements: the forosaminyl transferase will not use the aglycone as a substrate, and the N-methyltransferase will not act on the forosamine after it has been attached to the pseudoaglycone. This substrate-specificity of later biosynthetic enzymes may be a barrier to producing novel, biologically-active spinosyns from precursors with different chemical structures.

In certain cases polyketide synthase (PKS) genes have previously been manipulated with the objective of providing novel polyketides. In-frame deletion of the DNA encoding part of the KR domain in module 5 of the erythromycin-producing (ery) PKS has been shown to lead to the formation of erythromycin analogues, namely 5,6-dideoxy-3alpha-mycarosyl-5-oxoerythronolide B and 5,6-dideoxy-5-oxoerythronolide B (Donadio et al., 1991). Likewise, alteration of active site residues in the ER domain of module 4 of the ery PKS, by genetic engineering of the corresponding PKS-encoding DNA and its introduction into Saccharopolyspora erythraea, led to the production of 6,7-anhydroerythromycin C (Donadio et al., 1993). WO 93/13663 describes additional types of genetic manipulation of the ery PKS genes that are capable of producing altered polyketides.

WO 98/01546 discloses replacement of the loading module of the ery PKS with the loading module from the avermectin (ave) PKS, to produce a hybrid Type I PKS gene that incorporates different starter units to make novel erythromycin analogues.

However, it has also been found that not all manipulations of PKS genes produce the targeted new analogues. When Donadio et al. (1993) inactivated an ER domain of the ery PKS, the resulting anhydro-derivative could not be completely processed because it was no longer a substrate for the mycarose-O-methyltransferase. Changing the polyketide starter unit prevented complete elongation and elaboration of a rifamycin analogue in Amycolatopsis mediterranei (Hunziker et al., 1998). Given the extensive substrate-specific processing that is required to generate insecticidally-active spinosyns, it is not obvious that genetic modifications which change the structure of a spinosyn polyketide will permit synthesis of a fully-processed molecule with useful biological activity. However, if such analogues could be made, and they had a different spectrum of insecticidal activity, they would be highly desirable because known spinosyns do not control all pests.

BRIEF DESCRIPTION OF THE INVENTION

In one of its aspects, the invention provides a hybrid spinosyn polyketide synthase that is capable of functioning in Saccharopolyspora spinosa to produce a biologically active spinosyn, said hybrid polyketide synthase comprising a heterologous loading module operatively associated with a plurality of Saccharopolyspora spinosa extender modules. In preferred embodiments, the spinosyn loading domain is replaced with the loading domain for the erythromycin PKS or avermectin PKS. The ave and ery loading domains are of particular interest because they accept a variety of starter units. Also useful are hybrid PKS genes in which the heterologous loading module incorporates an unusual starter unit, such as the loading module for rapamycin (cyclohexene carboxylic acid) or for myxathiazole (3-methyl butyric acid). The required precursors, e.g. cyclohexene carboxylic acid or 3-methyl butyric acid, may be provided in the culture medium, or the genes encoding their biosynthetic enzymes may be engineered into the organism so they are synthesized endogenously.

In another of its aspects, the invention provides a hybrid spinosyn polyketide synthase that is capable of functioning in Saccharopolyspora spinosa to produce a biologically active 6-ethyl spinosyn compound, 16-ethyl spinosyn compound, 18-ethyl spinosyn compound, or 20-ethyl spinosyn compound, said hybrid polyketide synthase being the product produced by spinosyn biosynthetic DNA that has been modified so that the DNA for the AT domain of module 8, 3, 2, or 1, respectively, in the spinosyn PKS is replaced with DNA for an AT domain that normally incorporates ethyl malonyl-CoA. In preferred embodiments, the DNA that encodes the relevant spinosyn AT domain is replaced with the DNA that encodes the AT domain of module 5 of the tylosin PKS or module 5 of the monensin PKS. In preferred embodiments, the *Streptomyces cinnamonensis* crotonyl-CoA reductase is co-expressed.

In another of its aspects, the invention provides a hybrid spinosyn polyketide synthase that is capable of functioning in *Saccharopolyspora spinosa* to produce a biologically active 18-methyl spinosyn compound, or 20-methyl spinosyn compound, said hybrid polyketide synthase being the product produced by spinosyn biosynthetic DNA that has been modified so that the DNA for the AT domain of module 2 or 1, respectively, in the spinosyn PKS is replaced with DNA for an AT domain that normally incorporates methyl malonyl-CoA.

In another of its aspects, the invention provides a hybrid spinosyn polyketide synthase that is capable of functioning in *Saccharopolyspora spinosa* to produce a biologically active 16-desmethyl spinosyn compound, said hybrid polyketide synthase being the product produced by spinosyn biosynthetic DNA that has been modified so that the DNA for the AT domain of module 3 in the spinosyn PKS is replaced with DNA for an AT domain that normally incorporates malonyl-CoA. In a preferred embodiment the AT domain of module 3 is replaced with the DNA that encodes the AT domain of module 2 of the rapamycin PKS In another of its aspects, the invention provides a process for producing a 6-ethyl spinosyn compound, a 21-desethyl-21-n-propyl spinosyn compound, or a 6-ethyl-21-desethyl-21-propyl spinosyn compound which comprises culturing a transgenic host organism that coexpresses crotonyl-CoA reductase with the spinosyn biosynthetic pathway. In a preferred embodiment the host organism is transformed with DNA encoding the *S. cinnamonensis* crotonyl-CoA reductase.

In another of its aspects, the invention provides a *Saccharopolyspora spinosa* strain that has been transformed with DNA encoding the *S. cinnamonensis* crotonyl-CoA reductase.

In another of its aspects, the invention provides DNA encoding a hybrid spinosyn polyketide synthase of the invention, as described above.

In another of its aspects, the invention provides a vector comprising DNA as described above.

In another of its aspects, the invention provides a host organism comprising DNA as described above.

In yet another of its aspects, the invention provides a compound of the formula (I)

(I)

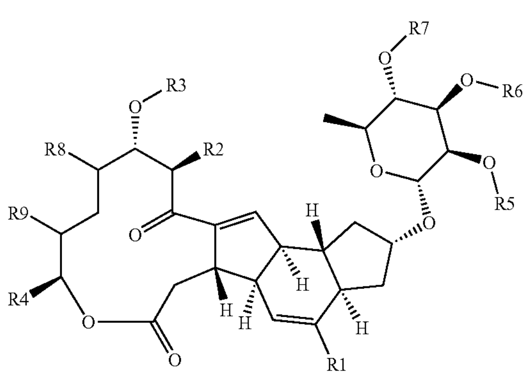

wherein

R1 is hydrogen, methyl, or ethyl;

R2 is hydrogen, methyl, or ethyl;

R3 is hydrogen, (a)

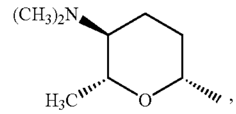

(b)

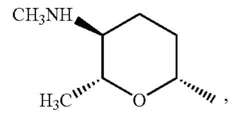

(c)

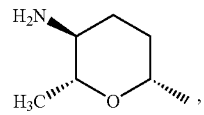

or (d)

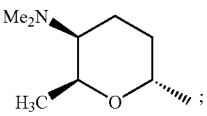

R4 is methyl or ethyl, either of which may be substituted with one or more groups selected from halo, hydroxy, $C_1$-$C_4$ alkyl, $C_1$-$C_4$ alkoxy, $C_1$-$C_4$ alkylthio, or cyano;

R4 is an alpha-branched $C_3$-$C_5$ alkyl group, $C_3$-$C_8$ cycloalkyl group, or $C_3$-$C_8$ cycloalkenyl group, any of which may be substituted with one or more groups selected from halo, hydroxy, $C_1$-$C_4$ alkyl, $C_1$-$C_4$ alkoxy, $C_1$-$C_4$ alkylthio, or cyano; or R4 is a 3-6 membered heterocyclic group that contains O or S, that is saturated or fully or partially unsaturated, and that may be substituted with one or more groups selected from halo, hydroxy, $C_1$-$C_4$ alkyl, $C_1$-$C_4$ alkoxy, $C_1$-$C_4$ alkylthio, or cyano;

R5 is hydrogen or methyl;

R6 is hydrogen or methyl;

R7 is hydrogen or methyl;

R8 is hydrogen, methyl, or ethyl;

R9 is hydrogen, methyl, or ethyl;

or a 5,6-dihydro derivative of a compound of formula I, provided that:

a) R4 is methyl or ethyl substituted with one or more groups selected from halo, hydroxy, $C_1$-$C_4$ alkyl, $C_1$-$C_4$ alkoxy, $C_1$-$C_4$ alkylthio, or cyano; or b) R4 is an alpha-branched $C_3$-$C_5$ alkyl group, $C_3$-$C_8$ cycloalkyl group, or $C_3$-$C_8$ cycloalkenyl group, any of which may be substituted with one or more groups selected from halo, hydroxy, $C_1$-$C_4$ alkyl, $C_1$-$C_4$ alkoxy, $C_1$-$C_4$ alkylthio, or cyano; or c) R4 is a 3-6 membered heterocyclic group that contains O or S, that is saturated or fully or partially unsaturated, and that may be substituted with one or more groups selected from halo, hydroxy, $C_1$-$C_4$ alkyl, $C_1$-$C_4$ alkoxy, $C_1$-$C_4$ alkylthio, or cyano; or d) R1 or R2 is ethyl; or e) R8 is methyl or ethyl; or f) R9 is methyl or ethyl.

Illustrative compounds provided by the invention are identified in the following Table 3. Compound numbers cited hereinafter refer to the compounds identified in Table 3.

TABLE 3

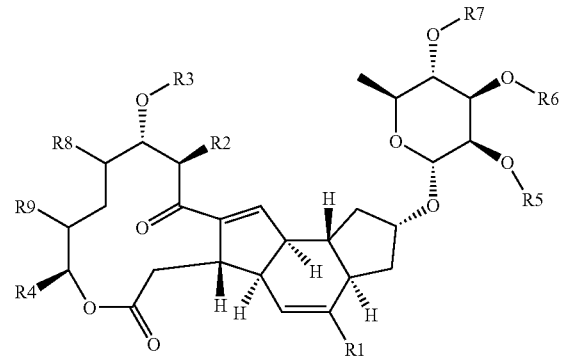

(I)

| cmpd no. | name | R1 | R2 | R3 | R4 | R5 | R6 | R7 | R8 | R9 |
|---|---|---|---|---|---|---|---|---|---|---|
| 1 | 21-desethyl-21-cyclopropyl spinosyn A | H | $CH_3$ | (a) | cyclopropyl | $CH_3$ | $CH_3$ | $CH_3$ | H | H |
| 2 | 21-desethyl-21-cyclopropyl spinosyn D | $CH_3$ | $CH_3$ | (a) | cyclopropyl | $CH_3$ | $CH_3$ | $CH_3$ | H | H |
| 3 | 21-desethyl-21-cyclobutyl spinosyn A | H | $CH_3$ | (a) | cyclobutyl | $CH_3$ | $CH_3$ | $CH_3$ | H | H |
| 4 | 21-desethyl-21-cyclobutyl spinosyn D | $CH_3$ | $CH_3$ | (a) | cyclobutyl | $CH_3$ | $CH_3$ | $CH_3$ | H | H |
| 5 | 21-desethyl-21-methylthiomethyl spinosyn A | H | $CH_3$ | (a) | methylthio-methyl | $CH_3$ | $CH_3$ | $CH_3$ | H | H |
| 6 | 21-desethyl-21-methylthiomethyl spinosyn D | $CH_3$ | $CH_3$ | (a) | methylthio-methyl | $CH_3$ | $CH_3$ | $CH_3$ | H | H |
| 7 | 21-desethyl-21-cyanomethyl spinosyn A | H | $CH_3$ | (a) | cyanomethyl | $CH_3$ | $CH_3$ | $CH_3$ | H | H |
| 8 | 5,6-dihydro-21-desethyl-21-cyclobutyl spinosyn A | H | $CH_3$ | (a) | cyclobutyl | $CH_3$ | $CH_3$ | $CH_3$ | H | H |
| 9 | 21-desethyl-21-isopropyl spinosyn A | H | $CH_3$ | (a) | isopropyl | $CH_3$ | $CH_3$ | $CH_3$ | H | H |
| 10 | 21-desethyl-21-isopropyl spinosyn D | $CH_3$ | $CH_3$ | (a) | isopropyl | $CH_3$ | $CH_3$ | $CH_3$ | H | H |
| 11 | 21-desethyl-21-sec-butyl spinosyn A | H | $CH_3$ | (a) | sec-butyl | $CH_3$ | $CH_3$ | $CH_3$ | H | H |
| 12 | 21-desethyl-21-sec-butyl spinosyn D | $CH_3$ | $CH_3$ | (a) | sec-butyl | $CH_3$ | $CH_3$ | $CH_3$ | H | H |
| 13 | 21-desethyl-21-methylcyclopropyl spinosyn A | H | $CH_3$ | (a) | methylcyclo-propyl | $CH_3$ | $CH_3$ | $CH_3$ | H | H |
| 14 | 21-desethyl-21-methylcyclopropyl spinosyn D | $CH_3$ | $CH_3$ | (a) | methylcyclo-propyl | $CH_3$ | $CH_3$ | $CH_3$ | H | H |
| 15 | 21-desethyl-21-(3-furyl) spinosyn A | H | $CH_3$ | (a) | 3-furyl | $CH_3$ | $CH_3$ | $CH_3$ | H | H |
| 16 | 21-desethyl-21-(3-furyl) spinosyn D | $CH_3$ | $CH_3$ | (a) | 3-furyl | $CH_3$ | $CH_3$ | $CH_3$ | H | H |
| 17 | 21-desethyl-21-cyclopropyl spinosyn A 17-pseudoaglycone | H | $CH_3$ | H | cyclopropyl | $CH_3$ | $CH_3$ | $CH_3$ | H | H |
| 18 | 21-desethyl-21-cyclopropyl spinosyn D 17-pseudoaglycone | $CH_3$ | $CH_3$ | H | cyclopropyl | $CH_3$ | $CH_3$ | $CH_3$ | H | H |
| 19 | 21-desethyl-21-cyclobutyl spinosyn A 17-pseudoaglycone | H | $CH_3$ | H | cyclobutyl | $CH_3$ | $CH_3$ | $CH_3$ | H | H |
| 20 | 21-desethyl-21-cyclobutyl spinosyn D pseudoaglycone | $CH_3$ | $CH_3$ | H | cyclobutyl | $CH_3$ | $CH_3$ | $CH_3$ | H | H |
| 21 | 16-desmethyl spinosyn D | $CH_3$ | H | (a) | ethyl | $CH_3$ | $CH_3$ | $CH_3$ | H | H |
| 22 | 16-desmethyl spinosyn D 17-pseudoaglycone | $CH_3$ | H | H | ethyl | $CH_3$ | $CH_3$ | $CH_3$ | H | H |
| 23 | 21-desethyl-21-n-propyl spinosyn A | H | $CH_3$ | (a) | n-propyl | $CH_3$ | $CH_3$ | $CH_3$ | H | H |
| 24 | 6-ethyl spinosyn A | $C_2H_5$ | $CH_3$ | (a) | ethyl | $CH_3$ | $CH_3$ | $CH_3$ | H | H |
| 25 | 6-ethyl-21-desethyl-21-n-propyl spinosyn A | $C_2H_5$ | $CH_3$ | (a) | n-propyl | $CH_3$ | $CH_3$ | $CH_3$ | H | H |
| 26 | 16-desmethyl-16-ethyl spinosyn A | H | $C_2H_5$ | (a) | ethyl | $CH_3$ | $CH_3$ | $CH_3$ | H | H |
| 27 | 16-desmethyl-16-ethyl spinosyn D | $CH_3$ | $C_2H_5$ | (a) | ethyl | $CH_3$ | $CH_3$ | $CH_3$ | H | H |
| 28 | 21-desethyl-21-n-propyl spinosyn D | $CH_3$ | $CH_3$ | (a) | n-propyl | $CH_3$ | $CH_3$ | $CH_3$ | H | H |
| 29 | 5,6-dihydro-21-desethyl-21-n-propyl spinosyn A | H | $CH_3$ | (a) | n-propyl | $CH_3$ | $CH_3$ | $CH_3$ | H | H |

The 5,6-dihydro derivatives of the compounds of Formula I (e.g. compound 8 in Table 3) are compounds of the Formula II:

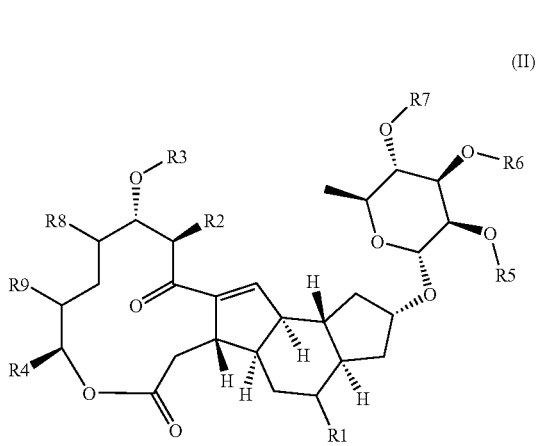

(II)

wherein R1, R2, R3, R4, R5, R6, R7, R8, and R9 are as defined for Formula I.

In another of its aspects, the invention provides a biologically pure culture of *Saccharopolyspora spinosa* selected from NRRL 30539,
NRRL 30540,
NRRL 30541, and
NRRL 30542.

In another of its aspects, the invention provides a method of controlling pests which comprises delivering to a pest an effective amount of a compound of claim 1.

In another of its aspects, the invention provides a pesticide composition comprising an effective amount of a compound of claim 1 as active ingredient in combination with an appropriate diluent or carrier.

BRIEF DESCRIPTION OF THE SEQUENCES

Figure 1:
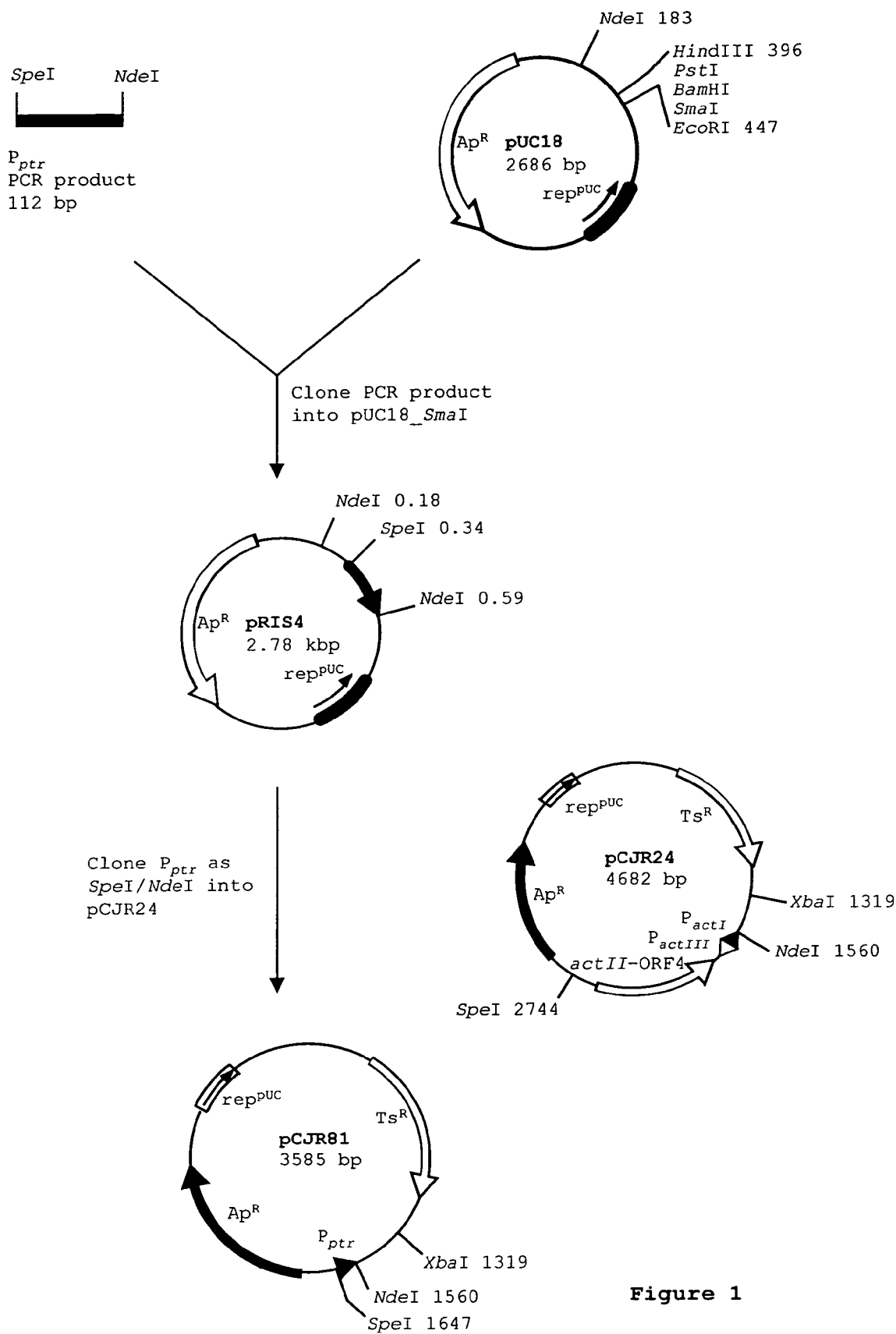
FIG. 1 shows the construction of pCJR81.

SEQ ID NO:1 is oligo PRIS1.
SEQ ID NO:2 is oligo PRIS2.
SEQ ID NO:3 is the DNA sequence of the promoter for resistance to pristinamycin.
SEQ ID NO:4 is oligo CR311.
SEQ ID NO:5 is oligo CR312.
SEQ ID NO:6 is oligo SP28.
SEQ ID NO:7 is oligo SP29.
SEQ ID NO:8 is the fragment of DNA encoding the ery PKS loading module which was used for cloning, with introduced restriction enzyme sites at bp 1-6 and bp 1680-1685.
SEQ ID NO:9 is oligo SP14.
SEQ ID NO:10 is oligo SP15.
SEQ ID NO:11 is the fragment of DNA encoding the ave PKS loading module which was used for cloning, with introduced restriction enzyme sites at bp 1-6 and bp 1689-1694.
SEQ ID NO:12 is oligo CR322.
SEQ ID NO:13 is oligo CR323.
SEQ ID NO:14 is oligo CR324.
SEQ ID NO:15 is oligo CR325.
SEQ ID NO:16 is oligo CR328.
SEQ ID NO:17 is oligo CR329.
SEQ ID NO:18 is oligo CR330.
SEQ ID NO:19 is oligo CR321.
SEQ ID NO:20 is the fragment of DNA encoding the rap AT2 which was used for cloning, with introduced restriction enzyme sites at bp 1-6 and bp 832-837.
SEQ ID NO:21 is oligo CCRMONF.
SEQ ID NO:22 is oligo CCRMONR.
SEQ ID NO:23 is the DNA sequence used for expression of the *Streptomyces cinnamonensis* crotonyl-CoA reductase, with introduced restriction sites at bp 1-6 and 1389-1394.
SEQ ID NO 24 is oligo AK1.
SEQ ID NO 25 is oligo AK2.
SEQ ID NO 26 is the fragment of DNA encoding the tyl AT5 which was used for cloning, with introduced restriction enzyme sites at bp 1-6 and bp 967-972.

DETAILED DESCRIPTION OF THE INVENTION

Culture Description

The novel strains derived from *Saccharopolyspora spinosa* NRRL 18537 or *Saccharopolyspora spinosa* NRRL 18538 and producing the compounds of the invention are identified in the table below. The cultures have been deposited in accordance with the terms of the Budapest treaty at the Midwest Area Regional Center, Agricultural Research Service, United States Department of Agriculture, 815 North University Street, Peoria, Ill. 61604. The strains were deposited on Jan. 15, 2001, and assigned the deposit numbers as detailed in Table 4 below.

TABLE 4

| Deposit Number | Strain | Parent Strain |
| --- | --- | --- |
| NRRL 30539 | *Saccharopolyspora spinosa* 7D23 | NRRL 18538 |
| NRRL 30540 | *Saccharopolyspora spinosa* 13E | NRRL 18537 |
| NRRL 30541 | *Saccharopolyspora spinosa* 21K2 | NRRL 18538 |
| NRRL 30542 | *Saccharopolyspora spinosa* 36P4 | NRRL 18538 |

Culture Characteristics

The novel strains derived from *Saccharopolyspora spinosa* NRRL 18537 or *Saccharopolyspora spinosa* NRRL 18538 and producing the compounds of the invention had the following culture characteristics:

All cultures grew well on ISP2 and Bennett's agar and aerial hyphae were produced on all media used. The aerial spore mass was predominately white (developing a pale pink hue with age). Substrate mycelium was cream to light tan in color, no distinctive pigment was apparent. A soluble brown pigment was released into the medium. No significant differences were observed on any of the media used.

Manipulation of Spinosyn Pathway and Accessory Genes

In order to facilitate the manipulation of the spinosyn biosynthetic pathway, cosmids pRHB9A6 and pRHB3E11 were obtained and are described in U.S. Pat. No. 6,274,350 B1 and Waldron et al. (2001).

It is not directly apparent from the sequence of the spinosyn biosynthetic genes how production of spinosyns is regulated. In order to avoid potential complications associated with regulation of the gene cluster, a number of heterologous promoters were used to drive all or part of the polyketide synthase portion (genes spnA, spnB, spnC, spnD and spnE). The following promoters were found to be at least as efficient in the production of spinosyn PKS as the natural promoter (judged by production of the final products spinosyn A, spinosyn D, spinosyn A C17-pseudoaglycone, and spinosyn D C17-pseudoaglycone): The actI promoter from the actinorhodin biosynthetic cluster of *S. coelicolor*, used along with its cognate activator, actII-ORF4, (as described in WO 98/01546, WO 98/01571, Rowe et al. 1998) and; The promoter for the resistance to pristinamycin. The latter has previously been reported to drive overexpression of polyketide genes from *S. erythraea* (Blanc et al. 1995; Sala-Bey et al. 1995). It is a promoter that can be induced by physiological stresses in *Streptomyces* spp. The use of heterologous promoters in *S. spinosa* is not limited to those described above, and could include others which might be expected to function in *S. spinosa*.

Hybrid Spinosyn PKS Using Heterologous Loading Module

In one of its aspects the invention provides hybrid PKSs that are functional in *Saccharopolyspora spinosa* to generate polyketides that are processed to biologically-active spinosyns. The resulting polyketides were extended to the same length as the natural spinosyns, and processed by cross-bridging and glycosylation to generate novel insecticidal spinosyns. Preferably the hybrid PKS comprises the extension modules from the spn PKS with a heterologous loading module that leads to a spinosyn polyketide having a different starter unit. Hybrid spinosyn PKS genes that contain the spn extender modules behind a heterologous loading module can provide novel spinosyns with different side chains at C21. The nature of this side chain is determined by the starter unit which the loading module selects to initiate polyketide synthesis. Changes in the side chain may alter the physical properties or biological activity of the resulting spinosyn. It is particularly useful to provide a hybrid PKS gene in which the loading module accepts many different carboxylic acids, including unnatural acids. Such a gene can be used to generate many different spinosyns by incorporation of different starter units. For example, the loading module of the spn PKS can be replaced by the loading module of the ave PKS, which is known to accept a wide variety of starter units (Dutton et al., 1991). The loading module of the ery PKS is also known to accept alternate starter units (Pacey et al., 1998). Thus, an organism expressing such hybrid spinosyn PKS genes can produce novel spinosyns in which the nature of the side chain at C21 is determined by the carboxylic acid that is fed to the organism. The side chains can be of different lengths, with branches or cycles, and/or contain heteroatoms.

More preferably, the hybrid PKS includes a loading module that accepts many different carboxylic acids so the hybrid gene assembly can be used to produce many different spinosyns. Particularly useful examples contain the spn extension modules with the loading module from the erythromycin (ery) PKS, or the loading module from the avermectin (ave) PKS.

a. Hybrid Spinosyn PKS Using ery Loading Module

The loading module of the erythromycin biosynthetic cluster (eryAT0ACP0) governs the introduction of propionyl-CoA into the starter of the erythromycin molecule. It has been shown previously that alternative starters can be incorporated into the erythromycin molecule by feeding free acids to the production medium (Pacey et al. 1998).

As shown in the following Examples, generation of a hybrid spnA gene in which the erythromycin loading module replaces the spinosyn loading module leads to a spinosyn PKS which can accept free acids into the starter unit. In the following illustrative Example, the erythromycin loading module was spliced to the beginning of the spinosyn KS1 just within the KS domain in the conserved region. New domain or module connections are preferably made at conserved DNA sequences within domains, or close to the edges thereof; however, an active polyketide synthase can alternatively be generated by engineering splice sites in the interdomain regions (WO 98/01546).

The ery load fragment was cloned in-frame with, and upstream of, a region of spnA to allow homologous recombination with the native spn PKS. Upstream of the ery load was either the actI promoter ($P_{actI}$) or the promoter for resistance to pristinamycin ($P_{ptr}$), giving rise to the plasmids pLSB61 and pLSB62 respectively. These plasmids are based on pKC1132 and are therefore apramycin-resistant. They also carry oriT for conjugal transfer of DNA into actinomycetes (Bierman et al. 1992, Matsushima et al. 1994). These constructs were transformed into *S. spinosa* NRRL 18537 by conjugation. Exconjugants were confirmed to contain the hybrid ery/spn PKS under the appropriate promoter by PCR amplification.

*S. spinosa* NRRL 18537:pLSB62 was designated *S. spinosa* 13E, and was used for analysis of spinosyn production.

As demonstrated in the following Examples, when cultured in production media, *S. spinosa* 13E produced mainly spinosyn A and spinosyn E, in approximately equal amounts. The total yield of spinosyns was estimated to be approximately 10-25% of the wild-type spinosyn A levels, which represented an increase in yield of spinosyn E of approximately 10-fold. This altered ratio of products may be a reflection of looser specificity of the ery loading module relative to the spn loading module, or a reflection of the different substrate supply in *S. spinosa* compared with *S. erythraea*, or a combination of both. Incorporation of acetate by the ery load has been observed in *S. erythraea* when the erythromycin pathway is up-regulated (Rowe et al. 1998). The increase in yield of spinosyn E in strain 13E over wild-type levels means that this would be a preferred strain for the production of spinosyn E.

A number of carboxylic acids were fed to *S. spinosa* 13E, leading to the production of novel spinosyn analogues with altered starter units. Among the novel spinosyns identified were 21-desethyl-21-cyclopropyl spinosyns A and D (by incorporation of cyclopropane carboxylic acid), 21-desethyl- 21-cyclobutyl spinosyns A and D (by incorporation of cyclobutane carboxylic acid) and 21-desethyl-21-methylthiomethyl spinosyns A and D (from methylthioacetic acid). The novel analogues showed reasonable chromatographic retention times, characteristic UV chromophores and MS fragmentation patterns, and the predicted structures were supported by accurate mass measurements. Structural assignments of the isolated 21-cyclopropyl and 21-cyclobutyl compounds were confirmed by full NMR characterization. Compounds isolated were active in insect control assays.

The use of strain *S. spinosa* 13E is not limited to the production of these compounds. It is expected that a number of other spinosyn analogues can be identified by feeding other acids, such as those used to produce novel erythromycins (Pacey et al. 1998).

EXAMPLE 1

Construction of pCJR81

See FIG. 1. Plasmid pCJR81 is a vector for expression of polyketide genes under the promoter for resistance to pristinamycin. It was constructed as follows:

Two overlapping oligos were designed to perform a PCR reaction in which they act both as primers and template. They were designed to introduce an NdeI restriction site incorporating the ATG start codon, such that genes can be cloned with optimal spacing from the ribosome binding site. A SpeI restriction site was incorporated to facilitate further cloning. The oligos are PRIS1 (SEQ ID NO:1) and PRIS2 (SEQ ID NO:2).

Amplification to obtain the promoter fragment was performed with Pwo thermostable DNA polymerase using the manufacturer's conditions. The 112 bp fragment was phosphorylated with T4 polynucleotide kinase, and cloned into commercially-available pUC 18 digested with SmaI and dephosphorylated. Plasmids containing inserts were sequenced. One plasmid containing the correct sequence was designated pRIS4.

The 94 bp insert from pRIS4 was excised as a SpeI/NdeI fragment (SEQ ID NO:3) and cloned into pCJR24 (WO 98/01546, WO 98/01571, Rowe et al. 1998) which had been previously digested with SpeI and NdeI. One correct plasmid was designated pCJR81.

EXAMPLE 2

Construction of Plasmids for Expression from *S. spinosa*

Figure 2:
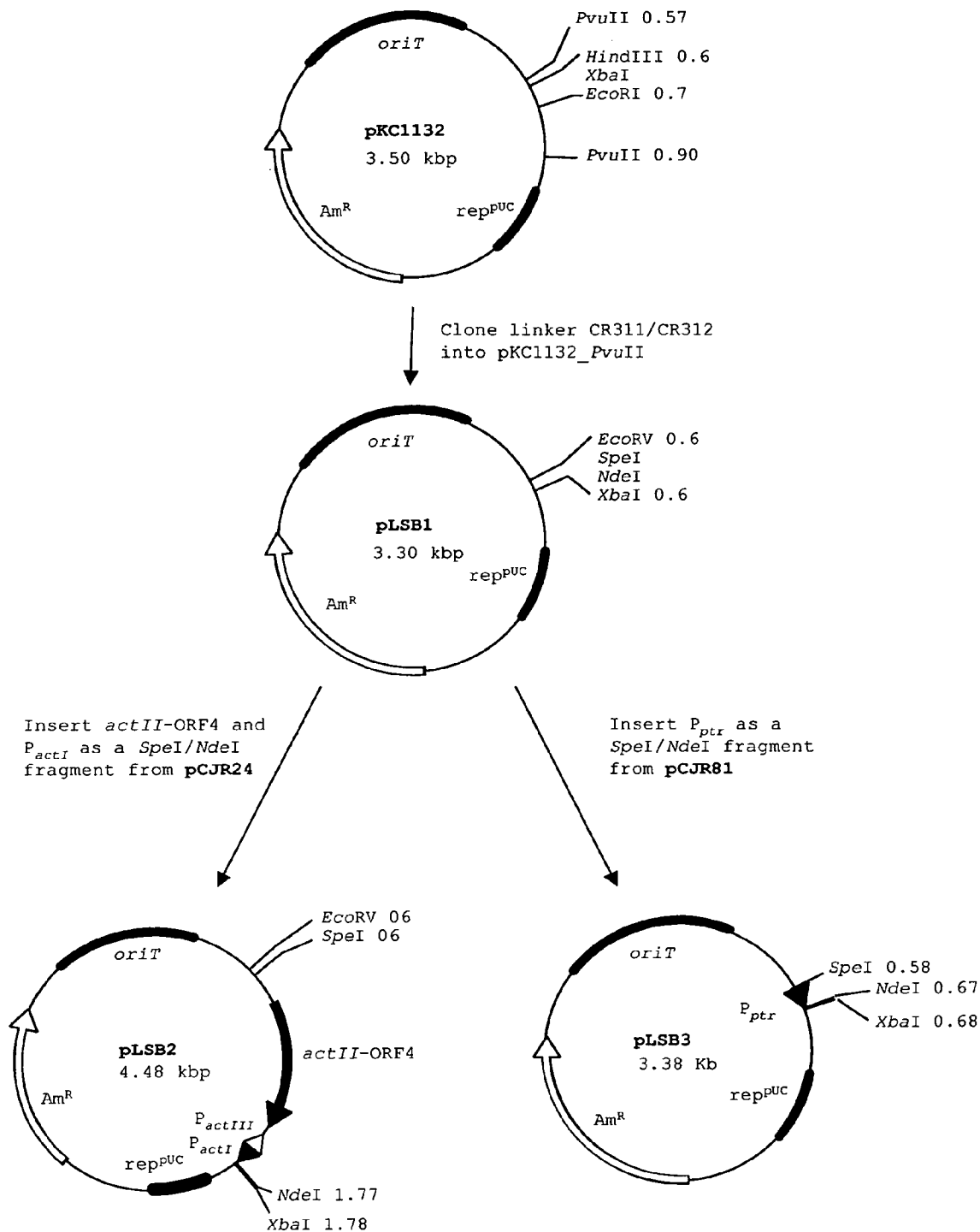
FIG. 2 shows the construction of vectors pLSB2 and pLSB3 used for expression of genes in *S. spinosa*.

See FIG. 2. Plasmids pLSB2 and pLSB3 were constructed for expression of polyketide genes or accessory genes in *S. spinosa*. Plasmid pLSB2 contains the acti promoter ($P_{actI}$) and its cognate activator, actII-ORF4. Plasmid pLSB3 contains the promoter for resistance to pristinamycin ($P_{ptr}$). These plasmids were constructed as follows:

Plasmid pKC1132 (Bierman et al. 1992) contains an origin of transfer (oriT), and an apramycin resistance marker for selection in both *E. coli* and actinomycetes. It can therefore be used for DNA manipulations in *E. coli*, and permit the final plasmids to be introduced into *S. spinosa* by conjugation. The polylinker of pKC1132 was replaced by a linker of two oligos CR311 (SEQ ID NO:4) and CR312 (SEQ ID NO:5) in order to provide appropriate EcoRV/SpeI/NdeI/XbaI restriction sites.

Plasmid pKC1132 was digested with PvuII and the ends dephosphorylated with shrimp alkaline phosphatase. The oligos CR311 and CR312 were phosphorylated with T4 polynucleotide kinase, annealed and cloned into pKC1132_PvuII to generate pLSB1. A SpeI/NdeI fragment containing the actinorhodin pathway specific activator, actII-ORF4 and the actI promoter was isolated from pCJR24 (WO 98/01546, WO 98/01571, Rowe et al. 1998) and a SpeI/NdeI fragment containing the promoter for resistance to pristinamycin was isolated from pCJR81 (described above, Example 1). Each of these fragments was cloned independently into pLSB1 digested with SpeI and NdeI to generate pLSB2 (containing actII-ORF4 and $P_{actI}$) and pLSB3 (containing $P_{ptr}$).

EXAMPLE 3

Figure 3:
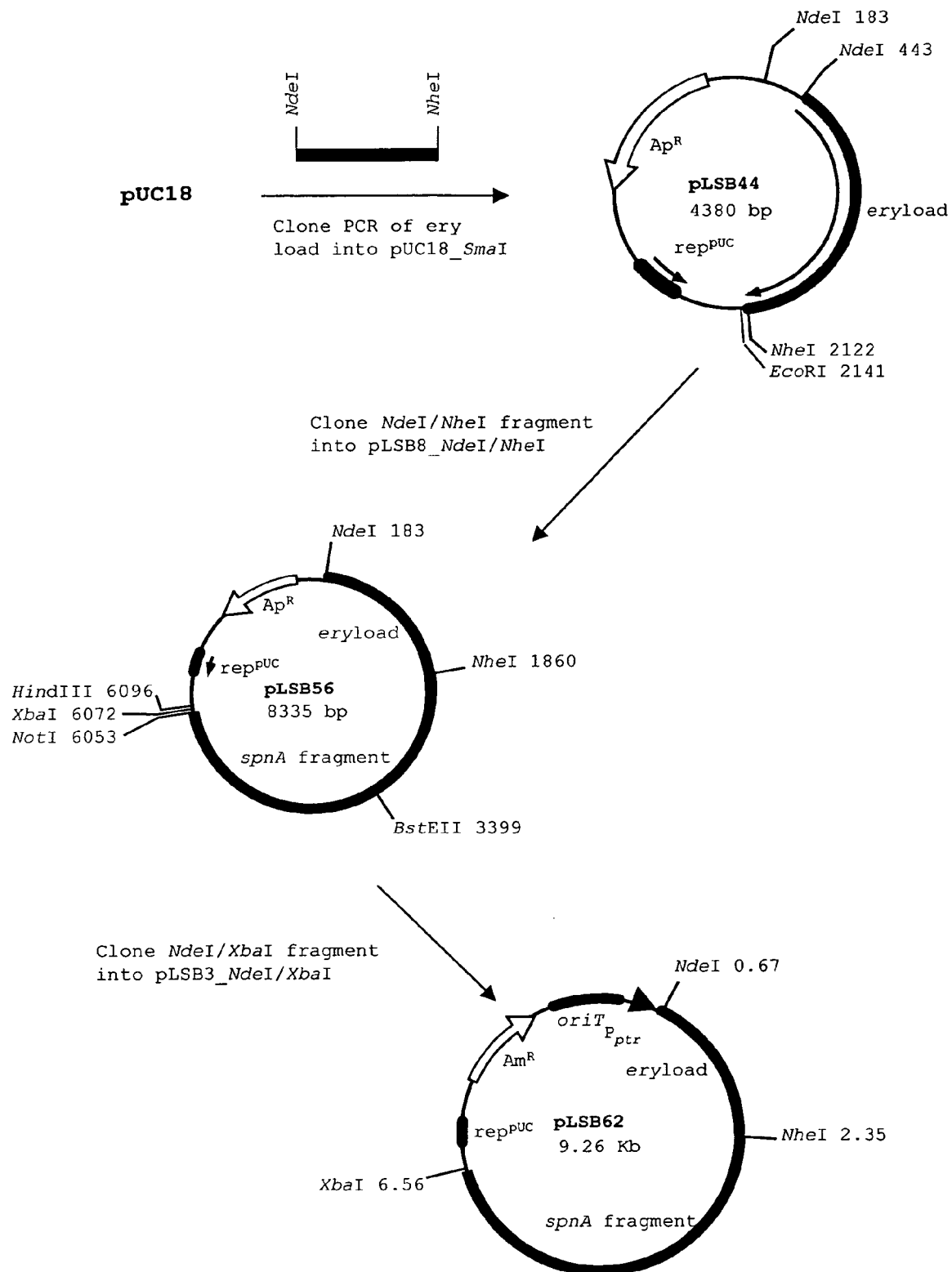
FIG. 3 shows the construction of pLSB62, a vector to introduce the ery load into the spinosyn pathway.

Construction of a Vector to Incorporate the Loading Module of the Erythromycin Polyketide Synthase into the Spinosyn Polyketide Synthase See FIG. 3. The vector to incorporate the loading module of the erythromycin polyketide synthase into the spinosyn polyketide synthase contains the erythromycin loading module (AT0ACP0), followed by a region of the first module of the spinosyn PKS to provide homology for integration. The vector is designated pLSB62 and was constructed as follows.

The erythromycin loading module was amplified by PCR using pCJR26 (Rowe et al. 1998) as the template, and oligos SP28 (SEQ ID NO:6) and SP29 (SEQ ID NO:7). SP28 incorporates an NdeI site at the start codon of the ery sequence, and SP29 incorporates an NheI site at the beginning of the KS1 domain.

The PCR fragment was phosphorylated, gel-purified and cloned into pUC18 which had been previously digested with SmaI and dephosphorylated. Clones were screened for the presence of inserts and sequenced. One clone containing the correct sequence was designated pLSB44. It contained the insert in the orientation with the NheI site close to the EcoRI site of the polylinker. The sequence of the erythromycin loading module fragment used, from the NdeI site to the NheI site is shown in SEQ ID NO 8.

Plasmid pLSB8 (described in Example 11) contains a fragment of spnA starting with the NheI site at spnKS 1. The fragment containing the erythromycin loading module was excised from pLSB44 as an NdeI/NheI fragment and cloned into pLSB8 previously digested with NdeI and NheI, to give pLSB56. The fragment contained in pLSB56 contains the erythromycin loading module spliced in-frame to the spinosyn KS1, with a region of homology to spnA which is sufficient for integration to occur.

This region was removed as an NdeI/XbaI fragment and cloned into pLSB3 to give pLSB62. This places the new ery/spn hybrid fragment under $P_{ptr}$, in a vector which can be transferred into *S. spinosa* by conjugation and selected using the apramycin resistance marker.

EXAMPLE 4

Figure 4:
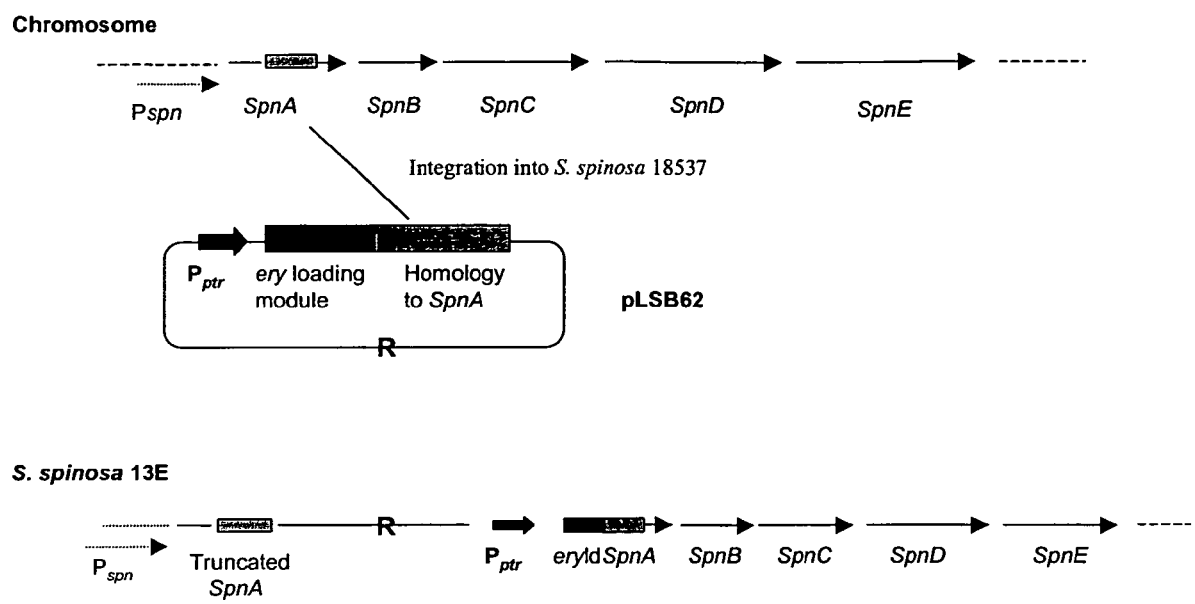
FIG. 4 shows the hybrid ery/spn PKS pathway of *S. spinosa* 13E.

Generation of a *S. spinosa* Strain Harbouring a Hybrid Polyketide Synthase Comprising the Erythromycin Loading Module Fused to the KS1 of the Spinosyn PKS See FIG. 4. *Saccharopolyspora spinosa* NRRL 18537 was transformed by conjugation (Matsushima et al. 1994) from *E. coli* S17-1 (Simon et al., 1983) with pLSB62. Transformants were selected for apramycin resistance and screened by PCR. A single transformant was designated strain *S. spinosa* 13E.

EXAMPLE 5

Chemical Analysis of *S. spinosa* Fermentations

The following HPLC method is useful for analyzing fermentations for the production of natural spinosyns and novel non-natural engineered spinosyns.

In a 2 mL Eppendorf tube, an aliquot of fermentation broth (1 mL) was adjusted to pH~10 by the addition of 20% ammonia solution (ca. 20 µl). Ethyl acetate (1 mL) was added to the sample and mixed vigorously for 60 seconds using a vortex. The mixture was separated by centrifugation in a microfuge and the upper phase removed to a clean 2 mL Eppendorf tube. The ethyl acetate was removed by evaporation using a Speedvac. Residues were dissolved into methanol (250 µl) and clarified using a microfuge. Analysis was by the following HPLC system:

Injection volume: 50 µl
Column stationary phase: 150×4.6 mm column, base-deactivated silica gel 3 µm (Hypersil $C_{18}$-BDS).
Mobile phase A: 10% acetonitrile:90% water, containing 10 mM ammonium acetate and 0.15% formic acid.
Mobile phase B: 90% acetonitrile:10% water, containing 10 mM ammonium acetate and 0.15% formic acid.
Mobile phase gradient: T=0 min, 10% B; T=1, 10% B; T=25, 95% B; T=29,95% B; T=29.5, 10% B.
Flow rate: 1 mL/min.
Detection: UV at 254 nm; MS over m/z range 100-1000.

EXAMPLE 6

Production of Metabolites by *S. spinosa* 13E Fermentation

*S. spinosa* 13E was cultured from a frozen vegetative stock (1:1 CSM culture:cryopreservative, where the cryopreservative is 10% lactose, 20% glycerol w/v in water). A primary pre-culture was grown in CSM medium (tryptic soy broth 30 g/l, yeast extract 3 g/l, magnesium sulfate 2 g/l, glucose 5 g/l, maltose 4 g/l; Hosted and Baltz 1996; U.S. Pat. No. 5,362,634), in a 50 mL culture in a 250 mL Erlenmeyer flask with a steel spring, shaken at 250 rpm with a two-inch throw at 30° C., 75% relative humidity for 3 days. This was used to inoculate a secondary pre-culture in vegetative medium (glucose 10 g/l, N-Z-amine A 30 g/l, yeast extract 3 g/l, magnesium sulfate 2 g/l; Strobel and Nakatsukasa 1993; U.S. Pat. No. 5,362,634) at 5% v/v, which was cultured under the same conditions for a further 2 days. The secondary vegetative pre-culture was used to inoculate production medium (glucose 67 g/l, Proflo cottonseed flour 25 g/l, peptonized milk nutrient 22 g/l, corn steep liquor 12 g/l, methyl oleate 40 g/l, calcium carbonate 5 g/l, pH to 7.0 with sodium hydroxide; Strobel and Nakatsukasa 1993) at 5% v/v. Small scale production cultures were fermented under the same conditions as the pre-cultures, but for 7-10 days. For initial *S. spinosa* 13E production, small-scale cultures were grown in 30 mL of production medium in 250 mL Erlenmeyer flasks with springs for 7 days.

For the identification of metabolites produced, a 1 mL aliquot of fermentation broth was analyzed by LC-MS as described in Example 5. By comparison to authentic standards, and to a fermentation extract from non-transformed strain *S. spinosa* NRRL 18537, the major compounds produced by *S. spinosa* 13E were identified as spinosyns A and E (which are produced in approximately equal amounts) and spinosyn D (which was observed as a minor product). The titer of strain *S. spinosa* 13E was ~10-15 mg/l of total spinosyns. The ratio of products for *S. spinosa* 13E was different to NRRL 18537, with the relative production of spinosyn E being significantly increased.

EXAMPLE 7

Precursor-Directed Production of Novel Spinosyns from *S. spinosa* 13E (Production of Compounds 1-6)

The ery/spn hybrid PKS was used to generate novel spinosyn metabolites by feeding carboxylic acids to production cultures. The ery loading module incorporated the carboxylic acid within the starter of the molecule.

Parallel production flasks (30 mL in 250 mL Erlenmeyer flask with spring) were inoculated as described in Example 6 above. After 24 h each of these was fed with a carboxylic acid (stock solutions made in water and pH adjusted to 6.5 with sodium hydroxide) at a final concentration of 2-6 mM. After 7 days a 1 mL aliquot of fermentation broth was analyzed by LC-MS as described in Example 5. The incorporation of cyclobutyl carboxylic acid, cyclopropyl carboxylic acid and methylthioacetic acid to generate novel C21 modified spinosyns was indicated by the appearance of novel peaks in the UV and MS chromatograms (Table 5). The MS spectra of the novel compounds gave ions for the $[M+H]^+$ species and for the forosamine fragment (142.3).

TABLE 5

| Carboxylic acid fed | Compound No. (see Table 3) | Retention time (min) | Key Mass Spectral data (m/z) |
|---|---|---|---|
| cyclopropyl carboxylic acid | 1 | 23.5 | 744.4 $[M + H]^+$; 142.4 |
| cyclopropyl carboxylic acid | 2 | 25.0 | 758.5 $[M + H]^+$; 142.3 |
| cyclobutyl carboxylic acid | 3 | 25.7 | 758.5 $[M + H]^+$; 142.3 |
| cyclobutyl carboxylic acid | 4 | 27.3 | 772.5 $[M + H]^+$; 142.2 |
| methylthio acetic acid | 5 | 22.9 | 764.4 $[M + H]^+$; 142.3 |
| methylthio acetic acid | 6 | 24.3 | 778.5 $[M + H]^+$; 142.3 |

EXAMPLE 8

Production and Isolation of 21-Desethyl-21-Cyclobutyl Spinosyns A and D (Compounds 3 and 4)

Frozen vegetative stocks of *S. spinosa* 13E were inoculated into primary vegetative pre-cultures in CSM (50 mL incubated in a 250 mL Erlenmeyer flask with spring). Secondary pre-cultures in vegetative medium (250 mL incubated in a 2 L Erlenmeyer flask with spring) were prepared and incubated as described in Example 6, but at 300 rpm with a one-inch throw.

Twelve to 14 L of production medium was prepared, as in Example 6, with the addition of 0.01% v/v Pluronic L-0101 (BASF) antifoam. Production medium was inoculated with the secondary vegetative pre-culture at 5% v/v, and allowed to ferment in a 20 L stirred bioreactor for 7-10 days at 30° C. Airflow was set at 0.75 vvm; over pressure was set at 0.5 barg or below, and impeller tip speed was controlled between 0.39 and 1.57 $ms^{-1}$ in order to maintain dissolved oxygen tension at or above 30% of air saturation. Additional Pluronic L0101 (BASF) was added to control foaming, if needed. Cyclobutyl carboxylic acid was fed to the bioreactor at 25 hours, to a final concentration of 5 mM. The fermentation broth was harvested after 7 days and clarified by centrifugation to provide supernatant and cells. The cells (1 L) were extracted by mixing thoroughly with an equal volume of methanol then allowed to stand for 30 min. The cell-methanol slurry was centrifuged, and the supernatant decanted off. The procedure was repeated. The fermentation supernatant (12 L) was adjusted to pH~10 by addition of 5 N NaOH and stirred gently with 0.75 volumes of ethyl acetate for 8 hours. The upper phase was removed by aspiration and the extraction repeated. The ethyl acetate and methanol fractions were combined and the solvents removed in vacuo to yield a yellow-brown oil/aqueous mixture (1 L). This was mixed with ethyl acetate (2 L) and extracted with a solution of 50 mM tartaric acid (3×1.5 L). The tartaric acid extracts were combined, adjusted to pH~10 with 5 N NaOH, and extracted with ethyl acetate (3×1.5 L). The ethyl acetate extracts were combined and the solvent removed in vacuo to leave a brown oily residue (7.5 g). The residue was dissolved into ethyl acetate (500 mL) and extracted three times with 50 mM tartaric acid (350 mL). The tartaric acid fractions were combined, adjusted to pH~10 and re-extracted with ethyl acetate (3×500 mL). The ethyl acetate fractions were combined and the solvent removed in vacuo to yield a brown oily residue (0.5 g).

The oily residue was dissolved into methanol (1.5 mL) and chromatographed, in two equal portions, over base-deactivated reversed-phase silica gel (Hypersil $C_{18}$-BDS, 5 µm; 21×250 mm) eluting with a mobile phase gradient as described below, at a flow rate of 21 mL/min.
Mobile phase gradient: T=0 min, 15% B; T=5, 35% B; T=35, 90% B; T=45, 95% B.
Mobile-phase A: 10% acetonitrile/90% water, containing 10 mM ammonium acetate and 0.15% formic acid.
Mobile-phase B: 90% acetonitrile/10% water, containing 10 mM ammonium acetate and 0.15% formic acid.

Fractions were collected every 30 seconds. Fractions from the initial fractionation that contained 21-desethyl-21-cyclobutyl spinosyn A were combined, and the solvent removed in vacuo. The residues were chromatographed over reversed-phase silica gel (Prodigy $C_{18}$, 5 µm; 10×250 mm) eluting with a gradient as described below, at a flow rate of 5 mL/min.
T=0, 55% B; T=5, 70% B; T=35,95% B; T=45, 95% B.

Fractions were collected every 30 seconds. Fractions containing the 21-desethyl-21-cyclobutyl spinosyn A were combined, the acetonitrile removed in vacuo, and the sample concentrated using $C_{18}$-BondElute cartridges (200 mg). The sample was applied under gravity, washed with water (10 mL) and eluted with methanol (2×10 mL), then the solvent removed in vacuo. Fractions from the initial crude fractionation that contained 21-desethyl-21-cyclobutyl spinosyn D were combined and the solvent removed in vacuo. The residues were chromatographed over reversed-phase silica gel (Prodigy $C_{18}$, 5 µm; 10×250 mm) eluting with a gradient as described below, at a flow rate of 5 mL/min.
T=0 min, 25% B; T=5, 55% B; T=35, 95% B; T=45, 95% B.

Fractions were collected every 30 seconds. Fractions containing the 21-desethyl-21-cyclobutyl spinosyn D were combined, the acetonitrile removed in vacuo, and the sample concentrated using $C_{18}$-BondElute cartridges (200 mg capacity). The sample was applied under gravity, washed with water (10 mL) and eluted with methanol (2×10 mL), and the solvent removed in vacuo.

The chemical structures of the new spinosyns were determined by spectroscopic methods, including nuclear magnetic resonance spectroscopy (NMR), mass spectrometry (MS), ultraviolet spectrometry (UV), coupled high performance liquid chromatography-mass spectrometry (HPLC-MS), and by comparison to the spectral data for the known compounds spinosyns A, D, E and F.

21-desethyl-21-cyclobutyl spinosyn A (Compound 3) has the following characteristics:
Isolated yield: 3.1 mg
Molecular weight: 757
Molecular formula: $C_{43}H_{67}NO_{10}$
UV (by diode array detection during HPLC-MS analysis): 245 nm
Electrospray MS: m/z for $[M+H]^+$=758.5; forosamine sugar fragment ion at m/z=142.2.
Accurate FT-ICR-MS: m/z for $[M+H]^+$=758.4830 (requires: 758.4838).
Table 6 shows the $^1H$ and $^{13}C$ NMR chemical shift data for 21-desethyl-21-cyclobutyl spinosyn A in $CDCl_3$.

TABLE 6

| Position | $^1H$ | $^{13}C$ |
|---|---|---|
| 1 | — | 172.8 |
| 2a | 2.43 | 33.8 |
| 2b | 3.12 | 33.8 |
| 3 | 3.01 | 47.5 |
| 4 | 3.54 | 41.7 |
| 5 | 5.80 | 128.7 |
| 6 | 5.88 | 129.3 |
| 7 | 2.17 | 41.1 |
| 8a | 1.37 | 36.2 |
| 8b | 1.92 | — |
| 9 | 4.31 | 76.0 |
| 10a | 1.33 | 37.3 |
| 10b | 2.26 | — |
| 11 | 0.91 | 46.0 |
| 12 | 2.88 | 49.4 |
| 13 | 6.76 | 147.5 |
| 14 | — | 144.2 |
| 15 | — | 202.9 |
| 16 | 3.26 | 47.8 |
| 16-Me | 1.17 | 16.1 |
| 17 | 3.61 | 80.6 |
| 18a | 1.49 | 34.4 |
| 18b | 1.49 | — |
| 19a | — | 21.7 |
| 19b | — | — |
| 20a | 1.34 | 28.2 |
| 20b | 1.44 | — |
| 21 | 4.80 | |
| 22 | 2.34 | |
| 23a | 1.65 | |
| 23b | 1.65 | |
| 24a | 1.76 | 17.8 |
| 24b | 1.76 | — |
| 25a | 1.86 | 24.6 |
| 25b | 1.86 | — |
| 1' | 4.85 | 95.4 |
| 2' | 3.49 | 77.7 |
| 3' | 3.46 | 81.0 |
| 4' | 3.12 | 82.2 |
| 5' | 3.54 | 67.9 |
| 6' | 1.28 | 17.8 |
| 2'-OMe | 3.49 | 59.0 |
| 3'-OMe | 3.50 | 57.7 |
| 4'-OMe | 3.56 | 60.9 |
| 1" | 4.42 | 103.4 |
| 2"a | 1.47 | 30.8 |
| 2"b | 1.98 | — |
| 3"a | 1.47 | 18.5 |
| 3"b | 1.98 | — |
| 4" | 2.26 | 64.8 |
| 5" | 3.84 | 73.5 |
| 6" | 1.26 | 19.0 |
| 4"-NMe$_2$ | 2.26 | 40.6 |

Chemical shifts referenced to the proton of $CHCl_3$ at 7.26 ppm 21-desethyl-21-cyclobutyl spinosyn D (Compound 4) had the following characteristics:
Isolated yield: ~1 mg
Molecular weight: 771
Molecular formula: $C_{44}H_{69}NO_{10}$
UV (by diode array detection during HPLC-MS analysis): 245 nm
Eletrospray MS: m/z for $[M+H]^+=772.5$; forosamine sugar fragment ion at m/z=142.2.
The small quantity of material precluded detailed NMR study of this molecule, but the data accumulated was consistent with the expected structure. This analysis was aided by comparison to the data for 21-desethyl-21-cyclobutyl spinosyn A.

EXAMPLE 9

Preparation of 5,6-dihydro-21-desethyl-21-cyclobutyl spinosyn A (Compound 8) and 5,6-dihydro-21-desethyl-21-n-propyl spinosyn A (Compound 29)

A solution of 21-desethyl-21-cyclobutyl spinosyn A (3.1 mg, 0.004 mmol) in 2 mL of toluene and 0.5 mL of ethanol was purged with a slow stream of nitrogen for 20 minutes, then 2 mg of chlorotris(triphenylphosphine) rhodium was added and the solution hydrogenated at 60° C. and 1 atm. for 16 hours. After cooling and removal of solvent, the residue was chromatographed using a 10 cm×2 cm silica gel column, eluting with 5×25 mL fractions of dichloromethane containing 0%, 2%, 3%, 4%, and 5% MeOH respectively. The product-containing fractions were combined and concentrated to give 2.1 mg of 5,6-dihydro-21-desethyl-21-cyclobutyl spinosyn A. MS M+760.

5,6-dihydro-21-desethyl-21-n-propyl spinosyn A (Compound 29) was prepared from 21-desethyl-21-n-propyl spinosyn A (Compound 23) using the same procedure.

EXAMPLE 10

Production and Isolation of 21-desethyl-21-cyclopropyl Spinosyns A and D (Compounds 1 and 2)

Frozen vegetative stocks of *S. spinosa* 13E were inoculated into primary vegetative pre-cultures in CSM (50 mL incubated in a 250 mL Erlenmeyer flask with spring). Secondary pre-cultures in vegetative medium (250 mL incubated in a 2 L Erlenmeyer flask with spring) were prepared and incubated as described in Example 8.

Fourteen liters of production medium were prepared, as in Example 6, with the addition of 0.01% v/v Pluronic L-0101 (BASF) antifoam. Production medium was inoculated with the secondary pre-culture at 5% v/v and allowed to ferment in a 20 L stirred bioreactor for 7-10 days under the conditions described in Example 8. Cyclopropyl carboxylic acid was fed to the bioreactor at 45 hours to a final concentration of 5 mM. The fermentation broth was harvested after 7 days and extracted as described in Example 8.

The oily residue was dissolved in methanol (1.5 mL) and initially crudely chromatographed as described in Example 8. Fractions from the initial separation that contained 21-desethyl-21-cyclopropyl spinosyn A were combined and the solvent removed in vacuo. The residues were chromatographed over reversed-phase silica gel (Prodigy $C_{18}$, 5 μM; 10×250 mm) eluting with a gradient as described below, at a flow rate of 5 mL/min.
T=0 min, 55% B; T=70% B; T=30, 95% B; T=35, 95% B.

Fractions were collected every 30 seconds. Fractions containing the 21-desethyl-21-cyclopropyl spinosyn A were combined, the acetonitrile removed in vacuo, and the sample concentrated using a $C_{18}$-BondElute cartridge (200 mg). The sample was applied under gravity, washed with water (10 mL) and eluted with methanol (2×10 mL), and then the solvent was removed in vacuo.

21-desethyl-21-cyclopropyl spinosyn A (Compound 1) has the following characteristics:
Isolated yield: ~1 mg
Molecular weight: 743
Molecular formula: $C_{42}H_{65}NO_{10}$
UV (by diode array detection during HPLC-MS analysis): 245 nm
Electrospray MS: m/z for $[M+H]^+=744.5$; forosamine sugar fragment ion at m/z=142.2.

Table 7 summarizes the $^1H$ and $^{13}C$ NMR spectral data for 21-desethyl-21-cyclopropyl spinosyn A in $CDCl_3$.

TABLE 7

| Position | $^1H$ | $^{13}C$ |
|---|---|---|
| 1 | — | — |
| 2a | 2.43 | 34.0 |
| 2b | 3.13 | — |
| 3 | 3.00 | 47.3 |
| 4 | 3.49 | 41.4 |
| 5 | 5.87 | 129.1 |
| 6 | 5.79 | 128.6 |
| 7 | 2.15 | — |
| 8a | 1.34 | 36.0 |
| 8b | 1.91 | — |
| 9 | 4.30 | 75.9 |
| 10a | 1.32 | 37.0 |
| 10b | 2.24 | — |
| 11 | 0.89 | 45.9 |
| 12 | 2.85 | 34.0 |
| 13 | 6.74 | 147.4 |
| 14 | — | — |
| 15 | — | — |
| 16 | 3.26 | 47.5 |
| 17 | 3.62 | 80.6 |
| 18a | 1.51 | 34.2 |
| 18b | 1.51 | — |
| 19a | 1.18 | 22.0 |
| 19b | 1.74 | — |
| 20a | 1.62 | 30.9 |
| 20b | 1.62 | — |
| 21 | 4.18 | 79.3 |
| 22 | 0.89 | 16.5 |
| 23a* | 0.44 | 2.3 |
| 23b* | 0.14 | — |
| 24a* | 0.44 | 3.7 |
| 24b* | 0.14 | — |
| 25 | 1.17 | 16.0 |
| 1' | 4.84 | 95.2 |
| 2' | 3.49 | 77.5 |
| 3' | 3.45 | 80.9 |
| 4' | 3.10 | 82.1 |
| 5' | 3.54 | 67.7 |
| 6' | 1.27 | 17.6 |
| 2'-OMe | 3.49 | 58.8 |
| 3'-OMe | 3.48 | 57.5 |
| 4'-OMe | 3.55 | 60.7 |
| 1" | 4.41 | 103.4 |
| 2"a | 1.47 | 30.8 |
| 2"b | 1.98 | — |
| 3"a | 1.45 | 18.2 |
| 3"b | 2.24 | — |
| 4" | 2.24 | 64.7 |
| 5" | 3.48 | 73.4 |
| 6" | 1.27 | 18.7 |
| 4"-$NMe_2$ | 2.24 | 40.6 |

Chemical shifts referenced to the proton of $CHCl_3$ at 7.26 ppm.
*These assignments are interchangeable.

21-desethyl-21-cyclopropyl spinosyn D (Compound 2) has the following characteristics:
Isolated yield: ~0.5 mg
Molecular weight: 757
Molecular formula: $C_{43}H_{67}NO_{10}$
UV (by diode array detection during HPLC-MS analysis): 245 nm
Electrospray MS: m/z for $[M+H]^+=758.5$; forosamine sugar fragment ion at m/z=142.2.
The small quantity of material precluded the detailed NMR study of this molecule, but the data accumulated was consistent with the expected structure. This analysis was aided by comparison to the data for 21-desethyl-21-cyclopropyl spinosyn A.

b. Hybrid Spinosyn PKS Using ave Loading Domain

The loading module of the avermectin biosynthetic cluster (aveAT0ACP0) governs the introduction of C-2 branched starter units into the avermectin molecule, derived from iso-butyryl-CoA and 2-methylbutyryl-CoA. There is precedent for the swapping of this loading domain into the erythromycin PKS pathway to give novel polyketides with the starter unit specificity of the avermectin system (WO 98/01546, WO 98/01571, Marsden et al. 1998). The avermectin loading module has also been shown to incorporate CoA-esters of a broad range of free acids from the production medium, either in its native environment, or as part of the ave/ery hybrid pathway (Pacey et al. 1998). The avermectin loading module swap described in the literature is actually a replacement of the erythromycin AT0ACP0 by the avermectin AT0ACP0. This leads to a piece of erythromycin DNA sequence upstream of the avermectin AT0 between the start codon and a SpeI site. This was included in the ave/ery experiment because the N-terminal region (upstream of the homologous AT domain) is much larger in the erythromycin loading module than in that of avermectin, and may be important for stability of the protein. Because the resulting hybrid had been productive, the same region was used for the ave/spn hybrid. In effect, the resulting hybrid gene is an ery/ave/spn hybrid, but since it transfers the specificity of the avermectin loading module to the spinosyn PKS, it has been designated an ave/spn hybrid through-out.

The avermectin loading module (AT0ACP0) was cloned from pIG1 (WO 98/01546, WO 98/01571, Marsden et al. 1998) in-frame and upstream of the spnKS1, under the control of either $P_{actI}$, or $P_{ptr}$. The same splice site, at the beginning edge of the KS1 homologous region, was used as for the ery load experiment described above. A region of homology for integration was incorporated from pRHB3E11. The resulting plasmids, pLSB29 (with the hybrid PKS region under the control of $P_{actI}$) and pLSB30 (with the hybrid PKS region under the control of $P_{ptr}$) are based on pKC 1132 and therefore contain the apramycin resistance marker for selection both in *E. coli* and *S. spinosa*, and the oriT for conjugal transfer of DNA from *E. coli* to *S. spinosa* (Bierman et al. 1992, Matsushima et al. 1994). These constructs were transformed into *S. spinosa* NRRL 18538 by conjugation. Exconjugants were confirmed to contain the hybrid ave/spn PKS gene under the appropriate promoter by PCR analysis.

*S. spinosa* NRRL 18538:pLSB29 was designated *S. spinosa* 21 K2. It produced mainly spinosyns E, A and D by incorporation of acetate and propionate into the loading module. Additional small peaks were observed in LC-MS, with masses that were consistent with the novel natural products 21-desethyl-21-iso-propyl spinosyn A and 21-desethyl-21-sec-butyl spinosyn A and the equivalent D analogues. These minor products resulted from incorporation of iso-butyrate and 2-methyl butyrate respectively into the starter. In avermectin biosynthesis itself, the ave loading module recruits only these branched starters. However, a broader spectrum of products was observed when the ave loading module was spliced upstream of the KS1 in the erythromycin PKS, indicating that such a hybrid can incorporate acetate and propionate as well. We therefore observed the expected range of products from this engineered *S. spinosa* strain.

The structure of isolated 21-desethyl-21-iso-propyl spinosyn A was confirmed by NMR characterization. 21-desethyl-21-n-propyl spinosyn A was isolated as a minor component from the production culture of 21-desethyl-21-iso-propyl spinosyn A. The 21-n-propyl analogue, presumably made by the loading module taking butyrate from the medium, was also fully characterized. Both were active in insect control assays.

Some of the natural versatility of the loading module of the avermectin PKS had previously been transferred to the erythromycin system, so a broad range of free acids was fed to *S. spinosa* 21K2 to generate spinosyns with altered starter units. Novel spinosyn compounds were identified on the basis of UV chromophore, mass and mass spectral fragmentation, along with the knowledge of which acid was fed and therefore which compounds were expected from each experiment. To confirm the structure predictions made, a number of spinosyn analogues with novel C21 starter groups were isolated and fully characterized.

Free acids which can be used in this way include, but are not limited to, the following: Cyclic organic acids including cyclopropyl, cyclobutyl, cyclopentyl, cyclohexyl, cyclohexenyl and 2-methylcyclopropyl; heteroatom containing cyclic organic acids including 2-furoic acid, 3-furoic acid, thiophene carboxylic acid and methyl thiophene carboxylic acid; branched chain carboxylic acids; and some other acids which included methylthioacetic acid, chloroacetic acid, cyanoacetic acid and methoxyacetic acid.

Such feeding experiments lead to analogues of spinosyns (a spinosyn being a macrolide with a 22-membered tetracyclic nucleus of the type illustrated in Tables 1 and 2 and in Formula I) in which C21 bears a side chain other than ethyl, generally an alpha-branched C2-C5 alkyl group, a C3-C8 cycloalkyl or cycloalkenyl group (optionally substituted e.g. with one or more hydroxy, C1-4 alkyl or alkoxy groups or halogen atoms), or a 3-6 membered heterocycle containing O or S, saturated or fully or partially unsaturated, optionally substituted (as for cycloalkyl). Preferred candidates for the C21 substituent are the groups of carboxylate units useable as substrates by the ery or ave loading modules. Preferred substrates include cyclobutane carboxylic acid and cyclopropane carboxylic acid. Other possibilities include n-butyric acid, iso-propyl carboxylic acid, 2-(S)-methylbutyric acid, 2-methylcyclopropane carboxylic acid, 3-furoic acid and methylthioacetic acid.

Feeding the branched chain acids iso-propyl and 2-methyl butyl carboxylic acid did not alter the yield of novel natural products made due to the normal specificity of the ave load. These products were observed in all healthy cultures of *S. spinosa* 21K2 in low yield.

Cyclobutyl carboxylic acid was accepted by the ave loading module to give the A and D analogues, and a substantial proportion of the C17-pseudoaglycone of the A analogue. The cyclobutyl products were observed at higher levels than in the fed hybrid ery/spn system, with 21-desethyl-21-cyclobutyl spinosyn A at ~5-10 mg/liter, 21-desethyl-21-cyclobutyl spinosyn D at lower but significant levels and 21-desethyl-21-cyclobutyl spinosyn A 17-pseudoaglycone at ~10-15 mg/liter. The cyclopropyl carboxylic acid feed was also successful, yielding 21-desethyl-21-cyclopropyl spinosyns A and D. The two cyclobutyl analogues and the cyclopropyl A analogue were shown to be identical to the purified compounds isolated from the ery load experiment.

Methylthioacetic acid was incorporated to give the 21-desethyl-21-methylthiomethyl spinosyn A, at yields comparable to those of the cyclobutyl experiment above. This was a significant improvement in yield over production of the same compound from the ery load experiment. 2-furoic acid and methylcyclopropyl carboxylic acid were also incorporated to give the expected novel products.

EXAMPLE 11

Figure 5:
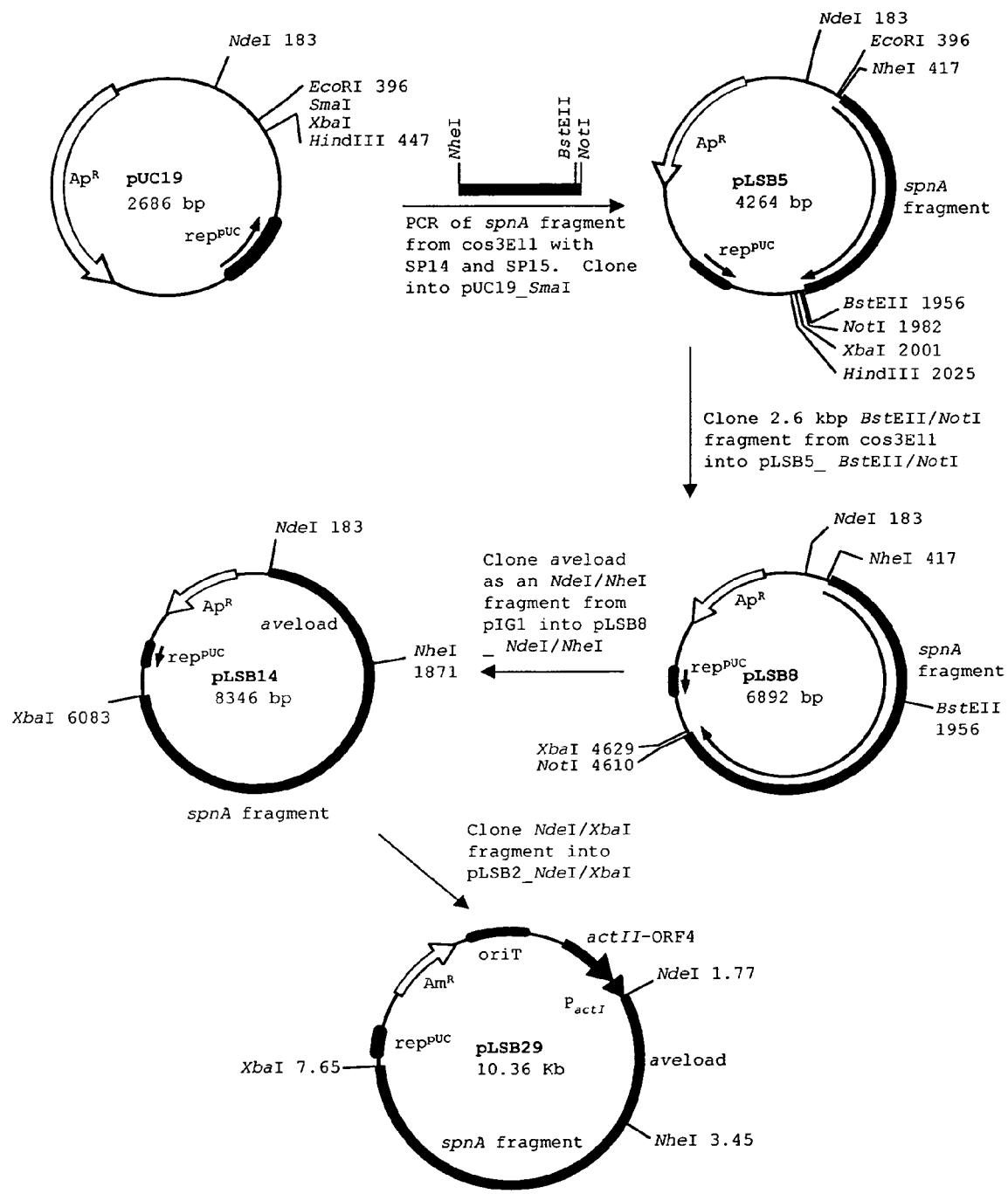
FIG. 5 shows the construction of pLSB29, a vector to introduce the ave load into the spinosyn pathway.

Construction of a Vector to Incorporate the Loading Module of the Avermectin Polyketide Synthase into the Spinosyn Polyketide Synthase See FIG. 5. The vector to incorporate the loading module of the avermectin polyketide synthase into the spinosyn polyketide synthase contains the avermectin loading module (AT0ACP0) followed by a region of the first module of the spinosyn PKS to provide homology for integration. The vector is designated pLSB29 and was constructed as follows:

The avermectin loading module has been previously spliced upstream of the erythromycin module 1 (WO 98/01546, WO 98/01571, Marsden et al. 1998). In this ave/ery hybrid the loading module had the DNA coding for the ery amino acid sequence at the start, followed by the AT0ACP0 of the ave PKS. This hybrid fragment conferred the specificity of the avermectin loading domain, although it included a small amount of ery sequence. The same fragment was used in this experiment, and leads to an ery/ave/spn hybrid protein. We describe it simply as an ave/spn hybrid since it is the specificity of the avermectin loading domain that is conferred on the spinosyn pathway. The fragment begins with an NdeI site incorporating the start codon, and ends with a NheI site engineered at the beginning of the KS1. This introduces a conservative amino acid change (Ile-Leu) in the spinosyn KS1 sequence.

To introduce the NheI site, the region of spnA from the beginning of the KS1 was amplified by PCR using pRHB3E11 (U.S. Pat. No. 6,274,350 B1, Waldron et al. 2001) as the template, and oligos SP14 (SEQ ID NO:9) and SP15 (SEQ ID NO:10). SP14 introduces an NheI site at bases 24107-24112 (numbers refer to SEQ ID NO:1 of U.S. Pat. No. 6,274,350). SP15 binds approximately 1500 bp downstream, at a BstEII site (25646-25652). A NotI site was also incorporated into SP15 for the subsequent cloning step. The PCR was carried out using Pwo thermostable polymerase under standard conditions.

The PCR product was phosphorylated, gel-purified and cloned into pUC19 which had been previously digested with SmaI and dephosphorylated. A number of insert-containing clones were sequenced. One clone containing the insert in the orientation which places the NheI site next to the EcoRI site in the vector was designated pLSB5.

To provide a large enough region of homology for integration, a fragment of approximately 2.6 kbp (from BstEII to NotI) was cloned out of pRHB3E11 into pLSB5, to yield pLSB8.

The avermectin loading module was then cloned from pIG1 (WO 98/01546, WO 98/01571, Marsden et al. 1998) as an NdeI/NheI fragment and ligated into pLSB8 previously digested with NdeI and NheI. The DNA sequence of the avermectin loading module fragment used, from the NdeI site to the NheI site is shown in SEQ ID NO 11. The resulting plasmid was designated pLSB14.

The fragment contained in pLSB14 contains the avermectin loading module spliced in-frame to the spinosyn KS1, with a region of homology to spnA which is sufficient for integration to occur.

This fragment was then removed as an NdeI/XbaI fragment and cloned into pLSB2 to give pLSB29. This places the new ave/spn hybrid fragment under PactI, in a vector which can be transferred into *S. spinosa* by conjugation and then selected using the apramycin resistance marker.

EXAMPLE 12

Figure 6:
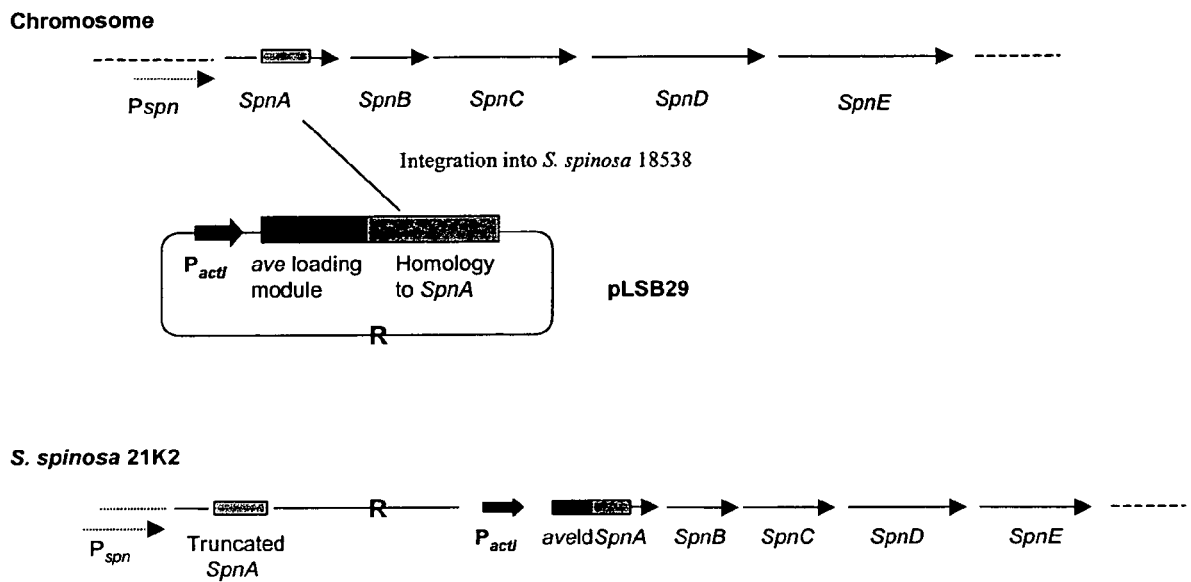
FIG. 6 shows the hybrid ave/spn PKS pathway of *S. spinosa* 21K2

Generation of a *S. spinosa* Strain Harbouring a Hybrid Polyketide Synthase Comprising the Avermectin Loading Module Fused to the KS 1 of the Spinosyn PKS See FIG. 6. *Saccharopolyspora spinosa* NRRL 18538 was transformed by conjugation (Matsushima et al. 1994) from *E. coli* S17-1 (Simon et al., 1983) with pLSB29. Transformants were selected by resistance to apramycin and screened by Southern blot analysis. A single transformant displaying the correct hybridization pattern to show that the plasmid had integrated into the chromosome by homologous recombination was designated strain *S. spinosa* 21K2.

EXAMPLE 13

Production of Metabolites by *S. spinosa* 21K2 Fermentation (Production of Compounds 9-12)

*S. spinosa* 21K2 was cultured from a frozen vegetative stock used to inoculate CSM medium (Hosted and Baltz 1996; U.S. Pat. No. 5,362,634). This pre-culture was grown in flasks shaken at 300 rpm with a one-inch throw at a temperature of 30° C. for 3 days. This was used to inoculate vegetative medium (Strobel and Nakatsukasa 1993; U.S. Pat. No. 5,362,634) at 5% v/v and was cultured under the same conditions for a further 2 days. The vegetative culture was used to inoculate production medium (Strobel and Nakatsukasa 1993) at 5% v/v. Small-scale production cultures were fermented under the same conditions as the pre-cultures, but for 7-10 days at 250 rpm with a two-inch throw and at 75% relative humidity. Initial small-scale production cultures were grown in 6 mL of production medium in 25 mL Erlenmeyer flasks with springs for 7 days.

To identify the metabolites produced, a 1 mL aliquot of fermentation broth was analyzed by LC-MS as described in Example 5. By comparison to authentic standards, and to a fermentation extract from strain *S. spinosa* NRRL 18538, the major compounds produced by *S. spinosa* 21K2 were spinosyns A, D and E. Spinosyn A was the major component produced, and the total yield of spinosyns was ~50 mg/l.

In addition to the known spinosyns A, D and E, four new compounds were clearly present. The chromatographic retention time and mass spectral data for these new compounds (Table 8) were consistent with their synthesis through the incorporation of branched chain starter units (iso-propyl carboxylic acid and 2-methylbutyric acid). The MS spectra of the new compounds gave ions for the [M+H]$^+$ species and for the forosamine fragment (142.3).

The compounds derived from an iso-propyl carboxylic acid feed were present 2-3× higher levels than those derived from 2-methylbutyric acid. The new compounds comprised no more than 5% of the total spinosyns present.

TABLE 8

| Carboxylic acid starter unit | Compound No. (see Table 3) | Retention time (min) | Key mass spectral data (m/z) |
|---|---|---|---|
| iso-propyl carboxylic acid | 9 | 25.1 | 746.5 [M + H]+; 142.3 |
| iso-propyl carboxylic acid | 10 | 26.3 | 760.5 [M + H]+; 142.3 |
| 2-methylbutyric acid | 11 | 26.7 | 760.4 [M + H]+; 142.3 |
| 2-methylbutyric acid | 12 | 27.5 | 774.5 [M + H]+; 142.3 |

EXAMPLE 14

Precursor-Directed Production of Novel Spinosyns from S. spinosa 21K2 (Production of Compounds 1-6 and 13-20)

The ave/spn hybrid PKS was used to generate novel spinosyn metabolites by feeding carboxylic acids to production cultures. The avermectin loading module incorporated the carboxylic acid within the starter of the molecule.

Parallel 6 mL production flasks were inoculated as described in Example 13 above. After 24 h each of these was fed with a carboxylic acid (stock solutions made in water and pH adjusted to 6.5 with sodium hydroxide) at a final concentration of 3 mM. After 7 days a 1 mL aliquot of fermentation broth was analyzed by LC-MS as described in Examples 6 and 12. The incorporation of cyclobutyl carboxylic acid, cyclopropyl carboxylic acid, 2-methylcyclopropyl carboxylic acid, methylthio acetic acid and 3-furoic acid provided novel C21-modified spinosyns, as indicated by the appearance of new peaks in the UV and MS chromatograms (Table 9). The mass spectra of the novel compounds gave ions for the [M+H]+ species and for the forosamine fragment (142.3). In addition the feeding of cyclobutyl- and cyclopropyl carboxylic acids also caused significant accumulation of the corresponding 17-pseudoaglycones.

TABLE 9

| Carboxylic acid fed | Compound No. (see Table 3) | Retention time (min) | Key mass spectral data (m/z) |
|---|---|---|---|
| cyclobutyl CA | 2 | 25.7 | 758.4 [M + H]+; 142.4 |
| cyclobutyl CA | 3 | 27.2 | 772.5 [M + H]+; 142.4 |
| cyclopropyl CA | 1 | 23.5 | 744.5 [M + H]+; 142.4 |
| cyclopropyl CA | 2 | 25.1 | 758.5 [M + H]+; 142.4 |
| 2-methyl cyclopropyl CA | 13 | 25.7 | 758.5 [M + H]+; 142.4 |
| 2-methyl cyclopropyl CA | 14 | 26.9 | 772.5 [M + H]+; 142.4 |
| methylthio acetic acid | 5 | 22.9 | 764.5 [M + H]+; 142.4 |
| methylthio acetic acid | 6 | 24.4 | 778.4 [M + H]+; 142.4 |
| 3-furoic acid | 15 | 22.9 | 770.5 [M + H]+; 142.4 |
| 3-furoic acid | 16 | 24.3 | 784.5 [M + H]+; 142.4 |
| cyclobutyl CA | 19 | 27.1 | 639.4 [M + Na]+ |
| cyclobutyl CA | 20 | 28.6 | 653.4 [M + Na]+ |

The 21-cyclobutyl and cyclopropyl compounds were confirmed as the correct structures in comparison to the compounds isolated from feeding the ery load strain, S. spinosa 13E.

EXAMPLE 15

Isolation of Novel Metabolites from a Large-Scale Fermentation of S. spinosa 21K2

Frozen vegetative stocks of S. spinosa 21K2 were inoculated into primary vegetative pre-cultures of S. spinosa 21K2 in CSM (50 mL incubated in a 250 mL Erlenmeyer flask with spring). Secondary pre-cultures in vegetative medium (250 mL incubated in a 2 L Erlenmeyer flask with spring) were prepared and incubated as described in Example 6.

Fourteen liters of production medium were prepared, as in Example 6, with the addition of 0.01% v/v Pluronic L-0101 (BASF) antifoam. Production medium was inoculated with the secondary pre-culture at 5% v/v and allowed to ferment in a 20 L stirred bioreactor for 7-10 days under the conditions described in Example 8. 2-Methyl butyric acid, to a final concentration of 2 mM, was fed to the bioreactor at 26 and 37.5 hours, leading to an overall final concentration of 4 mM. The fermentation broth was harvested after 7 days and extracted as described in Example 8.

The oily residue was dissolved in methanol (1.5 mL) and initially chromatographed as described in Example 8. Fractions from the initial separation that contained 21-desethyl-21-iso-propyl spinosyn A were combined and the solvent removed in vacuo. The residues were chromatographed over reversed-phase silica gel (Prodigy $C_{18}$, 5 µm; 10×250 mm) eluting with a gradient as described below, at a flow rate of 5 mL/min.

T=0, 55% B; T=5, 70% B; T=35, 95% B; T=45, 95% B.

Fractions were collected every 30 seconds. Fractions containing the 21-desethyl-21-iso-propyl spinosyn A were combined, the acetonitrile removed in vacuo, and the sample concentrated using $C_{18}$-BondElute cartridges (200 mg). The sample was applied under gravity, washed with water (10 mL) and eluted with methanol (2×10 mL), then the solvent was removed in vacuo.

The dried sample was dissolved in methanol (0.5 mL) and chromatographed over reversed-phase base-deactivated silica gel (hypersil-C18-BDS; 4.6×250 mm; 5 µm). The column was eluted isocratically at a flow rate of 1 mL/min with ammonium acetate (10 mM)—methanol—tetrahydrofuran (40:45:15), and the three major components were collected after UV detection (244 nm). Under these conditions, retention times were as follows: spinosyn-D: 64.4 min., 21-desethyl-21-iso-propyl spinosyn A: 67.8 mins and 21-desethyl-21-n-propyl spinosyn A: 75.3 min. Each sample was dried in vacuo to give a white solid, which was identified by its NMR and mass spectra.

21-desethyl-21-n-propyl spinosyn A (Compound 23) has the following characteristics.

Molecular Weight: 745

Molecular formula: $C_{42}H_{67}NO_{10}$

UV (by diode array detection during HPLC analysis): 244 nm

Electrospray MS: m/z for [M+H]+=746.5; forosamine sugar fragment ion at m/z=142.2.

Table 10 summarizes the $^1H$ and $^{13}C$ NMR chemical shift data for 21-desethyl-21-n-propyl spinosyn A in $CDCl_3$.

TABLE 10

| Position | $^1$H | $^{13}$C |
|---|---|---|
| 1 | — | 172.5 |
| 2a | 3.13 | 34.1 |
| 2b | 2.42 | — |
| 3 | 3.03 | 47.5 |
| 4 | 3.50 | 41.5 |
| 5 | 5.81 | 128.8 |
| 6 | 5.89 | 129.3 |
| 7 | 2.19 | 41.1 |
| 8a | 1.94 | 36.2 |
| 8b | 1.35 | — |
| 9 | 4.32 | 76.0 |
| 10a | 2.29 | 37.3 |
| 10b | 1.35 | — |
| 11 | 0.92 | 45.9 |
| 12 | 2.88 | 49.4 |
| 13 | 6.78 | 144.1 |
| 14 | — | 147.5 |
| 15 | — | 202.9 |
| 16 | 3.30 | 47.6 |
| 16-Me | 1.20 | 16.2 |
| 17 | 3.65 | 80.6 |
| 18 | 1.55 | 34.3 |
| 18b | 1.55 | — |
| 19a | 1.78 | 21.6 |
| 19b | 1.21 | — |
| 20a | 1.56 | 30.7 |
| 20b | 1.50 | — |
| 21 | 4.77 | 75.3 |
| 22a | 1.50 | 37.8 |
| 22b | 1.39 | — |
| 23 | 1.28 | 18.3 |
| 24 | 0.99 | 14.0 |
| 1' | 4.88 | 95.4 |
| 2' | 3.51 | 77.7 |
| 3' | 3.49 | 81.0 |
| 4' | 3.13 | 82.2 |
| 5' | 3.56 | 67.9 |
| 6' | 1.30 | 19.0 |
| 2'-OMe | 3.51 | 59.0 |
| 3'-OMe | 3.51 | 57.7 |
| 4'-OMe | 3.57 | 60.9 |
| 1" | 4.43 | 103.5 |
| 2"a | 1.99 | 30.9 |
| 2"b | 1.49 | — |
| 3"a | 1.38 | 18.5 |
| 3"b | 1.50 | — |
| 4" | 2.25 | 64.8 |
| 5" | 3.49 | 73.5 |
| 6" | 1.28 | 17.8 |
| 4"-NMe$_2$ | 2.26 | 40.6 |

Chemical shifts referenced to the proton of CHCl$_3$ at 7.26 ppm 21-desethyl-21-iso-propyl spinosyn A (Compound 9) has the following characteristics.
Molecular Weight: 745
Molecular formula: C$_{42}$H$_{67}$NO$_{10}$
UV (by diode array detection during HPLC analysis): 244 nm
Electrospray MS: m/z for [M+H]+=746.5; forosamine sugar fragment ion at m/z=142.2.
Table 11 summarizes the $^1$H and $^{13}$C NMR chemical shift data for 21-desethyl-21-iso-propyl spinosyn A in CDCl$_3$.

TABLE 11

| Position | $^1$H | $^{13}$C |
|---|---|---|
| 1 | — | 173 |
| 2a | 3.15 | 34 |
| 2b | 2.43 | — |
| 3 | 3.03 | 48 |
| 4 | 3.55 | 42 |
| 5 | 5.82 | 129 |
| 6 | 5.90 | 129 |
| 7 | 2.19 | 42 |
| 8a | 1.94 | 36 |
| 8b | 1.35 | — |
| 9 | 4.32 | 76 |
| 10a | 2.28 | 37 |
| 10b | 1.38 | — |
| 11 | 0.93 | 46 |
| 12 | 2.90 | 50 |
| 13 | 6.78 | 144 |
| 14 | — | 147 |
| 15 | — | 204 |
| 16 | 3.28 | 48 |
| 16-Me | 1.19 | 16 |
| 17 | 3.63 | 81 |
| 18 | 1.52 | 35 |
| 18b | 1.52 | — |
| 19a | 1.80 | 22 |
| 19b | 1.19 | — |
| 20a | 1.52 | 27 |
| 20b | 1.52 | — |
| 21 | 4.66 | 80 |
| 22 | 1.80 | 33 |
| 23 | 0.85 | 18 |
| 22-Me | 0.83 | 18 |
| 1' | 4.87 | 96 |
| 2' | 3.51 | 78 |
| 3' | 3.47 | 81 |
| 4' | 3.13 | 82 |
| 5' | 3.56 | 68 |
| 6' | 1.30 | 19 |
| 2'-OMe | 3.51 | 59 |
| 3'-OMe | 3.51 | 58 |
| 4'-OMe | 3.58 | 61 |
| 1" | 4.43 | 104 |
| 2"a | 1.99 | 31 |
| 2"b | 1.49 | — |
| 3"a | 1.38 | 19 |
| 3"b | 1.50 | — |
| 4" | 2.25 | 65 |
| 5" | 3.49 | 74 |
| 6" | 1.28 | 18 |
| 4"-NMe$_2$ | 2.26 | 41 |

Chemical shifts referenced to the proton of CHCl$_3$ at 7.26 ppm; 13C data from 2D experiments.

Fractions from the initial fractionation that contained the putative 21-desmethyl-21-sec-butyl spinosyn A were combined, the acetonitrile removed in vacuo, and concentrated using C$_{18}$-BondElute cartridges (200 mg). The sample was applied under gravity, washed with water (10 mL) and eluted with methanol (2×10 mL), then the solvent removed in vacuo.

The putative 21-desmethyl-21-sec-butyl spinosyn A (Compound 11) has the following characteristics.
Molecular Weight: 759
Molecular formula: C$_{43}$H$_{69}$NO$_{10}$
UV (by diode array detection during HPLC analysis): 244 nm
Electrospray MS: m/z for [M+H]+=760.5; forosamine sugar fragment ion at m/z=142.2.

Coexpression of *S. cinnamonensis* Crotonyl-CoA Reductase

In another aspect, the invention provides engineered *S. spinosa* hosts which present an altered substrate supply such that the native polyketide synthase produces novel products. For Example, co-expression of the *S. cinnamonensis* crotonyl-CoA reductase with the spinosyn biosynthetic pathway leads to novel products where the loading module additionally incorporates ethyl malonyl-CoA to yield 21-desethyl-21-n-propyl spinosyns A and D, and the AT of module 8 additionally incorporates ethyl malonyl-CoA to yield 6-ethyl spinosyn A. In addition, both of these AT domains can accept ethyl malonyl-CoA to yield 6-ethyl-21-desethyl-21-n-propyl spinosyn.

The spinosyn loading module comprises a KSqAT0ACP0 which predominantly decarboxylates methyl malonyl-CoA to incorporate propionate. Loading modules containing a KSq are generally more specific than those that lack them. It is therefore interesting and unusual that the spinosyn loading module occasionally accepts malonyl-CoA (naturally producing trace amounts of spinosyn E) and, as disclosed here, unexpectedly accepts ethyl malonyl-CoA when it is present.

For evidence supporting this concept see Example 18 and the discussion immediately preceding Example 22.

Hybrid Spinosyn PKS with Heterologous Extension Modules

In another of its aspects the invention provides hybrid spinosyn PKSs comprising a heterologous extension module or a spinosyn extension module with a heterologous AT domain.

The AT domains select the extender units that are incorporated into the growing polyketide chain. In spinosyn biosynthesis, the extender is predominantly malonyl-CoA. However, the AT in module 3 is essentially specific for methyl malonyl-CoA. It occasionally incorporates malonyl-CoA, leading to the accumulation of spinosyn F as a natural minor component. The AT in module 8 shows a relaxed specificity, incorporating predominantly malonyl-CoA (to give spinosyn A) but also incorporating a significant amount methyl malonyl-CoA (to give about 15% spinosyn D). The amino acid sequence of the module 8 AT is similar to other AT domains in regions that are associated with the selection of methyl malonyl-CoA. We suggest therefore that the incorporation of predominantly malonyl-CoA at this position is a reflection of substrate supply, in combination with an AT domain that has an unusually loose specificity. The AT of the loading module is largely selective for methyl malonyl-CoA, but incorporates malonyl-CoA 5-10% of the time (leading to production of the natural minor component spinosyn E).

Replacement of an existing AT domain with a heterologous AT domain selective for a different malonyl-CoA leads to a PKS that will add, remove or replace a side chain on the spinosyn polyketide. Where the heterologous AT domain can incorporate an extender molecule which is not readily available within the cell, accessory genes are included to provide the co-substrate (Stassi et al. 1998). For Example, there is no obvious gene encoding a crotonyl-CoA reductase in the genome of *S. spinosa* (C. Waldron, unpublished observation) and therefore it is anticipated that the supply of ethyl malonyl-CoA is severely limited in this organism.

A system was constructed to allow AT swaps to be carried out in module 3 of the spinosyn polyketide synthase. The AT of module 3 naturally incorporates methyl malonyl-CoA and introduces the 16-methyl branch in spinosyn. One way to effect an AT swap is by replacement, which will result in a strain with the same transcripts as in the native PKS. An alternative method is via single integration, which places the complete plasmid sequence into the spinosyn PKS genes and requires that a promoter be introduced to drive the genes downstream of the integration site.

The following Examples (Examples 16-19) describe AT domain-swap experiments which involve subcloning fragments using the enzyme MscI. MscI is affected by dcm methylation due to the sequences surrounding the site. Plasmids which are required to be digested with MscI are therefore passaged through *E. coli* ET12567, a dcm$^{-1}$ strain, to generate DNA which is not methylated by dcm.

A. Hybrid Spinosyn PKS Using Module 2AT of the Rapamycin PKS in Plance of Spinosyn Module 3 AT Using the single integration approach, a spinosyn PKS was generated in which the module 3 AT (specific for methyl malonyl-CoA) was replaced by the rapamycin module 2 AT (malonyl-CoA specific). The resulting strain was designated *S. spinosa* 7D23. The PKS genes of 7D23 contain spnA, spnB and a truncated spnC under the native spnA promoter, followed by the plasmid sequence (including the apramycin resistance marker) and the hybrid spnC and spnD and spnE under control of an introduced promoter. In 7D23 the heterologous promoter used was the promoter for resistance to pristinamycin. Alternative promoters could also be used, for example the actI promoter with its cognate activator actII-ORF4.

*S. spinosa* 7D23 produced the four predicted spinosyn analogues, spinosyn F, spinosyn F 17-pseudoaglycone, 16-desmethyl spinosyn D and 16-desmethyl spinosyn D 17-pseudoaglycone. The yields were unexpectedly high, being only 3-fold lower than from a non-engineered strain (see Table 12 within Example 20). The spinosyn F compounds have been identified previously, as minor components in non-engineered strains, but this manipulation of the PKS genes resulted in a dramatic increase in their yield.

The abundance of the pseudoaglycone F may be a reflection of a reduced activity of the forosamine glycosyl transferase for this novel substrate. The final glycosylation occurs at C-17, so the neighboring C-16 methyl group may be important for substrate recognition.

EXAMPLE 16

Figure 7A:
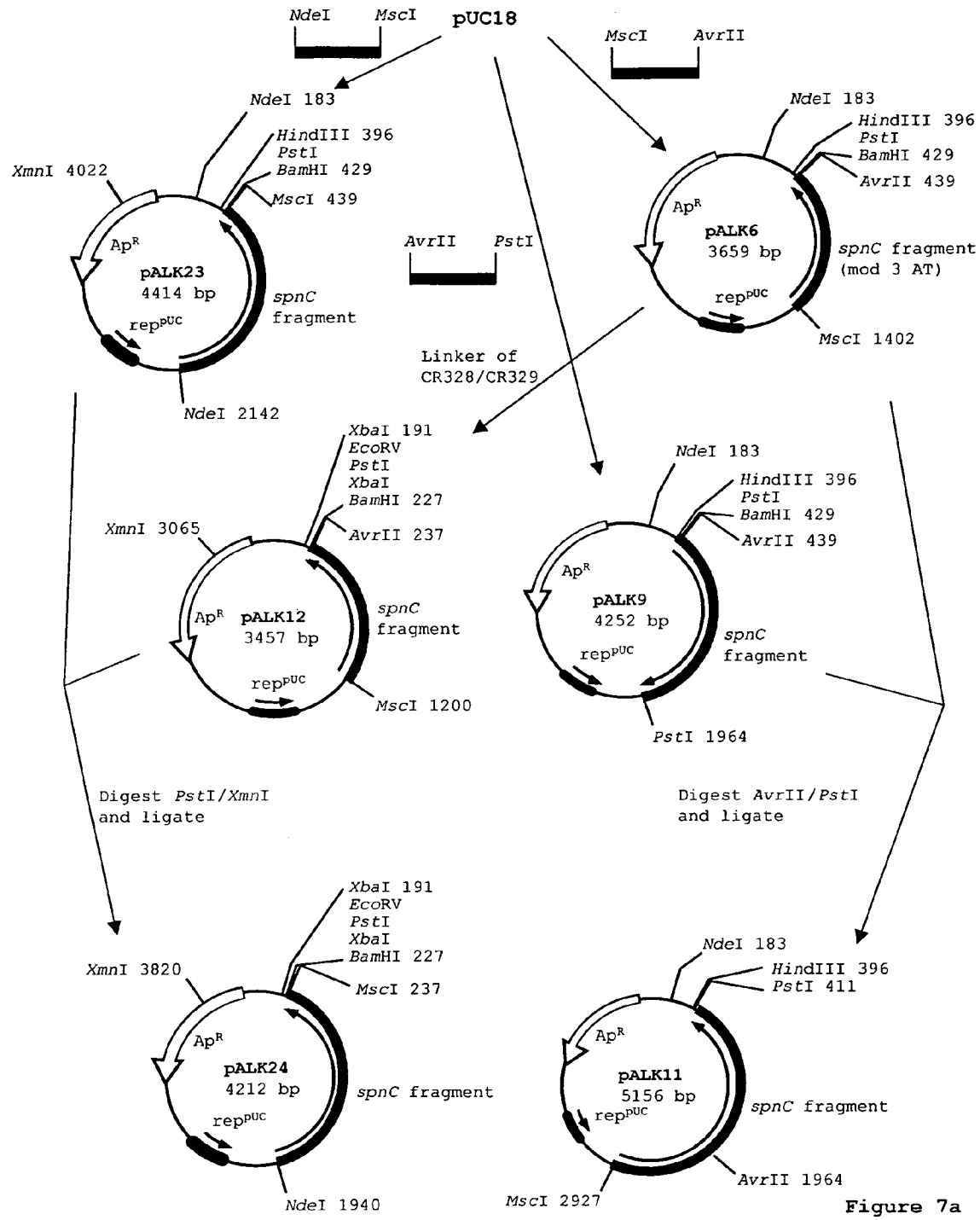
FIGS. 7a and 7b show the construction of pALK26, intermediate plasmid used to generate module 3 AT swap plasmids.
Figure 7B:
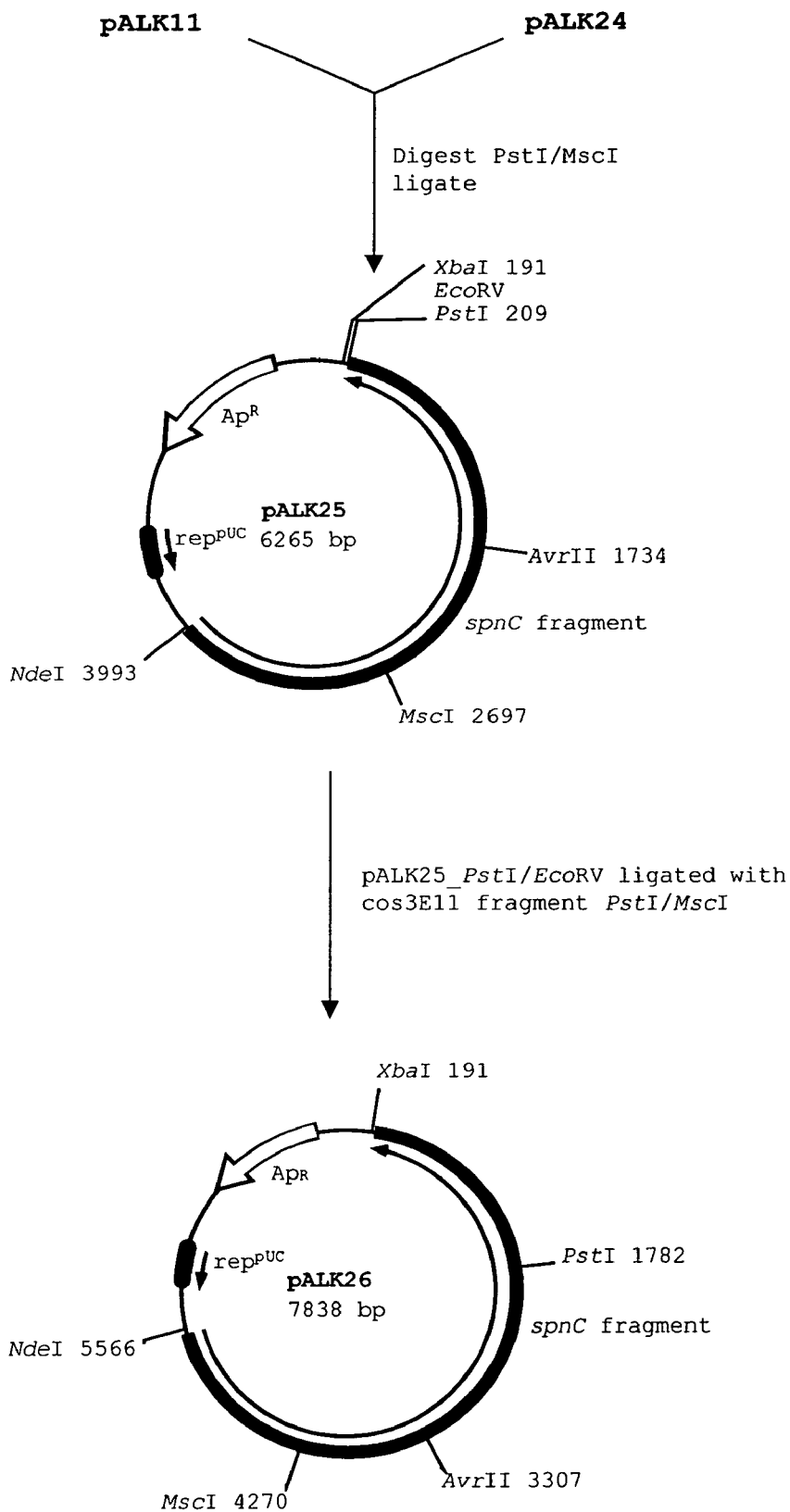
Figure 8:
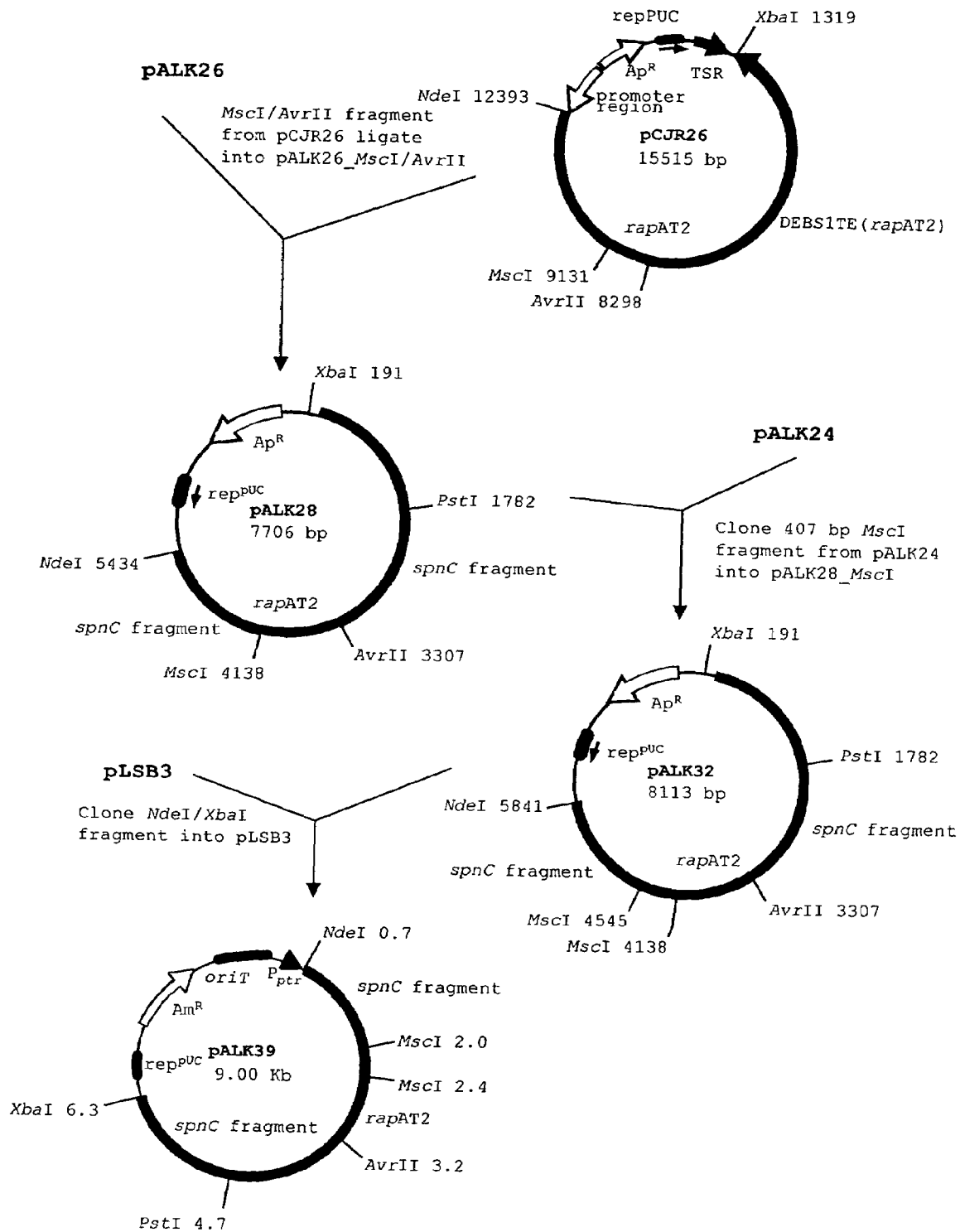
FIG. 8 shows the construction of pALK39, a vector used to introduce the rapAT2 into spinosyn module 3.
Figure 9:
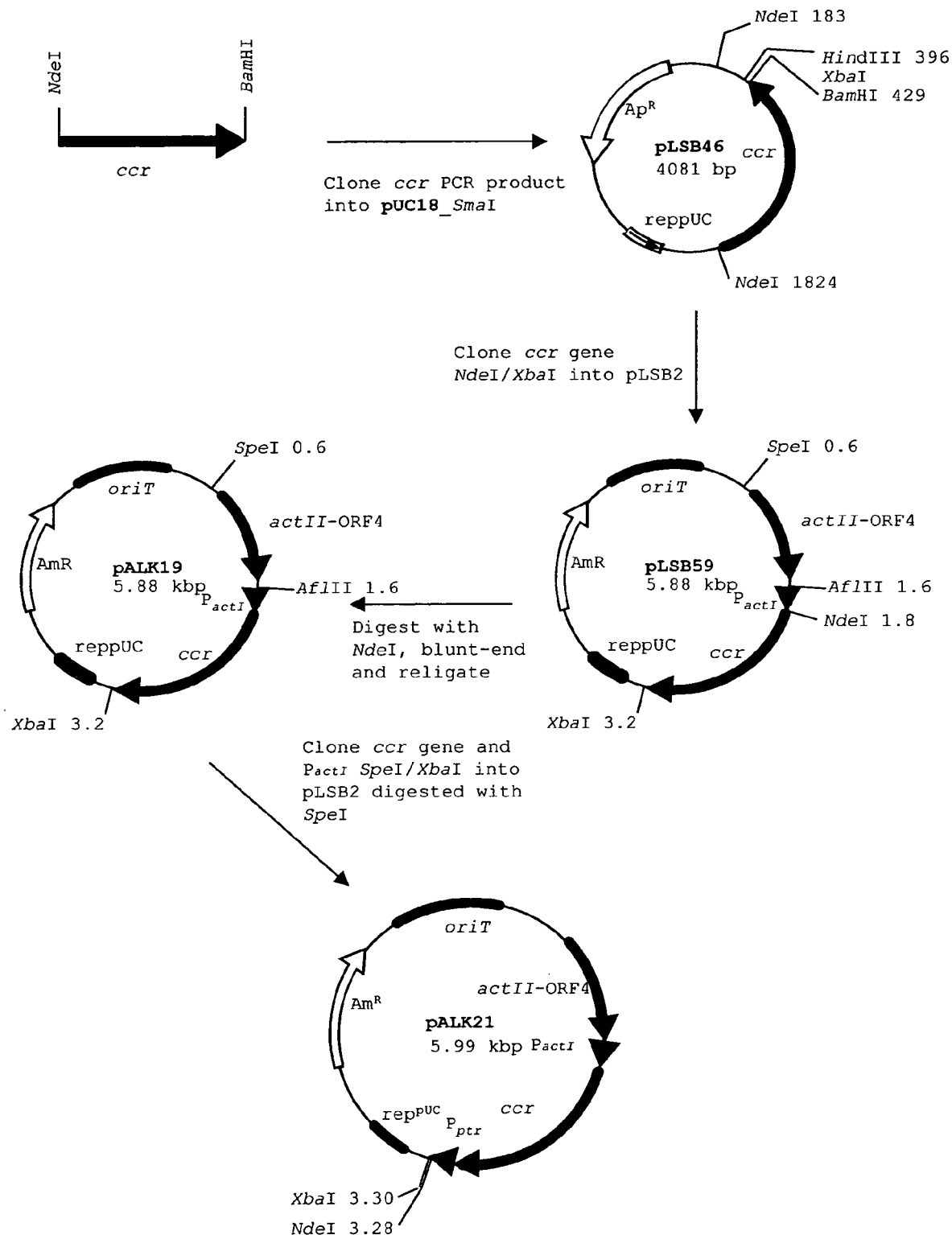
FIG. 9 shows the construction of pALK21, a vector designed to express the *S. cinnamonensis* crotonyl-CoA reductase gene in *S. spinosa*.

Construction of a Vector Containing Spinosyn Module 3 AT with Flanking Restriction Sites See FIGS. 7a and 7b. The spinosyn module 3 AT domain was amplified by PCR using pRHB3E11 as the template and the primers CR322 (SEQ ID NO:12) and CR323(SEQ ID NO:13). These primers introduce MscI and AvrII sites (bp 3-8 of SEQ ID NOS:12 and 13) flanking the AT domain. The 973 bp PCR product was phosphorylated and cloned into commercially-available pUC18 which had previously been digested with SmaI and dephosphorylated. Insert-containing transformants were screened for orientation and sequenced. One transformant, carrying an insert of the correct sequence in the orientation which places the AvrII site next to the HindIII site of the polylinker, was designated pALK6.

The flanking region downstream of the spinosyn module 3 AT was amplified by PCR using pRHB3E11 as the template and the primers CR324 (SEQ ID NO:14) and CR332 (SEQ ID NO:15). Primer CR324 introduces an AvrII site (bp 3-8 of SEQ ID NO:14) at exactly the same position as CR323, and CR332 binds downstream of a PstI site which is naturally occurring in the sequence. The 1557 bp PCR product was phosphorylated and cloned into commercially-available pUC18 which had previously been digested with SmaI and dephosphorylated. Insert-containing transformants were screened for orientation and sequenced. One transformant, carrying an insert of the correct sequence in the orientation which places the AvrII site adjacent to the HindIII site of the polylinker, was designated pALK9. pALK9 was digested with AvrII and PstI. The 1525 bp fragment was gel-purified and cloned into pALK6 digested with AvrII and PstI, to give plasmid pALK11.

pALK12 was constructed to provide a suitable polylinker for this experiment. pALK6 was digested with NdeI and PstI and ligated with an annealed linker of oligos CR328 (SEQ ID NO:16) and CR329 (SEQ ID NO:17). The linker was designed to destroy the NdeI site and leave XbaI, EcoRV and PstI sites. Insert-containing clones were analysed by restriction enzyme digestion and a single clone displaying the correct pattern was designated pALK12.

The flanking region upstream of the spinosyn module 3 AT was amplified by PCR using pRHB3E11 as the template and the primers CR330 (SEQ ID NO:18) and CR321 (SEQ ID NO:19). Primer CR330 introduces an NdeI site (bp 18-23 of SEQ ID NO:18) at the ATG start codon of the spnC gene, and CR321 incorporates an MscI site (bp 3-8 of SEQ ID NO:19) at exactly the same position as CR322. The 1729 bp PCR product was phosphorylated and cloned into commercially-available pUC18 which had previously been digested with SmaI and dephosphorylated. Insert-containing transformants were screened for orientation and sequenced. One transformant, carrying an insert of the correct sequence in the orientation which places the MscI site adjacent to the HindIII site of the polylinker, was designated pALK23. pALK12 was digested with PstI and XmnI and the 601 bp cloned into PstI/XmnI digested pALK23 to give pALK24. pALK11 was digested with PstI and MscI and the 2488 bp fragment was ligated into the 3777 bp backbone produced by digesting pALK24 with PstI and MscI, to give pALK25. To ensure sufficient homology for integration, the fragment of DNA from the PstI site (bp 39607-39612 of SEQ ID NO:1 in U.S. Pat. No. 6,274,350 B1) to the MscI site (bp 41189-41194) was excised from pRHB3E11 and cloned into pALK25 previously digested with PstI and EcoRV to give pALK26.

pALK26 is the intermediate plasmid in the experiments to generate spinosyn PKS genes with AT swaps in module 3. It contained the spinosyn AT3 with flanking restriction sites, the upstream region of spnC to the start codon, and a region downstream for homologous recombination. It was missing a 407 bp MscI-MscI fragment just upstream of the MscI site at the edge of the AT, which has to be inserted after the AT swap has been achieved.

EXAMPLE 17

Construction of a Vector Which Can Be Used to Engineer the Spinosyn Biosynthetic Pathway to Produce C-16 Desmethyl Spinosyns See FIG. 8. Plasmid pALK39 was used to integrate into the chromosome of *S. spinosa* by homologous recombination. It was designed to incorporate the rapamycin AT2 into spinosyn module 3. Such an engineered *S. spinosa* strain produced C-16 desmethyl spinosyns and intermediates in this pathway. Plasmid pALK39 was constructed as described below.

The rapamycin module 2 was excised from pCJR26 as an MscI/AvrII fragment (see SEQ ID NO 20) and ligated into pALK26 which had previously been digested with MscI and AvrI, to give pALK28. The 407 bp MscI fragment missing from this construct was then excised from pALK24 (Example 16) and ligated into dephosphorylated, MscI-digested pALK28. Clones were screened for the orientation of the insert, and a single clone containing the insert in the correct orientation was designated pALK32. pALK32 contains the required fragment to introduce the rap AT2 swap into module 3 of *S. spinosa*, with an NdeI site at the start codon and a downstream XbaI site just outside of the polyketide synthase sequence. This region was excised as an NdeI/XbaI fragment and cloned into pLSB3 to give pALK39. The new module 3 hybrid fragment was thereby placed under Pptr, in a vector which can be transferred into *S. spinosa* by conjugation and selected by apramycin resistance.

EXAMPLE 18

Construction of a Vector Capable of Over-Expressing a Crotonyl-CoA Reductase See FIG. 9. In order to address substrate supply issues, pALK21 was constructed to over-express the crotonyl-CoA reductase (ccr) gene from *Streptomyces cinnamonensis*. pALK21 was constructed as described below.

The *S. cinnamonensis* ccr gene was amplified by PCR from genomic DNA isolated from *S. cinnamonensis* ATCC 15413 using primers CCRMONF (SEQ ID NO:21) and CCRMONR (SEQ ID NO:22). CCRMONF introduces an NdeI site (bp 7-12 of SEQ ID NO:21) which incorporates the ATG of the start codon of the gene, and CCRMONR introduces a BamHI site (bp 6-11 of SEQ ID NO:22) downstream of the stop codon. Amplification to obtain the ccr gene was carried out under standard conditions using Pwo thermostable DNA polymerase. The fragment was phosphorylated with T4 polynucleotide kinase then cloned into commercially-available pUC18 digested with SmaI and dephosphorylated. Insert-containing plasmids were sequenced, and one plasmid containing the correct sequence was designated pLSB46. Plasmid pLSB46 contains the *S. cinnamonensis* ccr gene in the orientation which places the introduced BamHI site adjacent to the XbaI site of the polylinker. SEQ ID NO 23 shows the ccr gene from the NdeI site at the start codon to the BamHI site after the stop codon.

The ccr gene was excised as an NdeI/XbaI fragment and cloned into the expression vector pLSB2 (Example 2) digested with NdeI and XbaI, to give pLSB59. Plasmid pLSB59 contains the ccr gene under control of the actI promoter, and the activator actII-ORF4. In order to co-express the ccr gene with an engineered hybrid PKS, the ccr-containing fragment, along with the actII-ORF4 activator and actI promoter, was transferred into a vector containing a second promoter (Pptr) which has restriction sites available for a hybrid PKS gene. This was achieved as described below.

Plasmid pLSB59 was digested with NdeI, and the ends were filled-in using the Klenow fragment of DNA polymerase I. This blunt-end fragment was re-circularized to give pALK19. The gene and promoter were excised from pALK19 as a SpeI/XbaI fragment and cloned into pLSB3 (Example 2) digested with SpeI. This step destroys the XbaI site at the end of the ccr gene. The resulting plasmid is designated pALK21. Plasmid pALK21 therefore contains the ccr gene under $P_{actI}$ with unique NdeI and XbaI sites situated for the introduction of hybrid PKS genes downstream of the ptr promoter. pALK21 is apramycin resistant and contains an oriT for conjugal transfer of DNA.

EXAMPLE 19

Generation of a *S. spinosa* Strain Harbouring a Hybrid Polyketide Synthase Comprising the Rapamycin Module 2 AT in Place of the Spinosyn Module 3 AT See FIG. 11. *Saccharopolyspora spinosa* NRRL 18538 was transformed by conjugation (Matsushima et al. 1994) from *E. coli* S17-1 (Simon et al., 1983) with pALK39. Transformants were selected for resistance to apramycin. A number of transformants were screened by Southern blot analysis. A single transformant, displaying the correct hybridization pattern to show that the plasmid had integrated into the chromosome by homologous recombination, was designated strain S. spinosa 7D23.

Examples 20-21 hereinafter illustrate the use of S. spinosa 7D23 to produce novel spinosyns.

EXAMPLE 20

Production and Isolation of 16-Desmethyl Spinosyns (Production of Spinosyn F, Spinosyn F Pseudoaglycone, and Compounds 21 and 22)

16-Desmethyl spinosyn A has previously been identified as one of the family of spinosyns produced by a number of *S. spinosa* strains, and designated spinosyn F (U.S. Pat. No. 6,274,350 B1). Here we demonstrated production of spinosyn F and 16-desmethyl spinosyn D (Compound 21) from the engineered hybrid pathway of *S. spinosa* 7D23.

*S. spinosa* 7D23 was used to inoculate CSM medium (Hosted and Baltz 1996; U.S. Pat. No. 5,362,634). This preculture was grown in a 250 mL flask with a 30 cm spring to aid aeration, shaken at 250 rpm with a two-inch throw, at 30° C. with 75% relative humidity for 3 days. It was then used to inoculate vegetative medium, 3×30 mL cultures in 250 mL flasks (Strobel and Nakatsukasa 1993; U.S. Pat. No. 5,362,634) at 5% v/v, which was cultured under the same conditions for a further 2 days. The vegetative culture was used to inoculate production medium (Strobel and Nakatsukasa 1993) at 5% v/v, 30×30 mL cultures in 250 mL flasks grown under the conditions described above. The production culture of *S. spinosa* 7D23 was grown for 10 days.

For the identification of metabolites, a 1 mL aliquot of fermentation broth was analyzed by LC-MS as described in Example 5. By comparison to authentic standards, it was clear that spinosyn F, 16-desmethyl spinosyn D, and their corresponding pseudoaglycones were present (Table 12).

TABLE 12

| Compound | Retention time (min) | Key mass spectral data (m/z) | Yield (mg/l) |
|---|---|---|---|
| spinosyn F | 21.1 | 718.5 $[M + H]^+$; 142.4 | 102 |
| 16-desmethyl spinosyn D (Compound 21) | 23.4 | 732.5 $[M + H]^+$; 142.3 | 38 |
| spinosyn F 17-pseudoaglycone | 23.1 | 599.3 $[M + Na]^+$ | 125 |
| 16-desmethyl spinosyn D 17-pseudoaglycone (Compound 22) | 24.6 | 613.3 $[M + Na]^+$ | 42 |

The remaining fermentation broth was clarified by centrifugation. The cells were extracted twice with an equal volume of methanol. The supernatant (780 mL) was adjusted to pH~10 with 5 N NaOH and twice extracted with ethyl acetate (3×500 mL). The methanol and ethyl acetate extracts were combined and the solvents removed in vacuo to give an oily residue. The residue was dissolved into ethyl acetate (250 mL) and extracted with 50 mM tartaric acid (3×200 mL). The combined tartaric acid extracts were adjusted to pH~10 with 5 N NaOH and extracted with ethyl acetate (3×300 mL). The extracts were combined and the solvent removed in vacuo to yield a brown oil (200 mg). The oil was dissolved into methanol (1 mL) and half of this was initially chromatographed as described in Example 8.

The major fractions from the initial separation that contained 16-desmethyl spinosyn D and spinosyn F were combined and the solvent removed in vacuo. The residues were chromatographed over the same column, eluting with a gradient as described below at a flow rate of 21 mL/min.

T=0 min, 35% B; T=35, 55% B; T=45, 55% B.

Fractions were collected every 30 seconds. Fractions containing either 16-desmethyl spinosyn D or spinosyn F were combined separately. Each of the combined set of fractions was then worked up as follows: the acetonitrile removed in vacuo, and the sample concentrated using a $C_{18}$-BondElute cartridge (200 mg). The sample was applied under gravity, washed with water (10 mL) eluted with methanol (2×10 mL), and the solvent was removed in vacuo.

16-Desmethyl spinosyn D (Compound 21) has the following characteristics.

Isolated yield: 4.8 mg

Molecular weight: 731

Molecular formula: $C_{41}H_{65}NO_{10}$

UV (by diode array detection during HPLC analysis): 244 nm

Electrospray MS: m/z for $MH^+$=732.5; forosamine sugar fragment ion at m/z=142.4.

Accurate FT-ICR-MS: m/z for $[MH]^+$=732.4689 (requires 732.4681).

Table 13 summarizes the $^1H$ and $^{13}C$ NMR chemical shift data for 16-desmethyl spinosyn D in $CDCl_3$.

TABLE 13

| Position | $^1H$ | $^{13}C$ |
|---|---|---|
| 1 | — | 172.3 |
| 2a | 2.39 | 33.9 |
| 2b | 3.09 | — |
| 3 | 2.97 | 47.7 |
| 4 | 3.37 | 42.1 |
| 5 | 5.49 | 122.0 |
| 6 | — | 136.3 |
| 6-Me | 1.73 | 20.7 |
| 7 | 2.19 | 44.5 |
| 8a | 1.41 | 34.8 |
| 8b | 1.93 | — |
| 9 | 4.29 | 75.7 |
| 10a | 1.35 | 37.7 |
| 10b | 2.26 | — |
| 11 | 1.01 | 45.6 |
| 12 | 2.76 | 49.0 |
| 13 | 6.75 | 148.7 |
| 14 | — | 145.1 |
| 15 | — | 198.0 |
| 16a | 2.47 | 45.1 |
| 16b | 3.17 | — |
| 17 | 4.05 | 74.4 |
| 18a | 1.56 | 33.7 |
| 18b | 1.56 | — |
| 19a | 1.17 | 21.5 |
| 19b | 1.67 | 21.5 |
| 20a | 1.51 | 29.7 |
| 20b | 1.51 | — |
| 21 | 4.65 | 76.9 |
| 22a | 1.49 | 28.2 |
| 22b | 1.49 | — |
| 23 | 0.82 | 9.3 |
| 1' | 4.85 | 95.5 |
| 2' | 3.52 | 77.6 |
| 3' | 3.46 | 81.1 |
| 4' | 3.12 | 82.3 |
| 5' | 3.54 | 67.9 |
| 6' | 1.28 | 17.8 |
| 2'-OMe | 3.51 | 59.1 |
| 3'-OMe | 3.50 | 57.7 |
| 4'-OMe | 3.56 | 61.0 |
| 1" | 4.60 | 98.9 |
| 2"a | 1.67 | 30.0 |
| 2"b | 1.99 | — |
| 3"a | 1.70 | 20.5 |
| 3"b | 2.16 | — |
| 4" | 3.10 | 64.6 |

TABLE 13-continued

| Position | $^1$H | $^{13}$C |
|---|---|---|
| 5" | 3.73 | 70.7 |
| 6" | 1.47 | 18.6 |
| 4"-NMe$_2$ | Not seen* | Not seen* |

Chemical shifts referenced to the proton of 7.26 ppm.
*Not seen due to trace acid causing protonation of amine group.

Spinosyn F has the following characteristics.
Isolated yield: 5.5 mg
Molecular weight: 717
Molecular formula: $C_{40}H_{63}NO_{10}$
UV (by diode array detection during HPLC analysis): 244 nm
Electrospray MS: m/z for MH$^+$=718.5; forosamine sugar fragment ion at m/z=142.4.
Accurate FT-ICR-MS: m/z for [MH]$^+$=718.4534 (requires 718.4525).
The NMR data accumulated for this compound were in agreement with its proposed identity and with published data (U.S. Pat. No. 5,362,634).

EXAMPLE 21

Production and Isolation of 16-Desmethyl Spinosyn D 17-Pseudoaglycone (Compound 22)

16-Desmethyl spinosyn A 17-pseudoaglycone was previously identified and is known as spinosyn F 17-pseudoaglycone. It is found as one of the minor members of the family of spinosyns produced by *S. spinosa* strains (U.S. Pat. No. 6,274,350 B1). Described below is the process for the production of spinosyn F 17-pseudoaglycone and 16-desmethyl spinosyn D 17-pseudoaglycone from the engineered hybrid pathway of *S. spinosa* 7D23.

Frozen vegetative stocks of *S. spinosa* 7D23 were used to inoculate primary vegetative pre-cultures of *S. spinosa* 7D23 in CSM (50 mL incubated in a 250 mL Erlenmeyer flask with spring). Secondary pre-cultures in vegetative medium (250 mL incubated in a 2 L Erlenmeyer flask with spring) were prepared and incubated as described in Example 8.

Four liters of production medium were prepared, as in Example 6, with the addition of 0.01% v/v Pluronic L-0101 (BASF) antifoam. Production medium was inoculated with the secondary pre-culture at 5% v/v and was allowed to ferment in a 7 L stirred bioreactor for 7-10 days at a temperature of 30° C. Airflow was set at 0.75 vvm, and impeller tip speed was controlled between 0.68 and 1.1 ms$^{-1}$ in order to maintain dissolved oxygen tension at or above 30% of air saturation.

For the identification of metabolites, a 1 mL aliquot of fermentation broth was analyzed by LC-MS as described in Example 5. By comparison to authentic standards, it was clear that spinosyn F, 16-desmethyl spinosyn D and their corresponding pseudoaglycones were present (Table 14).

TABLE 14

| Compound | Retention time (min) | Key mass spectral data (m/z) |
|---|---|---|
| Spinosyn F | 21.4 | 718.4 [M + H]$^+$; 142.4 |
| 16-desmethyl spinosyn D (Compound 21) | 23.6 | 732.5 [M + H]$^+$; 142.3 |
| Spinosyn F 17-pseudoaglycone | 23.2 | 599.3 [M + Na]$^+$ |
| 16-desmethyl spinosyn D 17-pseudoaglycone (Compound 22) | 24.3 | 613.3 [M + Na]$^+$ |

The remaining fermentation broth was clarified by centrifugation. The cells were twice extracted with an equal volume of methanol. The supernatant (3.2 L) was extracted with ethyl acetate (2×1.5 L). The methanol and ethyl acetate extracts were combined and the solvent removed in vacuo. The residual oil was dissolved into ethyl acetate (1 L) and washed with 50 mM tartaric acid (3×500 mL). The remaining ethyl acetate solution was evaporated in vacuo. The resulting oil was chromatographed over flash silica gel (6×13 cm) eluting with 5% methanol in chloroform. Fractions of 10 mL volume were collected. The fractions containing pseudoaglycones were combined and the solvent removed in vacuo to yield a brown oil. The brown oil was dissolved into methanol (1.5 mL) and chromatographed over base-deactivated reversed-phase silica gel as described in Example 8. Fractions were collected every 30 seconds and those containing the relevant products were combined, the acetonitrile was removed in vacuo and the sample concentrated using $C_{18}$-BondElute cartridges (200 mg). The sample was applied under gravity, washed with water (10 mL), eluted with methanol (2×10 mL), and the solvent removed in vacuo.

16-desmethyl spinosyn D 17-pseudoagylcone (Compound 22) had the following characteristics:
Isolated yield: 3.3 mg
Molecular weight: 590
Molecular formula: $C_{33}H_{50}O_9$
UV (by diode array detection during HPLC-MS analysis): 240 nm
Electrospray MS: m/z for [M+Na]$^+$=613.3
Accurate FT-ICR-MS: m/z for [M+H]$^+$=591.3517 (requires: 591.3528).
Table 15 summarizes the $^1$H and $^{13}$C NMR spectral data for 16-desmethyl spinosyn D 17-pseudoagylcone in CDCl$_3$.

TABLE 15

| Position | $^1$H | $^{13}$C |
|---|---|---|
| 1 | — | 172.5 |
| 2a | 2.40 | 34.0 |
| 2b | 3.13 | — |
| 3 | 2.97 | 47.7 |
| 4 | 3.37 | 42.4 |
| 5 | 5.49 | 122.1 |
| 6 | — | 136.3 |
| 6-Me | 1.73 | 20.7 |
| 7 | 2.19 | 44.5 |
| 8a | 1.42 | 34.5 |
| 8b | 1.93 | — |
| 9 | 4.30 | 75.6 |
| 10a | 1.36 | 37.7 |
| 10b | 2.28 | — |
| 11 | 1.03 | 45.6 |
| 12 | 2.76 | 48.9 |
| 13 | 6.77 | 148.0 |
| 14 | — | 145.1 |
| 15 | — | 197.8 |
| 16a | 2.56 | 47.5 |
| 16b | 3.21 | — |
| 17 | 4.18 | 68.2 |
| 18a | 1.58 | 35.7 |
| 18b | 1.58 | — |
| 19a | 1.20 | 21.1 |
| 19b | 1.60 | — |
| 20a | 1.45 | 30.5 |
| 20b | 1.56 | — |
| 21 | 4.68 | 76.3 |
| 22a | 1.50 | 28.0 |
| 22b | 1.50 | — |
| 23 | 0.83 | 9.4 |
| 1' | 4.86 | 95.5 |
| 2' | 3.51 | 77.7 |
| 3' | 3.46 | 81.1 |

TABLE 15-continued

| Position | $^1$H | $^{13}$C |
|---|---|---|
| 4' | 3.12 | 82.3 |
| 5' | 3.54 | 67.9 |
| 6' | 1.28 | 17.8 |
| 2'-OMe | 3.51 | 59.0 |
| 3'-OMe | 3.51 | 57.7 |
| 4'-OMe | 3.56 | 60.9 | b. Hybrid Spinosyn PKS Using 5 AT Module of the Tylosin PKS in Place of Spinosyn Module 3 AT In an analogous way, a hybrid spinosyn PKS was generated in which the methyl malonyl-CoA specific AT domain of module 3 was replaced by the ethyl malonyl-CoA specific AT domain of tylosin module 5 (SEQ ID NO:26). The producing strain was designated S. spinosa 36P4. Ethyl malonyl-CoA was not expected to be abundant in S. spinosa, so the S. cinnamonensis gene encoding crotonyl-CoA reductase was expressed in the same cell, under control of the acti promoter. This should significantly increase the intracellular pool of butyryl-CoA, which is a substrate for short chain fatty acid carboxylases that can provide ethyl malonyl-CoA. The PKS of S. spinosa 36P4 contained spnA, spnB and a truncated spnC under the native spnA promoter, followed by the plasmid DNA including the apramycin resistance marker. The S. cinnamonensis crotonyl-CoA reductase under the actI promoter, and the actII-ORF4 activator, were also within the plasmid sequence. This was followed by the hybrid spnC (spnC*) gene under control of the promoter for resistance to pristinamycin. One skilled in the art will appreciate that the heterologous promoters could be swapped around, or indeed that a number of other promoters could be chosen.

Strain S. spinosa 36P4 produced minor components which had the UV absorbance, chromatographic properties, masses and fragmentation patterns consistent with the expected 16-desmethyl-16-ethyl spinosyns A and D. The major products from S. spinosa 36P4 were spinosyns A and D. Surprisingly, the predominant novel fermentation products of strain 36P4 were 21-desethyl-21-n-propyl spinosyn A and 6-ethyl spinosyn A. 21-desethyl-21-n-propyl spinosyn A was produced at levels within 10% of that of spinosyn D. These compounds were isolated and fully characterized by MS and NMR. We suggest that they were made due to an increase in the intracellular concentration of ethyl malonyl-CoA, which resulted from the introduction of the crotonyl-CoA reductase gene. The low specificity of both the loading AT and the module 8 AT allowed this novel substrate to be incorporated. 6-Ethyl-21-desethyl-21-n-propyl spinosyn A was also made by S. spinosa 36P4, as a minor factor. These three products each have a methyl group at C16, which implies that the tylosin module 5 AT, in this system, predominantly incorporated methylmalonyl-CoA. It is therefore expected that a non-engineered spinosyn PKS (with the native AT3) would produce the 21-n-propyl and 6-ethyl spinosyn comounds in the presence of the ccr gene.

EXAMPLE 22

Figure 10:
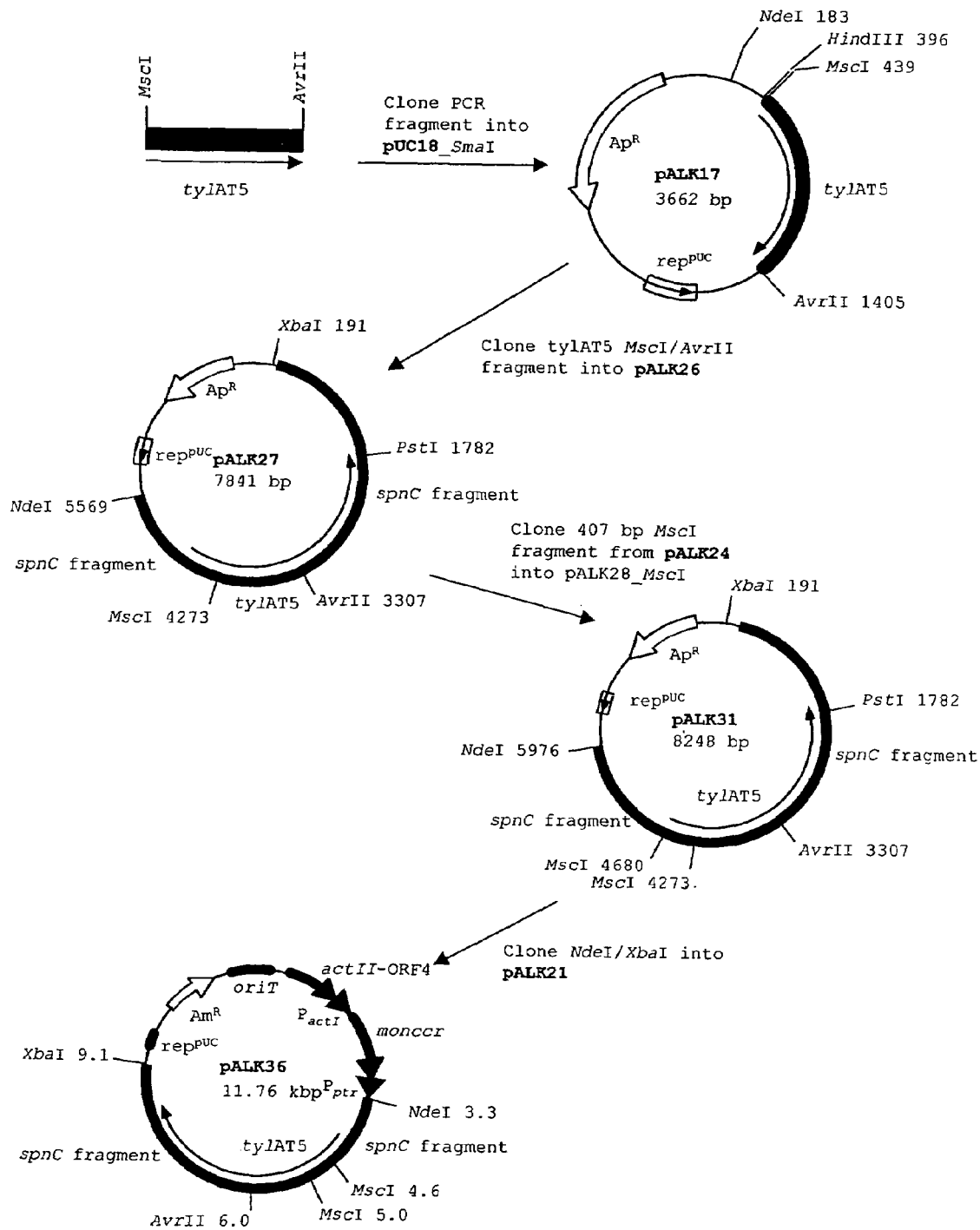
FIG. 10 shows the construction of pALK36, a vector used to introduce the tylAT5 into spinosyn module 3.
Figure 11:
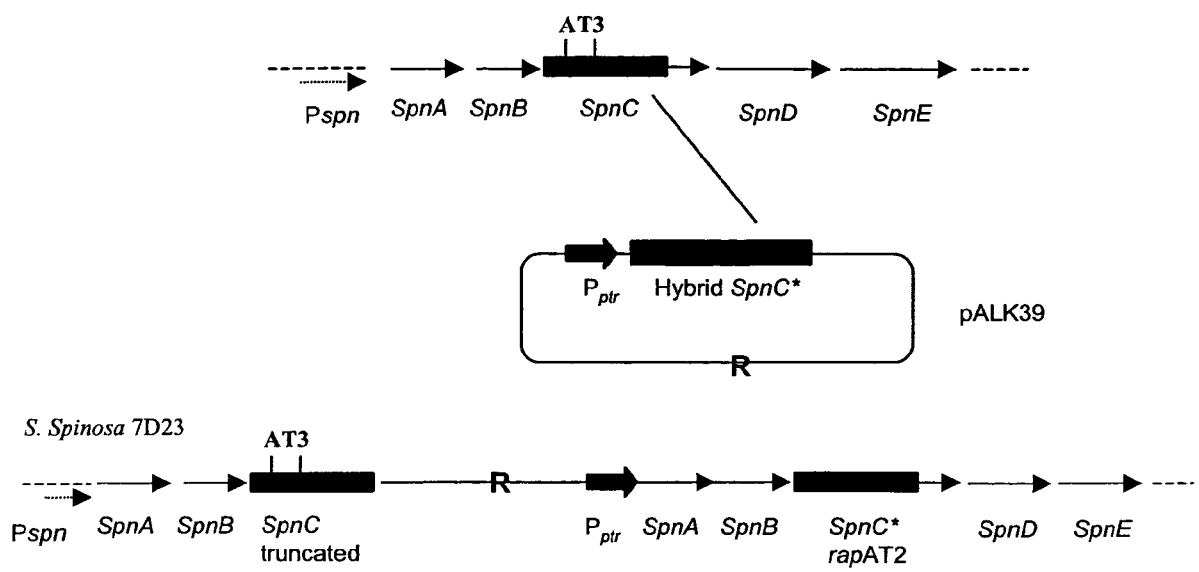
FIG. 11 shows the hybrid PKS pathway of strain *S. spinosa* 7D23.

Construction of a Vector Which Can Be Used to Engineer the Spinosyn Biosynthetic Pathway to Produce 16-desmethyl-16-ethyl Spinosyns See FIG. 10. Plasmid pTB4 is a pUC 18-based plasmid containing a BamHI fragment of the tylosin PKS that includes most of the tylosin module 4. The insert is from the BamHI site between bp 24125 and 24130 of the deposited sequence tylG.embo, accession number U78289 (at the beginning of KS4) and the BamHI site between bp 31597 and 31612 (at the beginning of KS5).

The tylosin module 5 AT was amplified by PCR using the template pTB4 and the primers AK1 (SEQ ID NO:24) and AK2 (SEQ ID NO:25). The primer AK1 introduces an MscI site (bp 3-8 of SEQ ID NO:24) at the beginning of the AT domain and primer AK2 introduces an AvrII site (bp 3-8 of SEQ ID NO:25) at the end of the AT domain. The PCR reaction was carried out under standard conditions using Pwo thermostable DNA polymerase. The fragment was phosphorylated with T4 polynucleotide kinase and cloned into commercially-available pUC18 digested with SmaI and dephosphorylated. Insert-containing plasmids were analysed for the orientation of the insert and sequenced. One plasmid containing the correct sequence was identified and designated pALK17. It contains the PCR fragment in the orientation which places the MscI site adjacent to the HindIII site of the polylinker. The tyl AT5 was excised from pALK17 as an MscI/AvrII fragment and cloned into pALK26 digested with MscI and AvrII to give pALK27. The 407 bp MscI fragment which is missing from this construct was excised from pALK24 (Example 16) and ligated into dephosphorylated, MscI-digested pALK27. A single clone containing the insert in the correct orientation was designated pALK31. pALK31 contains the required fragment to introduce the tyl AT5 swap into module 3 of S. spinosa, with an NdeI site at the start codon and a XbaI site just downstream of the polyketide synthase sequence. This fragment was excised as an NdeI/XbaI fragment and cloned into pALK21 to give pALK36. This places the new module 3 hybrid fragment under $P_{ptr}$, in a vector which co-expresses the ccr from the actI promoter, and can be transferred into S. spinosa by conjugation and selected for apramycin resistance.

EXAMPLE 23

Figure 12:
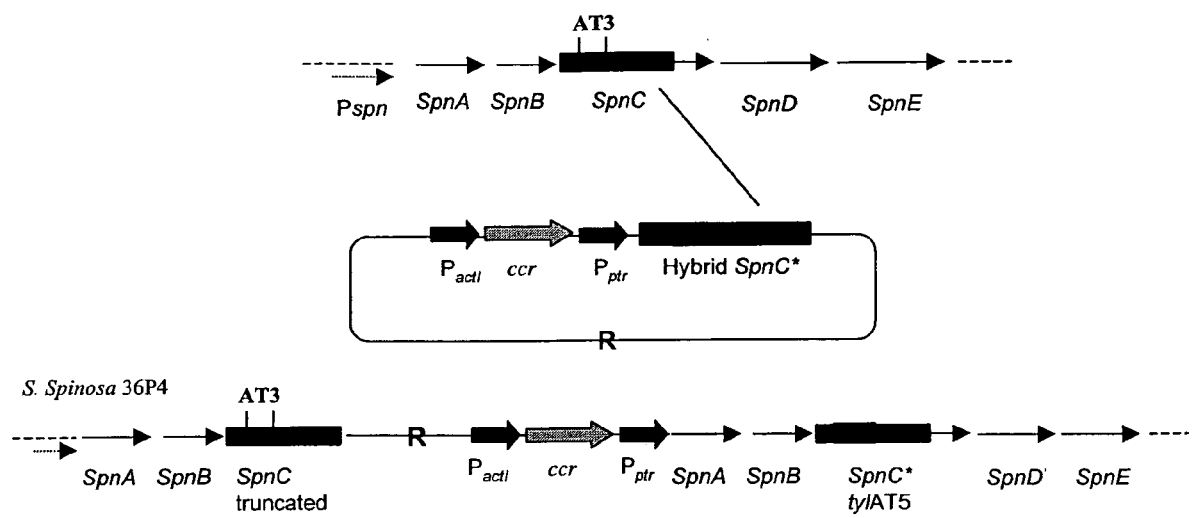
FIG. 12 shows the hybrid PKS pathway of strain *S. spinosa* 36P4.

Generation of a S. spinosa Strain Harbouring a Hybrid Polyketide Synthase Comprising the Tylosin Module 5 AT in Place of the Spinosyn Module 3 AT, and Providing the Appropriate Ethyl Malonyl-CoA Co-Substrate See FIG. 12. Saccharopolyspora spinosa NRRL 18538 was transformed with pALK36. Transformants were selected for resistance to apramycin and screened by Southern blot analysis. A single transformant was designated strain S. spinosa 36P4.

EXAMPLE 24

Production and Isolation of Compounds from S. spinosa 36P4

Frozen vegetative stocks of S. spinosa 36P4 were inoculated into primary vegetative pre-cultures of S. spinosa 36P4 in CSM (50 mL incubated in a 250 mL Erlenmeyer flask with spring). Secondary pre-cultures in vegetative medium (250 mL incubated in a 2 L Erlenmeyer flask with spring) were prepared and incubated as described in Example 8.

Fourteen liters of production medium were prepared, as in Example 6, with the addition of 0.01% v/v Pluronic L-0101 (BASF) antifoam. Production medium was inoculated with the secondary pre-culture at 5% v/v and was allowed to ferment in a 20 L stirred bioreactor for 7-10 days under conditions described in Example 8.

For the identification of metabolites, a 1 mL aliquot of fermentation broth was analyzed by LC-MS as described in Example 5: By comparison to authentic standards, and to a fermentation extract from strain *S. spinosa* NRRL 18538, the presence of new spinosyn metabolites was verified (Table 16). The major new component eluted with a similar—but different—retention time to spinosyn D and had an identical mass; this compound is identified below as 21-desethyl-21-n-propyl spinosyn A. The second significant new component eluted later and had a mass 14 units higher than spinosyn D; this compound is identified below as 6-ethyl spinosyn A. The third significant peak eluted later still and had a mass 28 units higher than spinosyn D; this compound is believed to be 6-ethyl-21-desethyl-21-n-propyl spinosyn A. The mass spectra of all of these compounds displayed a [M+H]$^+$ ion plus the forosamine fragment. In addition, several other new components were clearly present but were present in minor quantities. One of these new components eluted after the first major new component and had an identical mass to spinosyn D; this compound was probably 16-desmethyl-16-ethyl spinosyn A. Other minor new components displayed a [M+H]$^+$ ion 14 mass units higher than spinosyn D and a mass consistent with the forosamine fragment. One of these new minor components may be 16-desmethyl-16-ethyl spinosyn D.

acetonitrile removed in vacuo, and the sample concentrated using a $C_{18}$-BondElute cartridge (200 mg), washed with water (10 mL) and eluted with methanol (2×10 mL), and the solvent removed in vacuo. Fractions from the initial pair of separations that contained mainly 21-desethyl-21-n-propyl spinosyn A (m/z=746) were combined and the solvent removed in vacuo. The residues were dissolved in methanol: water (7:3, 1 mL) and chromatographed over the same column eluting with the following gradient at 21 mL/min.

T=0 min, 40% B; T=45, 80% B.

Fractions were collected ever 30 seconds. Fractions containing only 21-desethyl-21-n-propyl spinosyn A were combined. Samples containing a mixture of this compound with spinosyn D were combined separately, the solvent removed in vacuo, and the residue chromatographed once again as described above. The fractions containing only 21-desethyl-21-n-propyl spinosyn A were then combined with those from the first run. The fractions containing a mixture of the two compounds were combined and another round of chromatography performed.

The fractions from the three runs that contained only 21-desethyl-21-n-propyl spinosyn A were combined, the acetonitrile removed in vacuo and the sample concentrated

TABLE 16

| Compound | Compound No. (See Table 3) | Retention time (min) | Key mass spectral data (m/z) |
|---|---|---|---|
| 21-desethyl-21-n-propyl spinosyn A | 23 | 25.4 | 746.5 [M + H]$^+$; 142.3 |
| 6-ethyl spinosyn A | 24 | 27.1 | 760.5 [M + H]$^+$; 142.4 |
| 6-ethyl-21-desethyl-21-n-propyl spinosyn A | 25 | 29.1 | 774.5 [M + H]$^+$; 142.3 |
| 16-desmethyl-16-ethyl spinosyn A | 26 | 26.4 | 746.5 [M + H]$^+$; 142.3 |
| putative 16-desmethyl-16-ethyl spinosyn D | 27 | 26.7 | 760.4 [M + H]$^+$; 142.4 |
| putative 16-desmethyl-16-ethyl spinosyn D | 27 | 27.3 | 760.4 [M + H]$^+$; 142.4 |
| putative 16-desmethyl-16-ethyl spinosyn D | 27 | 27.5 | 760.5 [M + H]$^+$; 142.3 |

The remaining fermentation broth (12 L) was clarified by centrifugation and extracted as described in Example 8. The residue was dissolved into methanol (10 mL), water (2 mL) and formic acid (100 μl). The whole sample was filtered and applied under gravity to a $C_{18}$-BondElute SPE cartridge (70 g, 150 mL). The cartridge was then developed with an increasing 10%-stepwise gradient of acetonitrile in water (100 mL each step) containing formic acid at 0.1% using a FlashMaster Personal system (Jones Chromatography, Wales UK). The column was finally washed with methanol (2×100 mL). Fractions containing spinosyn-like molecules with a mass of 746 amu or greater were combined and the solvents removed in vacuo. The residual oil (3 mL) was dissolved in methanol (1.5 mL). This sample was initially chromatographed in two equal portions as described in Example 8.

The fractions from the initial pair of separations that contained 6-ethyl spinosyn A and 21-desethyl-21-n-propyl spinosyn D (m/z=760) were combined and the solvent removed in vacuo. The residue was dissolved in methanol (1 mL) and chromatographed over reversed-phase silica gel (Hypersil $C_{18}$-BDS, 5 μm; 21×250 mm) eluting with a gradient as described below, at a flow rate of 21 mL/min.

T=0 min, 40% B; T=80, 50% B.

Fractions were collected every 30 seconds. Fractions containing predominantly 6-ethyl spinosyn A were combined, the using a $C_{18}$-BondElute cartridge (200 mg). The sample was applied under gravity, washed with water (10 mL), eluted with methanol (2×10 mL), and the solvent removed in vacuo.

6-Ethyl spinosyn A (Compound 24) has the following characteristics.

Isolated yield: 4.8 mg
Molecular weight: 759
Molecular formula: $C_{43}H_{69}NO_{10}$
UV (by diode array detection during HPLC analysis): 244 nm
Electrospray MS: m/z for MH$^+$=760.5; forosamine sugar fragment ion at m/z=142.4.
Accurate FT-ICR-MS: m/z for [MNa]$^+$=782.4818 (requires 782.4814).
Table 17 summarizes the $^1$H and $^{13}$C NMR chemical shift data for 6-ethyl spinosyn A in CDCl$_3$.

TABLE 17

| Position | $^1$H | $^{13}$C |
|---|---|---|
| 1 | — | 172.6 |
| 2a | 2.42 | 34.0 |
| 2b | 3.13 | — |
| 3 | 2.97 | 47.9 |
| 4 | 3.44 | 41.9 |
| 5 | 5.46 | 120.3 |

TABLE 17-continued

| Position | $^1$H | $^{13}$C |
|---|---|---|
| 6 | — | 141.8 |
| 7 | 2.23 | 44.4 |
| 8a | 1.42 | 34.5 |
| 8b | 1.95 | — |
| 9 | 4.30 | 75.8 |
| 10a | 1.35 | 37.7 |
| 10b | 2.26 | — |
| 11 | 1.00 | 45.9 |
| 12 | 2.77 | 49.1 |
| 13 | 6.76 | 147.7 |
| 14 | — | 144.4 |
| 15 | — | 202.9 |
| 16 | 3.28 | 47.7 |
| 17 | 3.63 | 80.6 |
| 18a | 1.52 | 34.3 |
| 18b | 1.52 | — |
| 19a | 1.20 | 21.7 |
| 19b | 1.77 | — |
| 20a | 1.52 | 30.0 |
| 20b | 1.52 | — |
| 21 | 4.67 | 76.6 |
| 22a | 1.49 | 28.4 |
| 22b | 1.49 | — |
| 23 | 0.82 | 9.3 |
| 24a | 2.05 | 27.4 |
| 24b | 2.05 | — |
| 25 | 1.03 | 12.6 |
| 26 | 1.17 | 16.1 |
| 1' | 4.85 | 95.5 |
| 2' | 3.50 | 77.7 |
| 3' | 3.47 | 81.0 |
| 4' | 3.12 | 82.3 |
| 5' | 3.55 | 67.9 |
| 6' | 1.28 | 17.8 |
| 2'-OMe | 3.50 | 59.0 |
| 3'-OMe | 3.50 | 57.7 |
| 4'-OMe | 3.56 | 60.9 |
| 1" | 4.43 | 103.4 |
| 2"a | 1.50 | 30.8 |
| 2"b | 1.99 | — |
| 3"a | 1.47 | 18.6 |
| 3"b | 1.88 | — |
| 4" | 2.28 | 64.9 |
| 5" | 3.49 | 73.4 |
| 6" | 1.28 | 19.0 |
| 4"-NMe$_2$ | 2.28 | 40.6 |

Chemical shifts referenced to the proton of CHCl$_3$ at 7.26 ppm.

21-desethyl-21-n-propyl spinosyn D (Compound 28) has the following characteristics.
Isolated yield: ~1 mg
Molecular weight: 759
Molecular formula: C$_{43}$H$_{69}$NO$_{10}$ This compound was present as the minor component in a 4:1 mixture with 6-ethyl spinosyn A. The accumulated UV and MS data for these two compounds are indistinguishable. Using NMR methods, the 21-n-propyl spin system could be assigned from correlations observed in the COSY spectrum of the mixture. Methyl H24 ($\delta_H$ 0.87, dd, 7.3 Hz, 7.3 Hz) was correlated to the methylene H23 ($\delta_H$ 1.23, m). H23 was correlated to the methylene H22 ($\delta_H$ 1.43, m) that in turn was correlated to H21 ($\delta_H$ 4.73, m). The H21 resonance was visible as an isolated multiplet in the $^1$H NMR spectrum of the mixture.

21-desethyl-21-n-propyl spinosyn A (Compound 23) has the following characteristics.
Isolated yield: 5.1 mg
Molecular weight: 745
Molecular formula: C$_{42}$H$_{67}$NO$_{10}$
UV (by diode array detection during HPLC analysis): 244 nm Electrospray MS: m/z for MH$^+$=746.5; forosamine sugar fragment ion at m/z=142.4.

The accumulated NMR data for this compound were identical to those described for this compound in Example 15.

Hybrid PKS genes constructed by the replacement of other AT (acyltransferase) domains within spn extender modules can be used to produce novel spinosyns with altered side chains at other positions on the polyketide. For example, in analogous methods to those described above, hybrid polyketide synthases can be constructed to yield spinosyns in which C18 or C20 bears a side chain other than a hydrogen (generally a methyl or ethyl). The native AT domains that incorporate predominantly methylmalonyl-CoA (such as spn AT3) can be replaced by heterologous domains that preferentially incorporate malonyl-CoA (such as rapamycin AT2) or ethylmalonyl-CoA (such as tylosin AT5). However, one skilled in the art will recognize that donor domains or modules for these hybrid polyketide synthases could be acquired from a variety of Type I polyketide synthase clusters and that this is not restricted in any way to domains or modules from erythromycin, avermectin, rapamycin and tylosin biosynthesis.

It is also anticipated that a combination of manipulations should lead to productive biosynthetic pathways, and spinosyns with two or more regions of novelty.

Additional biosynthetic genes may be required to provide an adequate supply of a precursor that is not normally incorporated into spinosyns, such as a ccr gene to increase ethylmalonyl-CoA supply. This genetic modification can also lead to the production of novel spinosyns by providing an unnatural precursor that is incorporated at other spn AT domains. The replacement of other spn AT domains could generate hybrid PKS genes which lead to the synthesis of spinosyns with an ethyl group at C6, or methyl or ethyl side chains at C18 or C20. The spn PKS domains responsible for the degree of modification of each beta-keto group (KR, DH or ER) might also be replaced by heterologous domains to generate hybrid PKS genes that result in spinosyns with different saturated bonds, hydroxyl groups or double bonds.

In summary, we have demonstrated that the hybrid spinosyn PKS genes claimed herein are useful for the production of novel, insecticidally-active spinosyns. The hybrid genes are derived from the spn PKS genes combined with a portion or portions of other Type I PKS genes. The strategies described in WO 98/01546 "Polyketides and their synthesis" were used to select the sites where the DNAs are spliced together. The hybrid genes can be operably linked to a heterologous promoter such as that from the actinorhodin biosynthetic gene acti (along with the actII-ORF4 gene encoding its cognate activator, see WO 98/01546), or from the pristinamycin resistance geneptr (Blanc et al., 1995). The hybrid PKS genes are expressed in an organism which also contains the non-PKS functions required to produce a biologically-active spinosyn. The modified strains provided by the invention may be cultivated to provide spinosyns using conventional protocols such as those disclosed in U.S. Pat. No. 5,362,634.

It is contemplated that the hybrid spinosyn PKSs of the invention can be expressed not only in *Saccharopolyspora spinosa*, but also in other host organisms, for example *Saccharopolyspora erythaea*, to produce insecticidally-active spinosyns. Other prokaryotic cells belonging to the group of actinomycetes, preferably the group of streptomycetes, are also suitable host organsims. *Streptomyces albus* is a specific example.

Pesticide Activity of New Spinosyns The compounds claimed herein are useful for the control of insects and mites. Included are all isomers of the compounds, and any acid addition salts of the compounds and their isomers. Also included are semi-synthetic derivatives made by the methods described in U.S. Pat. No. 6,001,981 to prepare other modified spinosyns.

The compounds show activity against a number of insects and mites. More specifically, the compounds show activity against members of the insect order Lepidoptera such as the beet armyworm, tobacco budworm, codling moth and cabbage looper. They also show activity against members of the order Coleoptera (the beetles and weevils) and Diptera (the true flies). The compounds also show activity against members of the order Hempitera (true bugs), Homoptera (aphids and hoppers), Thysanoptera (thrips), Orthoptera (cockroaches), Siphonaptera (fleas), Isoptera (termites), and members of the Hymenoptera order Formicidae (ants). The compounds also show activity against the two-spotted spider mite, which is a member of the Arachnid order Acarina.

A further aspect of the present invention is directed to methods for inhibiting an insect or mite. In one preferred embodiment, the present invention is directed to a method for inhibiting a susceptible insect that comprises applying to a plant an effective insect-inactivating amount of compound in accordance with the present invention. The claimed compounds are applied in the form of compositions, which are also a part of this invention. These compositions comprise an insect- or mite-inactivating amount of compound in an inert carrier. The active component may be present as a single claimed compound, a mixture of two or more compounds or a mixture of any of the compounds together with the dried portion of the fermentation medium in which it is produced. Compositions are prepared according to the procedures and formulas which are conventional in the agricultural or pest control art, but which are novel and important because of the presence of one or more of the compounds of this invention. The compositions may be concentrated formulations, which are dispersed in water or may be in the form of a dust, bait or granular formulation used without further treatment.

The action of the compositions according to the invention can be broadened considerably by adding other, for example insecticidally, acaricidally, and/or nematocidally active, ingredients. For example, one or more of the following compounds can suitably be combined with the compounds of the invention: organophosphorus compounds, carbamates, pyrethroids, acylureas, other types of insect growth regulators and insect hormone analogs, neonicotinoids and other nicotinics, macrolides and other insecticidal, acaricidal, mollscicial and nematocidal compounds or actives. WO 00/56156 on "Synergistic Insecticide Mixtures" discloses use of certain previously known spinosyn compounds in combination with agonists or antagonists of nicotinic acetylcholine receptors to control animal pests. WO 00/35282 on "Combination of Active Ingredients" discloses use of spinosad in combination with a flngicidally active compound. WO 00/35286 on "Combinations of Active Ingredients" discloses use of a combination of spinosad with other compounds to control animal pests and fungi. WO 99/60856 on "Use of Spinosyns as Soil Insecticides" discloses use of certain previously known spinosyns for treating seeds and for application to plants via the soil or by irrigation to control insects. WO 99/33343 on "Use of Macrolides in Pest Control" discloses use of spinosyns to control pests in transgenic crops, use of spinosyns to protect plant propagation material and plant organs formed at a later time from attack by pests, and use of spinosyns to control wood pests and molluscs. The compounds of Formula I can also be used for these purposes.

The compounds of the present invention are also useful for the treatment of animals to control arthropods, i.e., insects and arachnids including various flies and fly larvae, fleas, lice, mites, and ticks, which are pests on animals. Techniques for delivering ectoparasiticides are well known to those skilled in the art. In general, a present compound is applied to the exterior surface of an animal by sprays, dips or dusts. The compounds can also be delivered to animals using ear tags, a delivery method disclosed in U.S. Pat. No. 4,265,876.

In yet another embodiment, the compounds can be used to control insects and arachnids which are pests in the feces of cattle and other animals. In this embodiment, the compounds are administered orally and the compounds travel through the intestinal tract and emerge in the feces. Control of pests in the feces indirectly protects the animals from the pests.

The compounds of the invention are also useful as human pharmaceuticals to control parasites, for example, lice. The compounds can be used, for example, in the formulations for controlling lice that are disclosed in WO 00/01347.

EXAMPLE 25

Demonstration that Novel Purified Spinosyns are Insecticidal

Biological activity of the compounds of the invention was shown by a topical assay in which the compound was applied to laboratory-reared larvae (mean weight 22 mg) at the rate of 1 microg/larva. Each compound was applied, in an acetone solution (1 mg/mL), along the dorsum of six tobacco budworm (*Heliothis virescens*) larvae and six beet armyworm (*Spodoptera exigua*) larvae. Treated larvae were then held for two days at 21° C., 60% RH in six-well plastic culture plates. Larvae were each supplied with a 1 cm$^3$ of agar-based lepidoptera diet for sustenance during the two-day post-exposure interval. Percent mortality was determined at the end of a two-day period (Table 18).

TABLE 18

| Compound | Compound No. (See Table 3) | Tobacco Budworm | | Beet Armyworm | |
|---|---|---|---|---|---|
| | | Rate (micro/larva) | Mortality (%) | Rate (microg/larva) | Mortality (%) |
| solvent only | | 0 | 0 | 0 | 0 |
| 21-cyclopropyl | 1 | 1 | 100 | 1 | 33 |
| 21-cyclobutyl | 3 | 1 | 83 | 1 | 83 |
| 21-cyclobutyl,6-methyl | 4 | 1 | 100 | 1 | 83 |
| 21-cyclobutyl,5,6-dihydro | 8 | 1 | 100 | 1 | 83 |
| 21-isopropyl | 9 | 1 | 100 | 1 | 100 |
| 21-n-propyl | 23 | 1 | 100 | 1 | 100 |

The compounds of formula (I) can be used as intermediates in the processes disclosed in U.S. Pat. No. 6,001,981 to produce semi-synthetic spinosyn analogues, which are also expected to have insecticidal activity.

The US patents and patent applications cited hereinabove are hereby incorporated by reference.

REFERENCES

1) Bierman, M., Logan, R., O'Brien, K., Seno, E T., Nagaraja Rao, R. and Schoner, B E. (1992) "Plasmid cloning vectors 1) for the conjugal transfer of DNA from *Escherichia coli* to *Streptomyces* spp." Gene 116: 43-49.
2) Bisang, C., Long, P F., Cortes, J., Westcott, J., Crosby, J., Matharu, A L., Cox, R J., Simpson, T J., Staunton, J. and Leadlay, P F. (1999) "A chain initiation factor common to both modular and aromatic polyketide synthases." *Nature* 401: 502-505.
3) Blanc, V., Salah-Bey, K., Folcher, M. and Thompson, C J. (1995) "Molecular characterization and transcriptional analysis of a multidrug resistance gene cloned from the pristinamycin-producing organism, *Streptomyces pristinaespiralis*." *Mol. Microbiol.* 17: 989-999.
4) Broughton, M C., Huber, M L B., Creemer, L C., Kirst, H A. and Turner J R. (1991) "Biosynthesis of the macrolide insecticidal compound A83543 by *Saccharopolyspora spinosa*." *Proceedings of Amer. Soc. Microbiol.*, Washington D.C.
5) Donadio, S., Staver, M J., McAlpine, J B., Swanson, S J. and Katz, L. (1991) "Modular organization of genes required for complex polyketide biosynthesis." *Science* 252: 675-679.
6) Donadio, S A., Stassi, D., McAlpine, J B., Staver, M J., Sheldon, P J., Jackson, M., Swanson, S J., Wendt-Pienkowski, E., Wang, Y G., Jarvis, B., Hutchinson, C R. and Katz, L. (1993) "Recent developments in the genetics of erythromycin formation." In *Industrial microorganisms: basic and applied molecular genetics*. (Baltz, R H., Hegeman, G D. and Skatrud, P L., eds), pp. 257-265. Amer. Soc. Microbiol, Washington D.C.
7) Dutton, C J., Gibson, S P., Goudie, AC., Holdom, K S., Pacey, M S., Ruddock, J C., Bu'Lock, J D. and Richards, M K. (1991) "Novel avermectins produced by mutational biosynthesis." *J. Antibiot.* 44: 357-365.
8) Hosted, T J. and Baltz, R H. (1996) "Mutants of *Streptomyces roseosporus* that express enhanced recombination within partially homologous genes." Microbiology 142: 2803-2813.
9) Hunziker, D., Yu, T W., Hutchinson, C R., Floss, H G. and Khosla, C. (1998) "Primer unit specificity in rifamycin biosynthesis principally resides in the later stages of the biosynthetic pathway." *J. Am. Chem. Soc.* 12: 1092-1093.
10) Kirst, H A., Michel, K H., Martin, J W., Creemer, L C., Chio, E H., Yao, R C., Nakatsukasa, W M., Boeck, L D., Occolowitz, J L., Paschal, J W., Deeter, J B., Jones, N D. and Thompson, G D. (1991) "A83543A-D, unique fermentation-derived tetracyclic macrolides." *Tetrahedron Letts* 32: 4839-4842.
11) Marsden, A F A., Wilkinson, B., Cortés, J., Dunster, N J., Staunton, J. and Leadlay, P F. (1998) "Engineering broader specificity into an antibiotic-producing polyketide synthase." *Science* 279: 199-202.
12) Matsushima, P., Broughton, M C., Turner, J R. and Baltz, R H. (1994) "Conjugal transfer of cosmid DNA from *Escherichia coli* to *Saccharopolyspora spinosa*: effects of chromosomal insertions on macrolide A83543 production." *Gene* 146: 39-45.
13) Pacey, M S., Dirlam, J P., Geldart, R W., Leadlay, P F., McArthur, H A I, McCormick, E L., Monday, R A., O'Connell, T N, Staunton, J. and Winchester, T J. (1998) "Novel erythromycins from a recombinant *Saccharopolyspora erythraea* strain NRRL 2338 pIGI. Fermentation, isolation and biological activity," *J. Antibiot.* 51: 1029-1034.
14) Rowe, C J., Cortés, J., Gaisser, S., Staunton, J. and Leadlay, P F. (1998) "Construction of new vectors for high-level expression in actinomycetes," *Gene* 216: 215-223.
15) Salah-Bey, K., Blanc, V. and Thompson, C J. (1995) "Stress-activated expression of a *Streptomyces pristinaespiralis* multi drug resistance gene (ptr) in various *Streptomyces* spp. and *Escherichia coli*." *Mol. Microbiol.* 17: 1001-1012.
16) Simon, R., Preifer, U. and Puhler, A. (1983) "A broad host range mobilization system for in vivo genetic engineering: transposon mutagenesis in Gram negative bacteria." *Bio/Technology* 1: 784-791.
17) Stassi, D L., Kakavas, S J, Reynolds, K A, Gunawardana, G., Swanson, S., Zeidner, D., Jackson, M., Liu, H., Buko, A. and Katz, L. (1998) "Ethyl-substituted erythromycin derivatives produced by directed metabolic engineering." *Proc. Natl. Acad. Sci. USA* 95: 7305-7309.
18) Strobel, R J. and Nakatsukasa W M. (1993) "Response surface methods for optimizing *Saccharopolyspora spinosa*, a novel macrolide producer." *J. Indust. Microbiol.* 11: 121-127.
19) Waldron, C., Matsushima, P., Rosteck, P R., Jr., Broughton, M C., Turner, J., Madduri, K., Crawford, K P., Merlo, D J. and Baltz, R H. (2001) "Cloning and analysis of the spinosad biosynthetic gene cluster of *Saccharopolyspora spinosa*." *Chem. Biol.* 8: 487-499

The invention claimed is:

1. A polynucleotide encoding a hybrid spinosyn polyketide synthase capable of functioning in *Saccharopolyspora spinosa* to produce a biologically active spinosyn, said hybrid polyketide synthase-encoding polynucleotide comprising a heterologous loading module encoded by a nucleic acid sequence selected from the group consisting of the nucleic acid sequence set forth in SEQ ID NO:8 and the nucleic acid sequence set forth in SEQ ID NO:11, wherein said heterologous loading module-encoding nucleic acid sequence is fused in frame to a nucleic acid encoding a *Saccharopolyspora spinosa* ketosynthase 1 (KS1) extender module and said KS1 extender module is fused in frame to a plurality of additional *Saccharopolyspora spinosa* extender modules.

2. The hybrid spinosyn polyketide synthase-encoding polynucleotide of claim 1 comprising the loading module-encoding nucleic acid sequence set forth in SEQ ID NO:8.

3. The hybrid spinosyn polyketide synthase-encoding polynucleotide of claim 1 comprising the loading module-encoding nucleic acid sequence set forth in SEQ ID NO:11.

* * * * *

UNITED STATES PATENT AND TRADEMARK OFFICE
CERTIFICATE OF CORRECTION

| | | |
|---|---|---|
| PATENT NO. | : 7,626,010 B2 | Page 1 of 1 |
| APPLICATION NO. | : 11/254686 | |
| DATED | : December 1, 2009 | |
| INVENTOR(S) | : Burns et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1018 days.

Signed and Sealed this

Second Day of November, 2010

David J. Kappos
*Director of the United States Patent and Trademark Office*

SEQUENCE LISTING

<160> NUMBER OF SEQ ID NOS: 26

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: oligo PRIS1

<400> SEQUENCE: 1
ggggaattca ctagtccgcg gagaaatagc gctgtacagc gtatgggaat ctcttgtacg     60
g                                                                     61

<210> SEQ ID NO 2
<211> LENGTH: 68
<212> TYPE: DNA

```
<213> ORGANISM: Artificial Sequence
<220> FEATURE:
<223> OTHER INFORMATION: Description of Artificial Sequence: oligo PRIS2

<400> SEQUENCE: 2
gggggatccc atatgggctc cttgtacggt gtacgggaag atactcgtac accgtacaag      60
agattccc                                                               68

<210> SEQ ID NO 3
<211> LENGTH: 94
<212> TYPE: DNA
<213> ORGANISM: Streptomyces pristinaespiralis

<400> SEQUENCE: 3
actagtccgc ggagaaatag cgctgtacag cgtatgggaa tctcttgtac ggtgtacgag      60
tatcttcccg tacaccgtac aaggagccca tatg                                  94

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence:oligo CR311

<400> SEQUENCE: 4
cagatatcac tagttcggac gcatatgctg caagtatcta gaac                       44

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence:oligo CR312

<400> SEQUENCE: 5
gttctagata cttgcagcat atgcgtccga actagtgata tctg                       44

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: oligo SP28

<400> SEQUENCE: 6
aggacacata tggcggacct gtcaaagctc tc                                    32

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: oligo SP29

<400> SEQUENCE: 7
cccgctagcg gttcgccggg cgccgcttcg ttgg                                  34

<210> SEQ ID NO 8
<211> LENGTH: 1685
<212> TYPE: DNA
<213> ORGANISM: Saccharopolyspora erythraea

<400> SEQUENCE: 8
catatggcgg acctgtcaaa gctctccgac agtcggactg cacaacctgg gaggatcgtt      60
```

```
cgtccgtggc ccctgtcggg gtgcaatgaa tccgccttgc gggcccgtgc gcgccaattg    120
cgtgcacatc tcgatcgatt tcccgatgcc ggtgtcgaag gtgtcggggc gcgcgctcgcg   180 cacgacgagc aggcggacgc cggtccgcat cgcgcggtcg tcgtcgcctc ctcgacctcc    240
gagctgctcg acggcctggc cgccgtcgcc gacggccggc cgcacgcctc ggtggtccgc    300
ggcgtggccc ggccgtccgc gccggtggtg ttcgtcttcc cgggccaggg cgcgcaatgg    360
gccgggatgg cgggcgaact cctcggcgag tcaagggttt cgccgccgc gatggacgcg     420 tgcgcgcggg cgttcgagcc cgtgaccgac tggacgctgg cgcaggtcct ggactctccc    480
gagcagtcgc gccgcgtcga ggtcgtccag cccgccctgt tcgcggtgca gacgtcgctg    540
gccgcgctct ggcgctcctt cggcgtgacc cccgacgccg tggtgggcca cagcatcggc    600
gagctggccg ccgcgcacgt gtgcggtgcg gccggtgccg ccgacgccgc gcgcgccgcc    660
gcgctgtgga gccgcgagat gattccgttg gtgggcaacg cgacatggc agccgtcgcg     720 ctctccgccg acgagatcga gccgcgcatc gcccggtggg acgacgacgt ggtgctggcc    780
ggggtcaacg gtccgcgctc ggttctgctg accgggtcgc cggaaccggt cgcgcgccgg    840
gtccaggagc tctcggccga gggggtccgc gcacaggtca tcaatgtgtc gatggcggcg    900
cactcggcgc aggtcgacga catcgccgag gggatgcgct cggccctggc gtggttcgcg    960
cccggtggct cggaggtgcc cttctacgcc agcctcaccg gaggtgcggt cgacacgcgg    1020
gagctggtgg ccgactactg gcgccgcagc ttcggctgc cggtgcgctt cgacgaggcg     1080
atccggtccg ccctggaggt cggtcccggc acgttcgtcg aagcgagccc gcacccggtg    1140
ctggccgccg cgctccagca gacgctcgac gccgagggct cctcggccgc ggtggtcccg    1200
acgctgcaac gcgggcaggg cggcatgcgg cggttcctgc tggccgcggc ccaggcgttc    1260
accggcggcg tggccgtcga ctggaccgcc gcctacgacg acgtgggggc cgaacccggc    1320
tctctgccgg agttcgcgcc ggccgaggag gaagacgagc cggccgagtc cggcgtcgac    1380
tggaacgcgc caccgcacgt gctgcgcgag cggctgctcg cggtcgtcaa cggcgagacc    1440
gccgcgttgg cgggccgcga agccgacgcc gaggccacgt tccgcgagct ggggctggac    1500
tcggtgctgg ccgcgcagct gcgcgccaag gtgagcgccg cgatcgggcg cgaggtcaac    1560
atcgccctgc tctacgacca cccgactccg cgtgcgctcg cggaagcact cgcggcggga    1620
accgaggtcg cacaacggga aacccgcgcg cggaccaacg aagcggcgcc cggcgaaccg    1680
ctagc                                                               1685
```

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: oligo SP14

<400> SEQUENCE: 9

```
aagctagccg tgatcgggat gggctgtcgg tt                                  32
```

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: oligo SP15

<400> SEQUENCE: 10

```
atagcggccg cccccagccc ccacagatcc ggtcaccaa                              39
```

<210> SEQ ID NO 11
<211> LENGTH: 1694
<212> TYPE: DNA
<213> ORGANISM: Streptomyces avermitilis

<400> SEQUENCE: 11

```
catatggcgg aacctgtcaaa gctctccgac agtcggactg cacaacctgg gaggatcgtt     60
cgtccgtggc ccctgtcggg gtgcaatgaa tccgccttgc gggcccgtgc gcgccaattg    120
cgtgcacatc tcgatcgatt tcccgatgcc ggtgtcgaag gtgtcggggc gcgctcgcg     180
cacgacgagc aggcggacgc cggtccgcat cgcgcggtcg tcgtcgcctc ctcgacctcc    240
gagctgctcg acggcctggc cgccgtcgcc gacggccggc cgcacgcctc ggtggtccgc    300
ggcgtggccc ggccgtccgc gccactagtc ttcgttttttc ccgggcaggg cccgcaatgg    360
ccgggcatgg gaagggaact tctcgacgct tccgacgtct tccggagag cgtccgcgcc     420
tgcgaagccg cgttcgcgcc ctacgtcgac tggtcggtgg agcaggtgtt gcgggactcg    480
ccggacgctc ccgggctgga ccgggtggac gtcgtccagc cgaccctgtt cgccgtcatg    540
atctccctgg ccgccctctg gcgctcgcaa ggggtcgagc cgtgcgcggt gctgggacac    600
agcctgggcg agatcgcggc agcccacgtc tcgggaggcc tgtccctggc cgacgccgca    660
cgcgtggtga cgctttggag ccaggcacag accaccccttg ccgggaccgg cgcgctcgtc    720
tccgtcgccg ccacgccgga tgagctcctg ccccgaatcg ctccgtggac cgaggacaac    780
ccggcgcggc tcgccgtcgc agccgtcaac ggaccccgga gcacagtcgt ttccggtgcc    840
cgcgaggccg tcgcggacct ggtggccgac ctcaccgccg cgcaggtgcg cacgcgcatg    900
atcccggtgg acgttcccgc ccactccccc ctgatgtacg ccatcgagga acgggtcgtc    960
agcggcctgc tgcccatcac cccacgcccc tcccgcatcc ccttccactc ctcggtgacc   1020
ggcggccgcc tcgacacccg cgagctagac gcggcgtact ggtaccgcaa catgtcgagc   1080
acgtccggt tcgagcccgc cgcccggctg cttctgcagc agggggccaa gacgttcgtc    1140
gagatgagcc cgcacccggt gctgaccatg ggcctccagg agctcgccgc ggacctgggc   1200
gacaccaccg gcaccgccga caccgtgatc atgggcacgc tgcgccgcgg ccagggcacc   1260
ctggaccact tcctgacgtc tctcgcccaa ctacgggggc atggtgagac gtcggcgacc   1320
accgtcctct cggcacgcct gaccgcgctg tcccccacgc agcagcagtc gctgctcctg   1380
gacctggtgc gcgcccacac catggcgtg ctgaacgacg acggaaacga gcgcaccgcg     1440
tcggatgccg gccatcggc gagtttcgcc cacctcggct tcgactccgt catgggtgtc   1500
gaactgcgca accgcctcag caaggccacg ggcctgcggt tgcccgtgac gctcatcttc   1560
gaccacacca cgccggccgc ggtcgccgcg cgccttcgga ccgcggcgct cggccacctc   1620
gacgaggaca ccgcgcccgt accggactca cccagcggcc acgaggcac ggcagcggcg     1680
gacgacccgc tagc                                                     1694
```

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: oligo CR322

<400> SEQUENCE: 12

```
aatggccagg gctggcagtg ggccggtatg gca                                   33
```

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: oligo CR323

<400> SEQUENCE: 13
aacctaggaa cgccacggcc cagtccacgg t                                   31

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: oligo CR324

<400> SEQUENCE: 14
aacctaggcg cgggccgacg gctggacct                                      29

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: oligo CR325

<400> SEQUENCE: 15
cgacacgcac gtctcatcct ggtcaa                                         26

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: oligo CR328

<400> SEQUENCE: 16
tatcactcta gaccagatat ccagctgca                                      29

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: oligo CR329

<400> SEQUENCE: 17
gctggatatc tggtctagag tga                                            23

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: oligo CR330

<400> SEQUENCE: 18
ttcctggagg gaaacgccat atgtcgaatg aagagaag                            38

<210> SEQ ID NO 19
<211> LENGTH: 34
<212> TYPE: DNA
<213> ORGANISM: Artificial Sequence
<220> FEATURE:

```
<223> OTHER INFORMATION: Description of Artificial Sequence: oligo CR321

<400> SEQUENCE: 19
tttggccagg gaagacgaag acgacctcgc cgtc                                34

<210> SEQ ID NO 20
<211> LENGTH: 837
<212> TYPE: DNA
<213> ORGANISM: Streptomyces hygroscopicus

<400> SEQUENCE: 20
tggccagggg tcgcagcgtg ctggtatggg tgaggaactg gccgccgcgt tccccgtctt     60
cgcgcggatc catcagcagg tgtgggatct gctggatgtg cccgatctcg atgtgaatga    120
gaccgggtat gcccagccgg ccctgttcgc tttgcaggtg gctctgttcg ggttgctgga    180
atcgtggggt gtacggccgg atgcggtggt cggtcactct gtcggtgagc tcgccgccgg    240
atacgtctcc ggggttgtgg tcgttggagga tgcctgcact tggtgtcgg cgcgggctcg    300 tctgatgcag gctctgcctg cgggtggggt gatggtcgct gtcccggtct cggaggatga    360
ggctcgggcc gtgctgggtg agggtgtgga tcgccgcg gtcaacgggc cgtcgtcggt    420
ggttctctcc ggtgatgagg ccgccgtgct gcaggccgcg gaggggctgg ggaagtggac    480
gcggctggcg accagtcacg cgttccattc cgcccgtatg gaaccgatgc tggaggagtt    540
ccgggcggtc gctgaaggcc tgacctaccg gacgccgcag gtcgccatgg ccgctggtga    600
tcaggtgatg accgctgagt actgggtgcg gcaggtccgg gacacggtcc ggttcggcga    660
gcaggtggcc tcgttcgagg atgcggtgtt cgtcgagctg ggtgccgacc ggtcactggc    720
ccgcctggtc gatggcatcg cgatgctgca cggtgaccat gaggcgcagg ccgctgtcgg    780
tgccctggct cacctgtacg tgaacggcgt gagtgtcgag tggtccgcgg tcctagg      837

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: oligo
      CCRMONF

<400> SEQUENCE: 21
ggcaaacata tgaaggaaat cctggacgcg                                    30

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: oligo
      CCRMONR

<400> SEQUENCE: 22
tccgcggatc ctcagtgcgt tcagatcagt gc                                 32

<210> SEQ ID NO 23
<211> LENGTH: 1394
<212> TYPE: DNA
<213> ORGANISM: Streptomyces cinnamonensis

<400> SEQUENCE: 23
catatgaagg aaatcctgga cgcgattcag gcccagaccg cgaccgcgag cggcaccgcc     60
gcggtcacgt ccgccgactt cgccgctctc cccctgcccg actcgtaccg cgcgatcacc    120
```

```
gtgcacaagg acgagacgga gatgttcgcg ggcctcgagt cccgtgacaa ggaccccgc      180 aagtcgctcc atctggacga cgtgccgatc ccgaactcg gccccggtga ggccttggtg      240
gccgtcatgg cctcctcggt caactacaac tccgtgtgga cctcgatctt cgagcccgtc    300
tccaccttca gcttcctgga gcggtacggc cggctcagcg acctgagcaa gcgccacgac    360
ctgccgtacc acatcatcgg ctccgacctg cggggcgtcg tgctgcgcac cgggcccggc    420
gtgaacgcct ggaacccggg cgacgaggtc gtcgcgcact gcctgagcgt cgagctggag    480
tcctccgacg gccacaacga cacgatgctc gaccccgagc agcgcatctg ggcttcgag     540 accaacttcg gcggtctcgc cgagatcgcg ctcgtcaagt ccaaccagct catgccgaag    600
cccggtcacc tgagctggga ggaggccgcc tcgcccggcc tggtgaactc caccgcgtac    660
cgccagctgg tgtcccgcaa cggcgccggc atgaagcagg gcgacaacgt gctgatctgg    720
ggcgcgagcg gcggactcgg gtcgtacgcc acgcagttcg cgctcgccgg cggcgccaac    780
cccatctgtg tcgtctccag cccccagaag gcggagatct gccgcgcgat gggcgccgag    840
gcgatcatcg accgcaacgc cgagggctac aagttctgga aggacgagca gacccaggac    900
cccaaggagt ggaagcgctt cggcaagcgc atccgcgagc tcaccggcgg cgaggacatc    960
gacatcgtct tcgagcaccc cggccgcgag accttcggcg cctcggtcta cgtcacgcgc   1020
aagggcggca ccatcaccac ctgcgcctcg acctcgggct acatgcacga gtacgacaac   1080
cgctacctgt ggatgtccct gaagcgcatc atcggctcgc acttcgccaa ctaccgcgag   1140
gcgtgggagg ccaaccgcct gatcgccaag ggcaagatcc acccgacgct ctccaagacg   1200
taccgcctgg aggacaccgg ccaggccgcc tacgacgtcc accgcaacct ccaccagggc   1260
aaggtcggcg tcctcgccct cgcgcccgag gagggcctgg gcgtgcgcga cccggagaag   1320
cgggcccagc acatcgacgc gatcaaccgt ttccgcaacg tctgaacgca ctgatctgaa   1380
cgcactgagg atcc                                                     1394

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: oligo AK1

<400> SEQUENCE: 24
aatggccagg gctcgcagtg gccgtcgatg gccc                                34

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: oligo AK2

<400> SEQUENCE: 25
ttcctaggaa gagggcttct ccgtcgatct ccagtc                              36

<210> SEQ ID NO 26
<211> LENGTH: 972
<212> TYPE: DNA
<213> ORGANISM: Streptomyces fradiae

<400> SEQUENCE: 26
tggccagggc tcgcagtggc cgtcgatggc ccgggacctg ctcgaccgcg cgcccgcctt     60
```

-continued

```
ccgcgagacg gcgaaggcct gcgacgccgc gctgagcgtc catctggact ggtccgtgct    120
cgatgtcctc caggagaagc cggacgcgcc gccgctgagc cgggtcgacg tggtgcagcc    180
cgtgctgttc acgatgatgc tgtcgctcgc cgcctgctgg cgggacctcg gcgtccaccc    240
ggccgccgtg gtgggccact cccagggaga gatcgcggcg gcctgcgtgg ccggcgcgct    300
ctccctggag gacgcggcgc ggatcgtggc gctgcgcagc cgggcatggc tcacactggc    360
cggcaagggc ggcatggccg ccgtctccct gccggaagcc cggctgcgcg agcggatcga    420
gcggttcggg cagcggctgt cggtggccgc ggtgaacagc ccgggcacgg cggcggtcgc    480
cggtgacgtg gacgcgctgc gggaactgct ggcggagctg accgcggagg gcatccgggc    540
caagccgatc cccggcgtgg acacggccgg ccactccgcg caggtggacg gcctgaagga    600
gcatctcttc gaggtgctgg cgccggtctc cccgcgctcc tcggacatcc cgttctactc    660
gacggtgacg ggcgcgccgc tggacaccga gcggctggac gccgggtact ggtaccgcaa    720
catgcgggag cccgtggagt tcgagaaggc cgtcagggca ctgatcgccg acggctacga    780
cctgttcctg gagtgcaacc cgcacccgat gctcgccatg tcgctggacg agacactcac    840
cgacagcggc ggccacggca ccgtgatgca caccctccgc cggcagaagg gcagcgccaa    900
ggacttcggc atggcgctct gcctcgccta tgtcaacgga ctggagatcg acggagaagc    960
cctcttccta gg                                                        972
```